United States Patent
Deng et al.

(10) Patent No.: US 12,351,576 B2
(45) Date of Patent: Jul. 8, 2025

(54) FGFR INHIBITOR, PREPARATION METHOD THEREFOR AND APPLICATION THEREOF

(71) Applicant: Abbisko Therapeutics Co., Ltd., Shanghai (CN)

(72) Inventors: Haibing Deng, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 848 days.

(21) Appl. No.: 17/253,113

(22) PCT Filed: Jul. 23, 2019

(86) PCT No.: PCT/CN2019/097361
§ 371 (c)(1),
(2) Date: Dec. 16, 2020

(87) PCT Pub. No.: WO2020/052349
PCT Pub. Date: Mar. 19, 2020

(65) Prior Publication Data
US 2021/0261544 A1    Aug. 26, 2021

(30) Foreign Application Priority Data
Sep. 14, 2018 (CN) .......................... 201811073492.1

(51) Int. Cl.
  *C07D 471/04* (2006.01)
  *A61P 35/00* (2006.01)
  *C07D 519/00* (2006.01)

(52) U.S. Cl.
  CPC ............ *C07D 471/04* (2013.01); *A61P 35/00* (2018.01); *C07D 519/00* (2013.01)

(58) Field of Classification Search
  CPC ........................... C07D 471/04; C07D 519/00
  See application file for complete search history.

(56) References Cited

U.S. PATENT DOCUMENTS

| | | |
|---|---|---|
| 2003/0220345 A1 | 11/2003 | Jamby et al. |
| 2005/0187230 A1 | 8/2005 | Ding et al. |
| 2008/0176846 A1 | 7/2008 | Chianelli et al. |
| 2009/0312321 A1 | 12/2009 | Ren et al. |
| 2014/0088100 A1 | 3/2014 | Bifulco, Jr. et al. |
| 2014/0163026 A1 | 6/2014 | Campbell et al. |
| 2015/0197519 A1 | 7/2015 | Bifulco, Jr. et al. |
| 2016/0046634 A1 | 2/2016 | D'Agostino et al. |
| 2016/0200725 A1 | 7/2016 | Verner et al. |

FOREIGN PATENT DOCUMENTS

| | | |
|---|---|---|
| CN | 104540809 A | 4/2015 |
| CN | 108264511 A | 7/2018 |
| CN | 108864081 A | 11/2018 |
| JP | 2004519422 A | 7/2004 |
| JP | 2007508310 A | 4/2007 |
| JP | 2009537520 A | 10/2009 |
| JP | 2010506948 A | 3/2010 |
| JP | 2014513079 A | 5/2014 |
| JP | 2015523383 A | 8/2015 |
| JP | 2016519673 A | 7/2016 |
| JP | 2017505782 A | 2/2017 |
| WO | 0218379 A2 | 3/2002 |
| WO | 2004063195 A1 | 7/2004 |
| WO | 2005034869 A2 | 4/2005 |
| WO | 2015108992 A1 | 7/2015 |
| WO | 2016115412 A1 | 7/2016 |
| WO | 2016191172 A1 | 12/2016 |
| WO | 2018160076 A1 | 9/2018 |
| WO | WO-2018205916 A1 * | 11/2018 ......... A61K 31/4375 |

OTHER PUBLICATIONS

Wang, Y. et al., Google English translation of WO 2018/205916, published Nov. 2018 (Year: 2018).*
Brameld, Ken A. et al., J of Medicinal Chemistry, "Discovery of the Irreversible Covalent FGFR Inhibitor 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one (PRN1371) for the Treatment of Solid Tumors", 2017, vol. 60, 6516-27 (Year: 2017).*
Extended European Search Report issued Apr. 8, 2021 in EP Application No. 19861022.2.
"CAS 1902183-52-1, 1902183-51-0 et al." REG (STN), May 2, 2016.
Int'l Search Report issued Oct. 23, 2019 in Int'l Application No. PCT/CN2019/097361.
Trumpp-Kallmeyer et al, "Development of a Binding Model to Protein Tyrosine Kinases for Substituted Pyrido [2,3-d] pyrimidine Inhibitors," Journal of Medicinal Chemistry, vol. 41, No. 11, pp. 1752-1763 (1998).
Zhang et al, "Part 3: Notch-sparing c-secretase inhibitors: SAR studies of 2-substituted aminopyridopyrimidinones," Bioorganic & Medicinal Chemistry Letters, vol. 26, pp. 2138-2141 (2016).

(Continued)

*Primary Examiner* — Bahar Craigo
(74) *Attorney, Agent, or Firm* — Panitch Schwarze Belisario & Nadel LLP

(57) ABSTRACT

A compound having a structure of formula (I) and a preparation method therefor, and a use of the compound serving as an FGFR inhibitor for treating tumors, cancers, myeloproliferative diseases, bone or chondrocyte disorders, and hypophosphatemia.

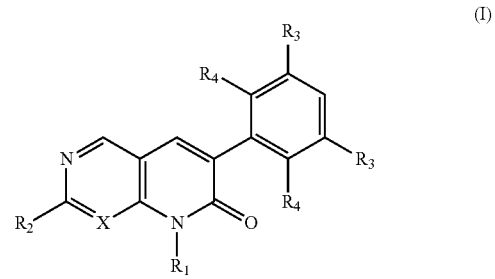

(I)

6 Claims, No Drawings

(56) References Cited

OTHER PUBLICATIONS

Montoir et al., "Differential Functionalization of 1,6-Naphthyridin-2(1H)-ones through Sequential One-Pot Suzuki-Miyaura Cross-Couplings," Eur. J. Org. Chem., pp. 1487-1495 (2014).
Office Action issued Jan. 26, 2022 in JP Application No. 2020570836.
Thompson et al., "Synthesis and Structure—Activity Relationships of 7-Substituted 3-(2,6-Dichlorophenyl)-1,6-naphthyridin-2(1H)-ones as Selective Inhibitors of pp60," J. Med. Chem., vol. 43, pp. 3134-3147 (2000).

* cited by examiner

FGFR INHIBITOR, PREPARATION METHOD THEREFOR AND APPLICATION THEREOF

CROSS-REFERENCE TO RELATED APPLICATIONS

This application is a Section 371 of International Application No. PCT/CN2019/097361, filed Jul. 23, 2019, which was published in the Chinese language on Mar. 19, 2020, under International Publication No. WO 2020/052349 A1, which claims priority under 35 U.S.C. § 119(b) to Chinese Application No. 201811073492.1, filed Sep. 14, 2018, the disclosures of each of which are incorporated herein by reference in their entireties.

TECHNICAL FIELD

The present invention belongs to the field of medicament synthesis, and in particular relates to an FGFR inhibitor, preparation method therefor and application thereof.

BACKGROUND

Fibroblast growth factor receptor (FGFR) is a receptor tyrosine kinase that binds to fibroblast growth factor ligand. So far four FGFRs have been found to be bound to ligands and get closely involved in a variety of physiological processes including tissue differentiation, angiogenesis, wound healing, and metabolic regulation. The binding of ligands to the receptors may result in dimerization and phosphorylation of the receptors, thereby stimulating the activation of protein kinase activity and recruiting numerous intracellular proteins to bind to. The interactions among these proteins promote the activation of a series of intracellular signal pathways including Ras-MAPK, AKT-PI3K, and phosphatase C which are very important for cell growth, proliferation and survival.

The aberrant activation of these signal pathways, for example, over-expression of FGF ligands or the activating FGFR mutations may give rise to tumor growth, progression and resistance to conventional cancer therapies. The genetic changes, including gene amplification, chromosome translocation and somatic mutation, that give rise to ligand-independent activation of receptors have been described in human cancer. Large-scale DNA sequencing of thousands of tumor samples has revealed that the components of the FGFR signal pathway are susceptible to high-frequency mutation in human cancers. For example, somatic FGFR1 mutations have been identified in glioma and lung cancer; FGFR2 mutations are common in gastric cancer and endometrial cancer; FGFR3 mutations have been identified in bladder cancer and multiple myeloma; and FGFR4 mutations have been identified in primary rhabdomyosarcoma.

FGF/FGFR related tumor types include but are not limited to cancers (e.g., bladder cancer, breast cancer, cervical spinal cancer, colon cancer, endometrial cancer, gastric cancer, head and neck cancer, renal carcinoma, hepatic carcinoma, lung cancer, ovarian cancer, prostate cancer); haematological malignancy (e.g., multiple myeloma, chronic lymphocytic lymphoma, adult T cell leukemia, acute myelogenous leukemia, non-Hodgkin lymphoma, myeloproliferative neoplasm and Waldenstrom macroglobulinemia) and other tumors (e.g., glioblastoma, melanoma and rhabdomyosarcoma). In addition to its role in tumors, FGFR activation has been found to be related to pathological changes of bones and cartilage cell, such as achondroplasia and craniosynostosis.

Although some FGFR inhibitors have been under clinical/preclinical development, but they usually suffer from poor selectivity and show inhibition on other kinases like c-kit and PDGFRa, which to some extent raises concerns on therapeutic window of these inhibitors. In light of this, the development of selective inhibitors targeting FGFR is of great significance in the clinical treatment of diseases with increased FGF or FGFR activities.

SUMMARY

The object of the present invention is to provide an FGFR inhibitor.

The first aspect of the invention provides a compound of formula (I), a stereoisomer, prodrug or pharmaceutically acceptable salt thereof:

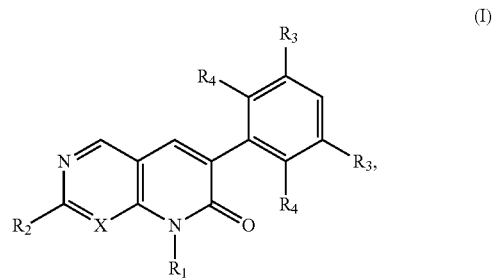

wherein, X is CH or N;

$R_1$ is selected from the group consisting of H, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —S(O)$R_5$, —S(O)$_2R_6$ and —C(O)$R_7$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, —$C_{0-8}$—S(O)$_rR_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—N$R_{13}R_{14}$, —$C_{0-8}$—C(=NR)$R_{12}$, —$C_{0-8}$—N($R_{13}$)—C(=N$R_{14}$)$R_{12}$, —$C_{0-8}$—C(O)N$R_{13}R_{14}$ and —$C_{0-8}$—N($R_{13}$)—C(O)$R_{12}$;

$R_2$ is selected from the group consisting of $C_{3-10}$ cycloalkyl, 3-10 membered heterocyclyl, $C_{5-10}$ aryl, 5-10 membered heteroaryl and —N$R_8R_9$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, —$C_{0-8}$—S(O)$_rR_{10}$, —$C_{0-8}$—O—$R_{11}$, —$C_{0-8}$—C(O)O$_{11}$, —$C_{0-8}$—C(O)$R_{12}$, —$C_{0-8}$—O—C(O)$R_{12}$, —$C_{0-8}$—N$R_{13}R_{14}$, —$C_{0-8}$—C(=N$R_{13}$)$R_{12}$, —$C_{0-8}$—N($R_{13}$)—C(=N$R_{14}$)$R_{12}$, —$C_{0-8}$—C(O)N$R_{13}R_{14}$ and —$C_{0-8}$—N($R_{13}$)—C(O)$R_{12}$, above groups are optionally more further substituted by one or more substituents selected from the group consisting of deuterium, halogen, cyano, nitro, azido, $C_{1-10}$ alkyl, $C_{1-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$$R_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—N$R_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$;

each $R_3$ is independently selected from the group consisting of H, deuterium, halogen, cyano, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, —$C_{0-8}$—$S(O)_rR_{10}$, —$C_{0-8}$—$O$—$R_{11}$, —$C_{0-8}$—$C(O)OR_{12}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$;

each $R_4$ is independently selected from the group consisting of H, deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$;

$R_5$ and $R_6$ are each independently selected from the group consisting of H, deuterium, hydroxy, $C_{1-10}$ alkyl, $C_{1-10}$ alkoxy, $C_{2-10}$ alkenyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$, above groups are optionally further substituted by one or more substituents selected from the group consisting of deuterium, halogen, hydroxy, oxo, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$;

$R_7$ is selected from the group consisting of $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$;

$R_8$ and $R_9$ are each independently selected from the group consisting of deuterium, hydroxy, $C_{1-10}$ alkyl, $C_{3-10}$ cycloalkyl, 3-10 membered heterocyclyl, $C_{5-10}$ aryl, 5-10 membered heteroaryl, —$S(O)_rR_{10}$, —$C(O)R_{12}$ and —$C(O)NR_{13}R_{14}$, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$, or, $R_8$ and $R_9$, together with the nitrogen atom directly attached thereto, form a 4-10 membered heterocyclyl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—$S(O)_rR_{10}$, —$C_{0-8}$—$O$—$R_{11}$, —$C_{0-8}$—$C(O)OR_{11}$, —$C_{0-8}$—$C(O)R_{12}$, —$C_{0-8}$—$O$—$C(O)R_{12}$, —$C_{0-8}$—$NR_{13}R_{14}$, —$C_{0-8}$—$C(=NR_{13})R_{12}$, —$C_{0-8}$—$N(R_{13})$—$C(=NR_{14})R_{12}$, —$C_{0-8}$—$C(O)NR_{13}R_{14}$ and —$C_{0-8}$—$N(R_{13})$—$C(O)R_{12}$;

each $R_{10}$ is selected from the group consisting of H, deuterium, hydroxy, $C_{1-10}$ alkyl, $C_{1-10}$ alkoxy, $C_{2-10}$ alkenyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —$NR_{13}R_{14}$, above groups are optionally further substituted by one or more substituents selected from the group consisting of deuterium, halogen, hydroxy, oxo, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$;

each $R_{11}$ is selected from the group consisting of H, deuterium, $C_{1-10}$ alkyl, $C_{2-10}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, oxo, cyano, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$;

each $R_{12}$ is selected from the group consisting of H, deuterium, hydroxy, $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —$NR_{13}R_{14}$;

$R_{13}$ and $R_{14}$ are each independently selected from the group consisting of H, deuterium, hydroxy. $C_{1-10}$ alkoxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-10}$ alkanoyl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy, amino, monoalkylamino, dialkylamino and $C_{1-10}$ alkanoyl, or, $R_{13}$ and $R_{14}$, together with the nitrogen atom directly attached thereto, form a 4-10 membered heterocyclyl or 4-10 membered heteroaryl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy, amino, monoalkylamino, dialkylamino and $C_{1-10}$ alkanoyl;

each r is independently 0, 1 or 2.

As a preferred embodiment, in the compound of formula (I), the stereoisomer, prodrug or pharmaceutically acceptable salt thereof, $R_1$ is selected from the group consisting of H, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$S(O)R_5$, —$S(O)_2R_6$ and —$C(O)R_7$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—$C(O)R_{12}$, —$C_{0-4}$—$NR_{13}R_{14}$, —$C_{0-4}$—$C(=NR_{13})R_{12}$, —$C_{0-4}$—$N(R_{13})$—$C(=NR_{14})R_{12}$, —$C_{0-4}$—$C(O)NR_{13}R_{14}$ and —$C_{0-4}$—$N(R_{13})$—$C(O)Ru$; $R_5$, $R_6$, $R_7$, $R_{10}$, $R_{11}$, $R_{12}$, $R_{13}$, $R_{14}$ and r are defined as in the compound of formula (I).

As a more preferred embodiment, in the compound of formula (I), the stereoisomer, prodrug or pharmaceutically acceptable salt thereof. $R_1$ is selected from the group consisting of H, deuterium, $C_{1-4}$ alkyl, allyl, $C_{3-6}$ cycloalkyl, 3-6 membered heterocyclyl, phenyl, diazole, triazol, methylsulfonyl, isopropylsulfonyl, aminosulfonyl, methoxycarbonyl, ethoxycarbonyl, acetyl, aninocarbonyl and dimethylaminocarbonyl, above groups are optionally further substituted by one or more substituents selected from the group consisting of deuterium, F, Cl, cyano, methyl, ethyl, $C_{3-6}$ cycloalkyl, 3-6 membered heterocyclyl, phenyl, methoxy, ethoxy, hydroxy, amino, isopropylamino, dimethylamino and diethyl amino.

As a preferred embodiment, in the compound of formula (I), the stereoisomer, prodrug or pharmaceutically acceptable salt thereof, each $R_4$ is independently selected from the group consisting of H, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$—, —$C_{0-4}$—O—$C(O)R_{12}$, —$C_{0-4}$—$NR_{13}R_{14}$, —$C_{0-4}$—$C(=NR_{13})R_{12}$, —$C_{0-4}$—$N(R_{13})$—$C(=NR_{14})R_{12}$, —$C_{0-4}$—$C(O)NR_{13}R_{14}$ and —$C_{0-4}$—$N(R_{13})$—$C(O)R_{12}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—$C(O)R_{12}$, —$C_{0-4}$—$NR_{13}R_{14}$, —$C_{0-4}$—$C(=NR_{13})R_{12}$, —$C_{0-4}$—$N(R_{13})$—$C(=NR_{14})R_{12}$, —$C_{0-4}$—$C(O)NR_{13}R_{14}$ and —$C_{0-4}$—$N(R_{13})$—$C(O)R_{12}$; $R_{10}$, $R_{11}$, $R_{12}$, $R_{13}$, $R_{14}$ and r are defined as in the compound of formula (I).

As a more preferred embodiment, in the compound of formula (I), the stereoisomer, prodrug or pharmaceutically acceptable salt thereof, each $R_4$ is independently selected from the group consisting of H, deuteriumi, halogen, cyano, nitro, azido, $C_{1-4}$ alkyl, allyl, acetenyl, $C_{3-6}$ cycloalkyl, oxacyclobutyl, azacyclopentyl, azacyclohexyl, phenyl, diazole, triazol, methylsulfonyl, isopropylsulfonyl, aminosulfonyl, hydroxy, methoxy, ethoxy, isopropoxy, methoxycarbonyl, ethoxycarbonyl, acetyl, acetoxy, acetoxymethyl, amino, dimethylamino and acetylamino, above groups are optionally further substituted by one or more substituents selected from the group consisting of deuterium, F, Cl, cyano, methyl, ethyl, cyclopropyl, phenyl, methoxy, ethoxy, hydroxy and amino.

As a preferred embodiment, in the compound of formula (I), the stereoisomer, prodrug or pharmaceutically acceptable salt thereof, each $R_3$ is independently selected from the group consisting of H, deuterium, halogen, cyano, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—$S(O)_rR_{10}$, —$C_{0-4}$—O—$R_{11}$, —$C_{0-4}$—$C(O)OR_{11}$, —$C_{0-4}$—$C(O)R_{12}$, —$C_{0-4}$—O—$C(O)R_{12}$, —$C_{0-4}$—$NR_{13}R_{14}$, —$C_{0-4}$—$C(=NR_{13})R_{12}$, —$C_{0-4}$—$N(R_{13})$—$C(=NR_{14})R_{12}$, —$C_{0-4}$—$C(O)NR_{13}R_{14}$ and —$C_{0-4}$—$N(R_{13})$—$C(O)R_{12}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —$C_{0-4}$—$S(O)_rR_{10}$, —$C_{0-4}$—O—$R_{11}$, —$C_{0-4}$—$C(O)OR_{12}$, —$C_{0-4}$—$C(O)R_{12}$, —$C_{0-4}$—O—$C(O)R_{12}$, —$C_{0-4}$—$NR_{13}R_{14}$, —$C_{0-4}$—$C(=NR_{13})R_{12}$, —$C_{0-4}$—$N(R_{13})$—$C(=NR_{14})R_{12}$, —$C_{0-4}$—$C(O)NR_{13}R_{14}$ and —$C_{0-4}$—$N(R_{13})$—$C(O)R_{12}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—$S(O)_rR_{10}$, —$C_{0-4}$—O—$R_{11}$, —$C_{0-4}$—$C(O)OR_{11}$, —$C_{0-4}$—$C(O)$ R₁₂, —C₀₋₄—O—C(O)R₁₂, —C₀₋₄—NR₁₃R₁₄, —C₀₋₄—C(=NR₁₃)R₁₂, —C₀₋₄—N(R₁₃)—C(=NR₁₄)R₁₂, —C₀₋₄—C(O)NR₁₃R₁₄ and —C₀₋₄—N(R₁₃)—C(O)R₁₂; R₁₀, R₁₁, R₁₂, R₁₃, R₁₄ and r are defined as in the compound of formula (I).

As a preferred embodiment, in the compound of formula (I), the stereoisomer, prodrug or pharmaceutically acceptable salt thereof, R₂ is C₅₋₈ aryl or 5-8 membered heteroaryl, above groups are optionally further substituted by one or more substituents selected from the group consisting of deuterium, halogen, cyano, nitro, azido, C₁₋₄ alkyl, C₂₋₄ alkenyl, C₂₋₄ alkynyl, C₃₋₈ cycloalkyl, 3-8 membered heterocyclyl, C₅₋₈ aryl, 5-8 membered heteroaryl, =O, —C₀₋₄—S(O)ᵣR₁₀, —C₀₋₄—O—R₁₁, —C₀₋₄—C(O)OR₁₁, —C₀₋₄—C(O)R₁₂, —C₀₋₄—O—C(O)R₁₂, —C₀₋₄—NR₁₃R₁₄, —C₀₋₄—C(=NR₁₃)R₁₂, —C₀₋₄—N(R₁₃)—C(=NR₁₄)R₁₂, —C₀₋₄—C(O)NR₁₃R₁₄ and —C₀₋₄—N(R₁₃)—C(O)R₁₂, above groups are optionally more further substituted by one or more substituents selected from the group consisting of deuterium, halogen, cyano, nitro, azido, C₁₋₄ alkyl, C₂₋₄ alkenyl, C₂₋₄ alkynyl, C₁₋₄ haloalkyl, C₁₋₄ deuterioalkyl, C₃₋₈ cycloalkyl, 3-8 membered heterocyclyl, C₅₋₈ aryl, 5-8 membered heteroaryl, =O, —R₁₁, —C₀₋₄—S(O)ᵣR₁₀, —C₀₋₄—O—R₁₁, —C₀₋₄—C(O)OR₁₁, —C₀₋₄—C(O)R₁₂, —C₀₋₄—O—C(O)R₁₂, —C₀₋₄—NR₁₃R₁₄, —C₀₋₄—C(=NR₁₃)R₁₂, —C₀₋₄—N(R₁₃)—C(=NR₁₄)R₁₂, —C₀₋₄—C(O)NR₁₃R₁₄ and —C₀₋₄—N(R₁₃)—C(O)R₁₂; R₁₀, R₁₁, R₁₂, R₁₃, R₁₄ and r are defined as in the compound of formula (I).

As a more preferred embodiment, in the compound of formula (I), the stereoisomer, prodrug or pharmaceutically acceptable salt thereof, R₂ is phenyl or 5-6 membered heteroaryl, above groups are optionally further substituted by one or more substituents selected from the group consisting of deuterium, halogen, cyano, C₁₋₄ alkyl, C₃₋₆ cycloalkyl, 3-6 membered heterocyclyl, C₅₋₆ aryl, 5-6 membered heteroaryl, =O, —S(O)ᵣR₁₀, —O—R₁₁, —C(O)OR₁₁, —C(O)R₁₂, —O—C(O)R₁₂, —NR₁₃R₁₄, —C(O)NR₁₃R₁₄ and —N(R₁₃)—C(O)R₁₂, above groups are optionally more further substituted by one or more substituents selected from the group consisting of deuterium, halogen, cyano, C₁₋₄ alkyl, C₁₋₄ haloalkyl, C₁₋₄ deuterioalkyl, C₃₋₈ cycloalkyl, 3-8 membered heterocyclyl, phenyl, 5-6 membered heteroaryl, =O, —S(O)ᵣR₁₀, —O—R₁₁, —C(O)OR₁₁, —C(O)R₁₂, —O—C(O)R₁₂, —NR₁₃R₁₄, —C(O)NR₁₃R₁₄ and —N(R₁₃)—C(O)R₁₂; R₁₀, R₁₁, R₁₂, R₁₃, R₁₄ and r are defined as in the compound of formula (I).

As a more preferred embodiment, in the compound of formula (I), the stereoisomer, prodrug or pharmaceutically acceptable salt thereof, R₂ is phenyl or 5-6 membered heteroaryl, the 5-6 membered heteroaryl is selected from pyridyl, pyrimidinyl, pyridazinyl, pyrazinyl, 1,3,5-triazinyl, pyrrolyl, pyrazolyl, inidazolyl, triazol and thiazolyl, above groups are optionally further substituted by one or more substituents selected from the group consisting of deuterium, halogen, cyano, C₁₋₄ alkyl, C₃₋₆ cycloalkyl, 3-8 membered heterocyclyl, —S(O)ᵣR₁₀, —O—R₁₁, —C(O)OR₁₁, —NR₁₃R₁₄, —C(O)NR₁₃R₁₄ and —N(R₁₃)—C(O)R₁₂, above groups are optionally more further substituted by one or more substituents selected from the group consisting of deuterium, halogen, cyano, C₁₋₄ alkyl, C₁₋₄ haloalkyl, C₁₋₄ deuterioalkyl, C₃₋₈ cycloalkyl, 3-8 membered heterocyclyl, =O, —S(O)ᵣR₁₀, —O—R₁₁ and —NR₁₃R₁₄; R₁₀, R₁₁, R₁₂, R₁₃, R₁₄ and r are defined as in the compound of formula (I).

As a more preferred embodiment, in the compound of formula (I), the stereoisomer, prodrug or pharmaceutically acceptable salt thereof, the compound of formula (I) is a compound having formula (II):

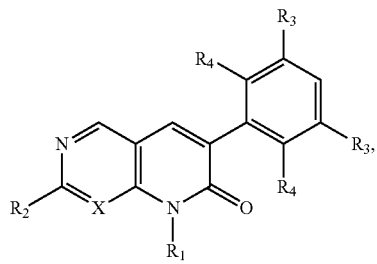

(II)

wherein, X is CH or N;

R₁ is selected from the group consisting of H, deuterium, C₁₋₄ alkyl, C₃₋₆ cycloalkyl, 3-6 membered heterocyclyl, methylsulfonyl and aminosulfonyl, above groups are optionally further substituted by one or more substituents selected from the group consisting of deuterium, F, Cl, cyano, methyl, ethyl, C₃₋₆ cycloalkyl, 3-6 membered heterocyclyl, phenyl, methoxy, ethoxy, hydroxy, amino, isopropylamino, dimethylamino and diethyl amino;

R₂ is phenyl or 5-6 membered heteroaryl, the 5-6 membered heteroaryl is selected from the group consisting of pyridyl, pyrazolyl, imidazolyl and thiazolyl, above groups are optionally further substituted by one or more substituents selected from the group consisting of deuterium, halogen, cyano, hydroxy, C₁₋₄ alkyl, C₁₋₄ alkoxy, C₃₋₆ cycloalkyl, 3-8 membered heterocyclyl, —NR₁₃R₁₄ and —C(O)NR₁₃R₁₄, above groups are optionally more further substituted by one or more substituents selected from the group consisting of deuterium, halogen, cyano, hydroxy, C₁₋₄ alkoxy, C₁₋₄ alkyl, C₁₋₄ haloalkyl, C₁₋₄ deuterioalkyl, C₃₋₈ cycloalkyl, 3-8 membered heterocyclyl, —S(O)ᵣR₁₀ and —NR₁₃R₁₄;

each R₃ is independently selected from the group consisting of H, deuterium, halogen, cyano, C₁₋₄ alkyl, C₃₋₆ cycloalkyl, oxacyclobutyl, azacyclopentyl, azacyclohexyl, hydroxy, methoxy, ethoxy and isopropoxy, above groups are optionally further substituted by one or more substituents selected from the group consisting of deuterium, halogen, cyano, C₁₋₄ alkyl, trifluoromethyl, difluoromethyl, trideuteriomethyl, dideuteriomethyl, cyclopropyl, oxacyclobutyl, methoxy, ethoxy, hydroxy and carboxy;

each R₄ is independently selected from the group consisting of H, deuterium, F, Cl, cyano, C₁₋₄ alkyl, C₃₋₆ cycloalkyl, oxacyclobutyl, azacyclopentyl, azacyclohexyl, hydroxy, methoxy, ethoxy and isopropoxy, above groups are optionally further substituted by one or more substituents selected from the group consisting of deuterium, F, Cl, cyano, methyl, ethyl, cyclopropyl, methoxy, ethoxy and hydroxy;

R₁₀, R₁₃, R₁₄ and r are defined as in the compound of formula (I).

As a more preferred embodiment, in the compound of formula (I), the stereoisomer, prodrug or pharmaceutically acceptable salt thereof, each R₁₀ is selected from the group consisting of H, deuterium, hydroxy. C₁₋₄ alkyl, C₁₋₄ alkoxy, C₂₋₄ alkenyl, C₃₋₈ cycloalkyl, C₃₋₈ cycloalkoxy, 3-8 membered heterocyclyl, 3-8 membered heterocyclyloxy, C₅₋₈ aryl, C₅₋₈ aryloxy, 5-8 membered heteroaryl, 5-8 membered heteroaryloxy and —NR₁₃R₁₄, above groups are optionally further substituted by one or more substituents selected from the group consisting of deuterium, halogen, hydroxy, oxo, $C_{1-4}$ alkyl, $C_{1-4}$ alkoxy, $C_{3-8}$ cycloalkyl, $C_{3-8}$ cycloalkoxy, 3-8 membered heterocyclyl, 3-8 membered heterocyclyloxy. $C_{5-8}$ aryl, $C_{5-8}$ aryloxy, 5-8 membered heteroaryl, 5-8 membered heteroaryloxy and —$NR_{13}R_{14}$;

- $R_{13}$ and $R_{14}$ are each independently selected from H, deuterium, hydroxy, $C_{1-4}$ alkoxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-4}$ alkanoyl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-8}$ cycloalkyl, $C_{3-8}$ cycloalkoxy, 3-8 membered heterocyclyl, 3-8 membered heterocyclyloxy. $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl,
- or, $R_{13}$ and $R_{14}$, together with the nitrogen atom directly attached thereto, form a 4-8 membered heterocyclyl or 4-8 membered heteroaryl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy. $C_{3-8}$ cycloalkyl, $C_{3-8}$ cycloalkoxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl;

each r is independently 0, 1 or 2.

As the most preferred embodiment, the compound of formula (I), the stereoisomer, prodrug or pharmaceutically acceptable salt thereof includes, but is not limited to, the following compounds:

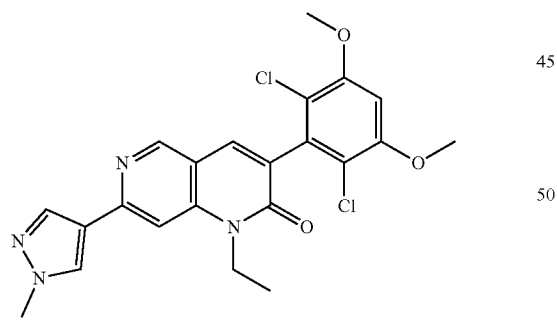

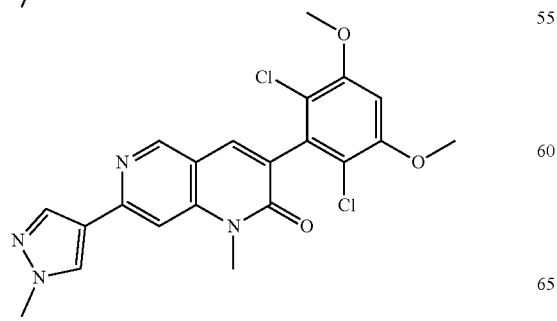

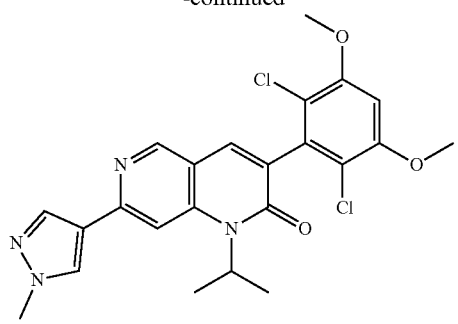

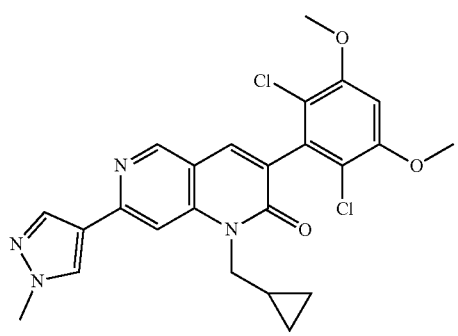

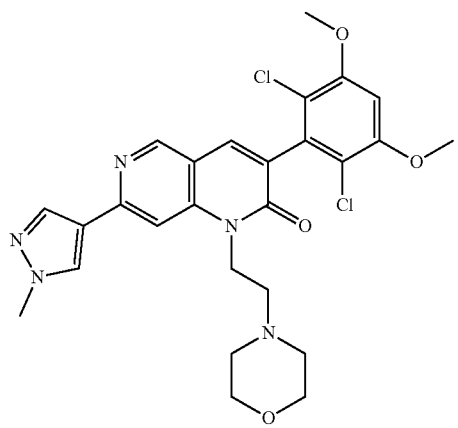 [SMILES: COc1cc(OC)c(Cl)c(-c2cc3cnc(-c4cnn(C)c4)cc3n(CCN3CCOCC3)c2=O)c1Cl]

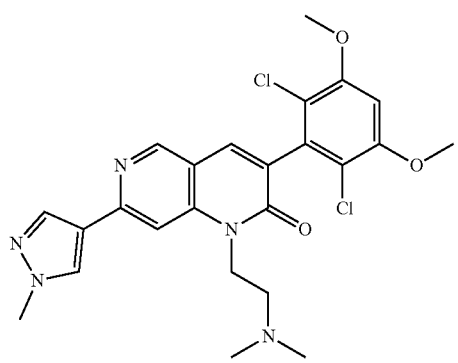 [SMILES: COc1cc(OC)c(Cl)c(-c2cc3cnc(-c4cnn(C)c4)cc3n(CCN(C)C)c2=O)c1Cl]

-continued
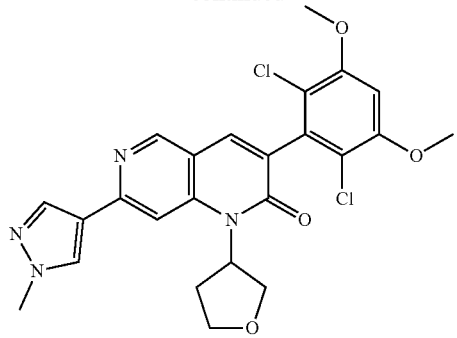
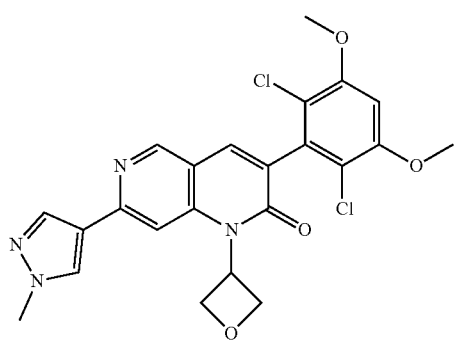 [SMILES: COc1cc(OC)c(Cl)c(-c2cc3cnc(-c4cnn(C)c4)cc3n(C3COC3)c2=O)c1Cl]
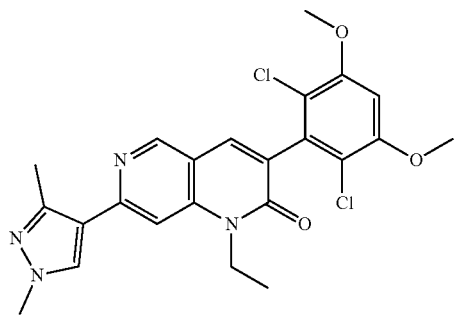 [SMILES: CCn1c(=O)c(-c2c(Cl)c(OC)cc(OC)c2Cl)cc2cnc(-c3cn(C)nc3C)cc21]
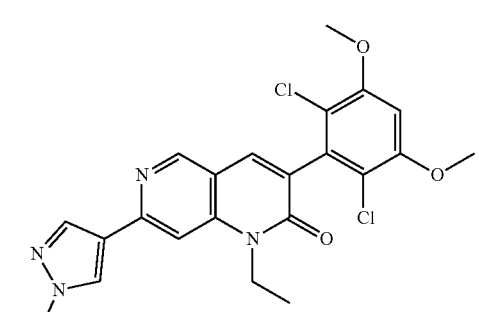
-continued
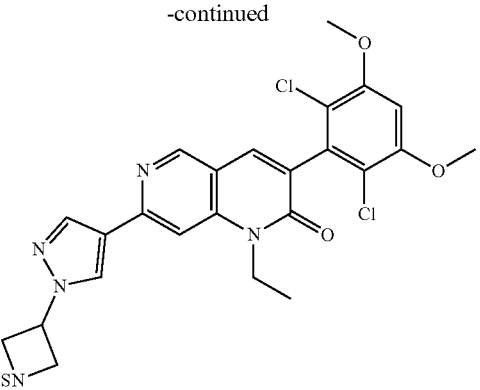
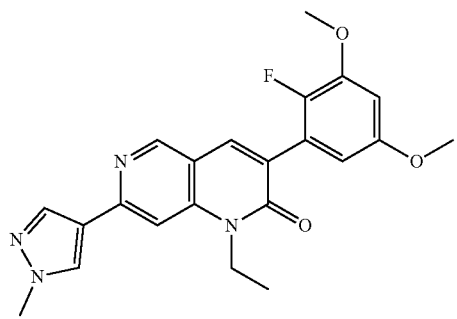

13
-continued
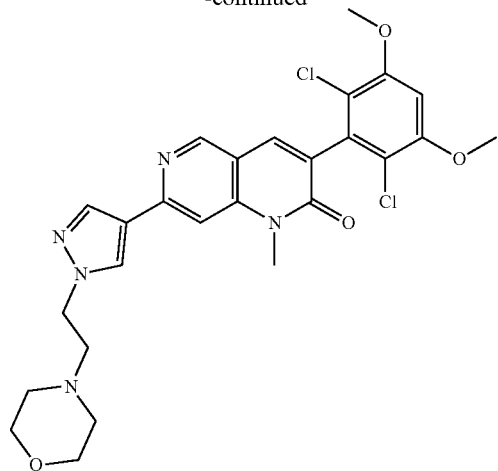
14
-continued
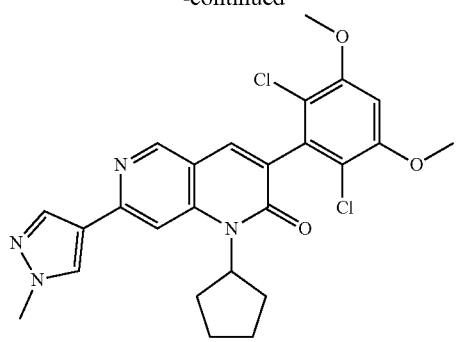
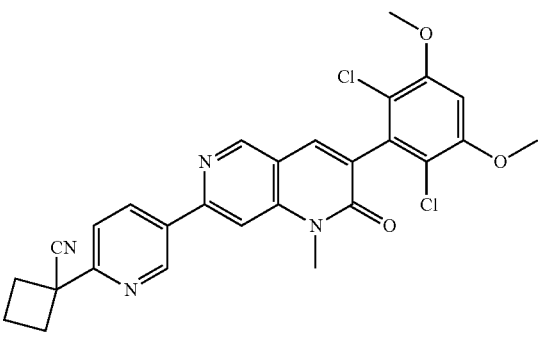 [SMILES: COc1cc(OC)c(Cl)c(-c2cc3cnc(-c4ccc(C5(C#N)CCC5)nc4)cc3n(C)c2=O)c1Cl]
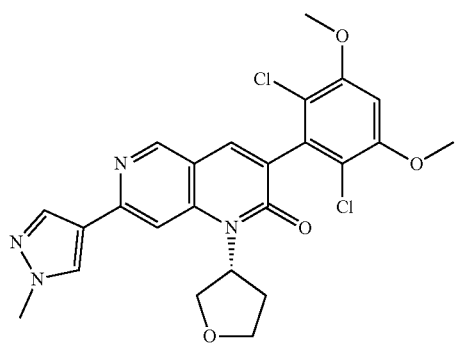 [SMILES: COc1cc(OC)c(Cl)c(-c2cc3cnc(-c4cnn(C)c4)cc3n([C@H]3CCOC3)c2=O)c1Cl]
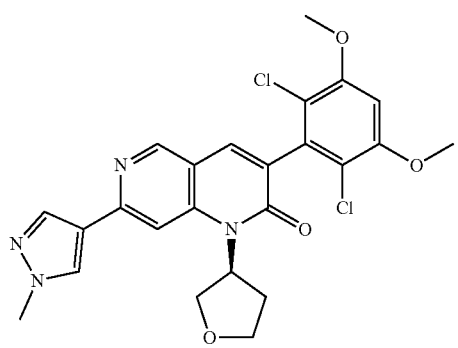 [SMILES: COc1cc(OC)c(Cl)c(-c2cc3cnc(-c4cnn(C)c4)cc3n([C@H]3CCOC3)c2=O)c1Cl]

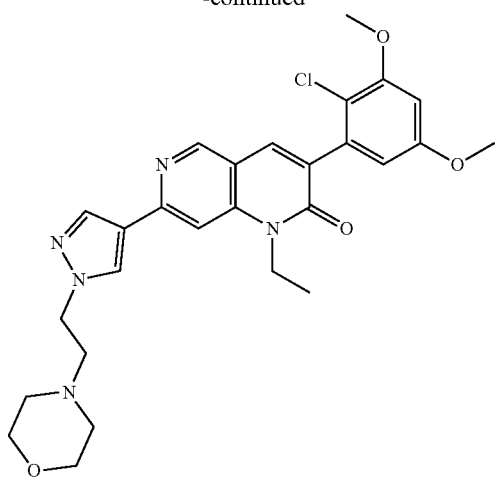
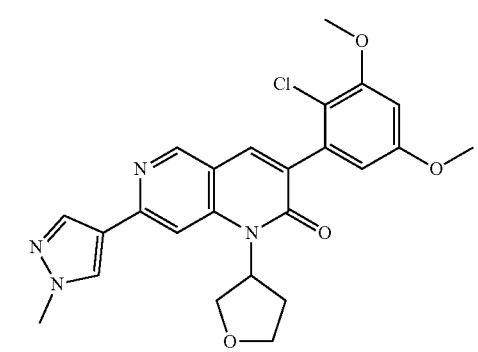 [SMILES: COc1cc(OC)c(Cl)c(-c2cc3cnc(-c4cnn(C)c4)cc3n(C3CCOC3)c2=O)c1]
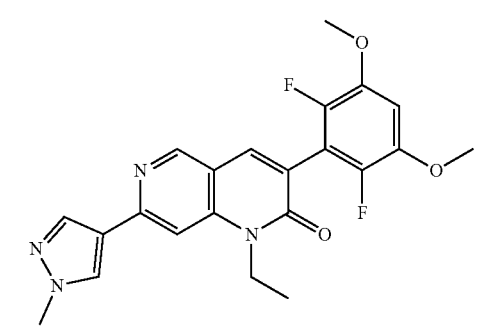 [SMILES: CCn1c(=O)c(-c2c(F)c(OC)cc(OC)c2F)cc2cnc(-c3cnn(C)c3)cc21]
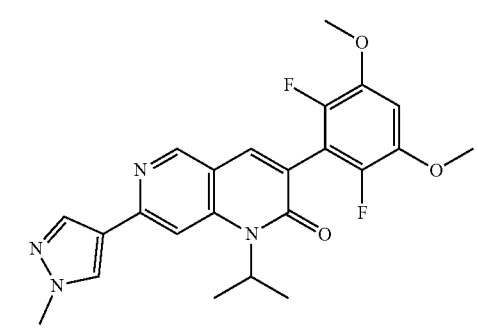 [SMILES: COc1cc(OC)c(F)c(-c2cc3cnc(-c4cnn(C)c4)cc3n(C(C)C)c2=O)c1F]
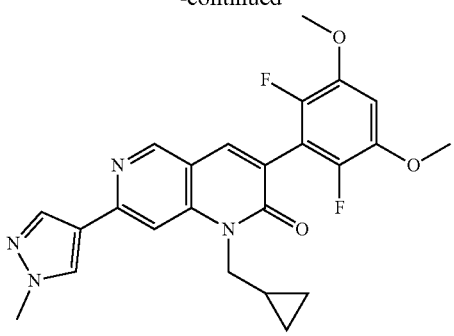
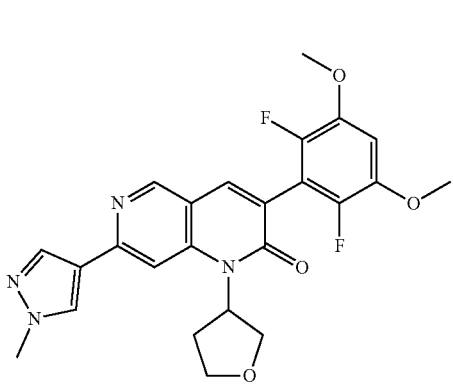 [SMILES: COc1cc(OC)c(F)c(-c2cc3cnc(-c4cnn(C)c4)cc3n(C3CCOC3)c2=O)c1F]
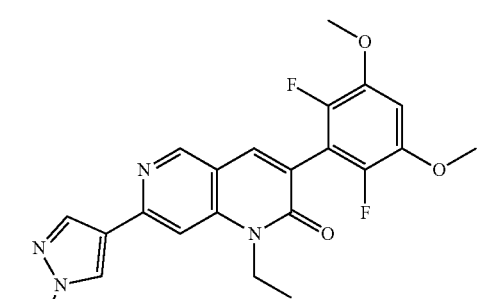
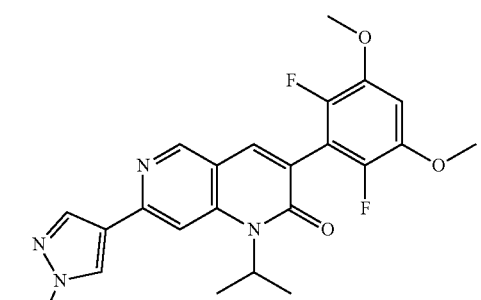

17
-continued
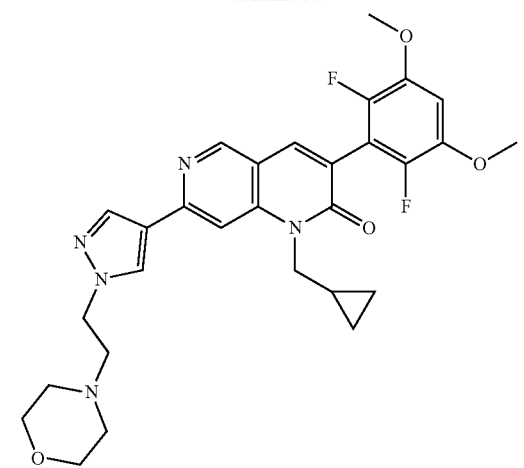 [SMILES: COc1cc(OC)c(F)c(-c2cc3cnc(-c4cnn(CCN5CCOCC5)c4)cc3n(CC3CC3)c2=O)c1F]
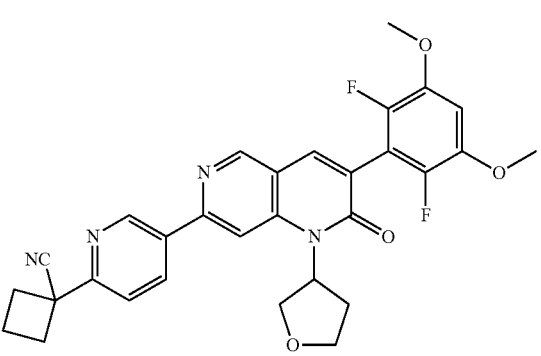 [SMILES: COc1cc(OC)c(F)c(-c2cc3cnc(-c4ccc(C5(C#N)CCC5)nc4)cc3n(C3CCOC3)c2=O)c1F]
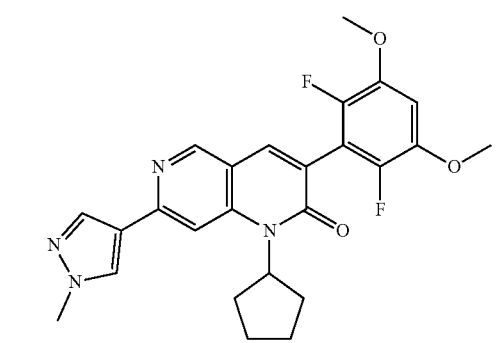 [SMILES: COc1cc(OC)c(F)c(-c2cc3cnc(-c4cnn(C)c4)cc3n(C3CCCC3)c2=O)c1F]
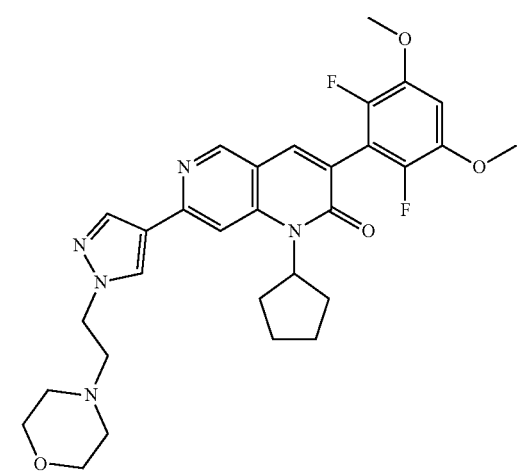 [SMILES: COc1cc(OC)c(F)c(-c2cc3cnc(-c4cnn(CCN5CCOCC5)c4)cc3n(C3CCCC3)c2=O)c1F]
18
-continued
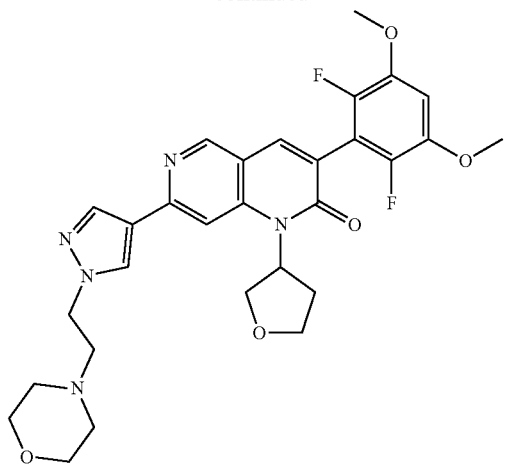 [SMILES: COc1cc(OC)c(F)c(-c2cc3cnc(-c4cnn(CCN5CCOCC5)c4)cc3n(C3CCOC3)c2=O)c1F]
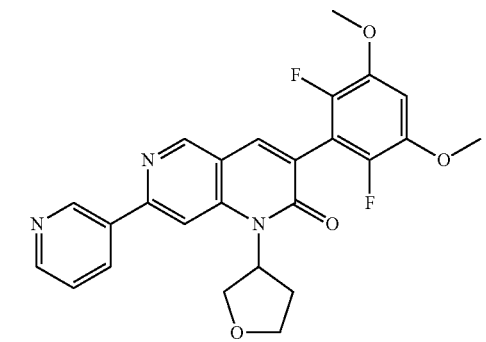 [SMILES: COc1cc(OC)c(F)c(-c2cc3cnc(-c4cccnc4)cc3n(C3CCOC3)c2=O)c1F]
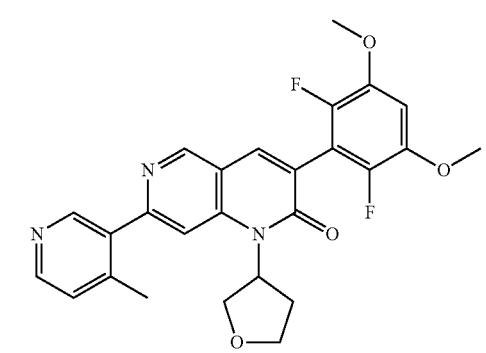 [SMILES: COc1cc(OC)c(F)c(-c2cc3cnc(-c4cnccc4C)cc3n(C3CCOC3)c2=O)c1F]
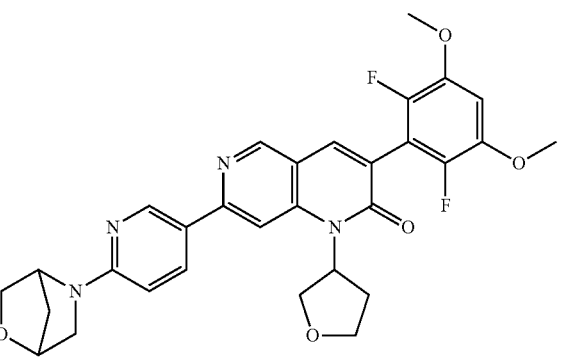 [SMILES: COc1cc(OC)c(F)c(-c2cc3cnc(-c4ccc(N5CC6CC5CO6)nc4)cc3n(C3CCOC3)c2=O)c1F]

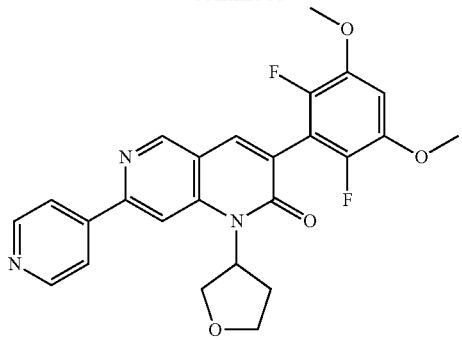
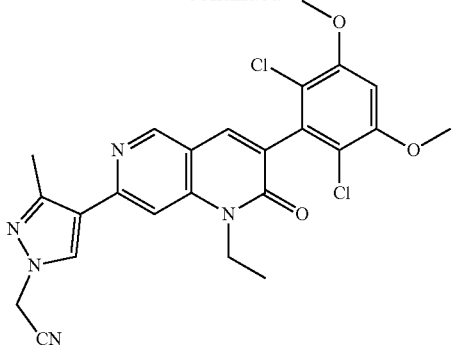 [SMILES: CCn1c(=O)c(-c2c(Cl)c(OC)cc(OC)c2Cl)cc2cnc(-c3cn(CC#N)nc3C)cc21]
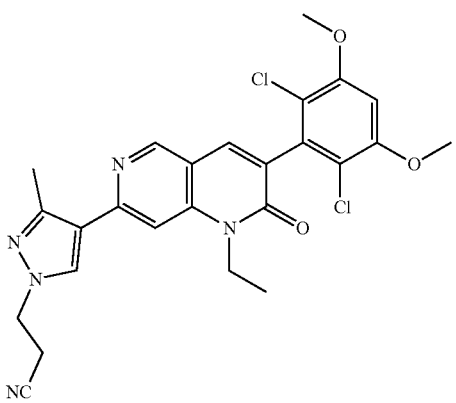 [SMILES: CCn1c(=O)c(-c2c(Cl)c(OC)cc(OC)c2Cl)cc2cnc(-c3cn(CCC#N)nc3C)cc21]
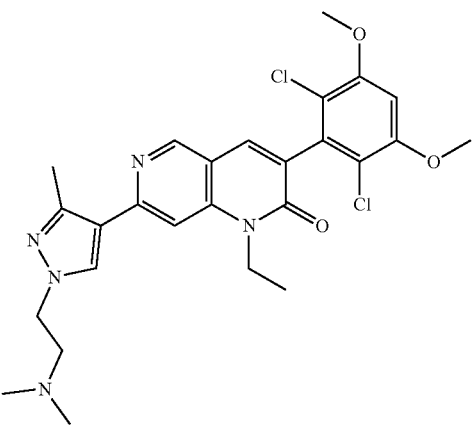
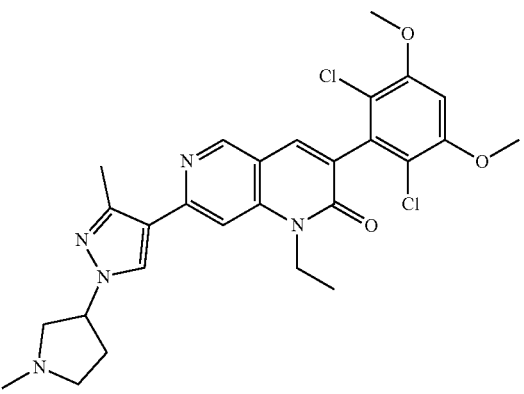

21
-continued
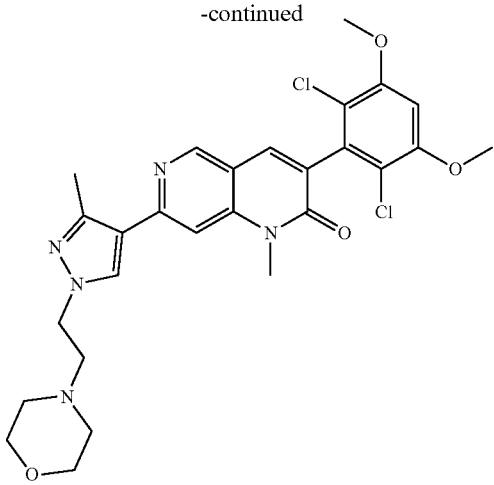
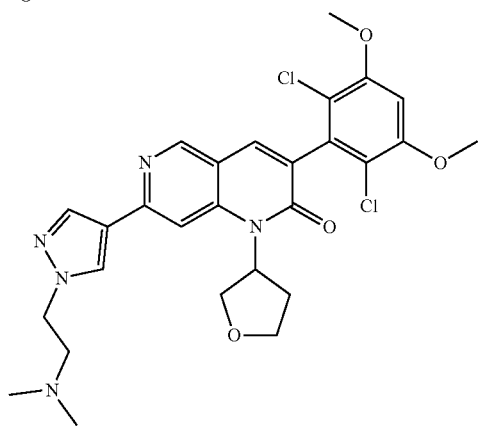
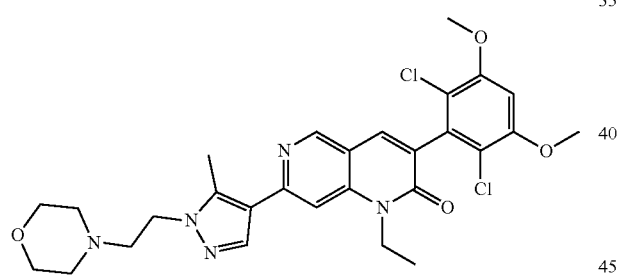
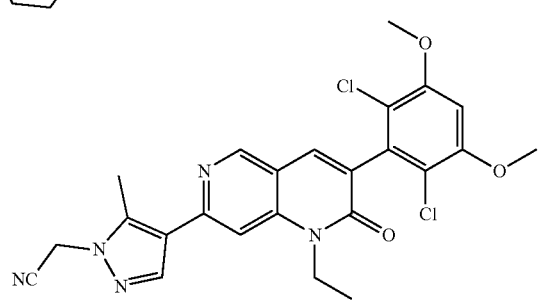
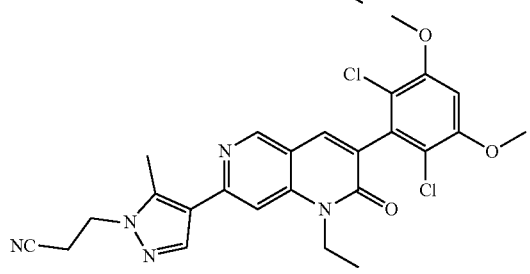
or
22
-continued
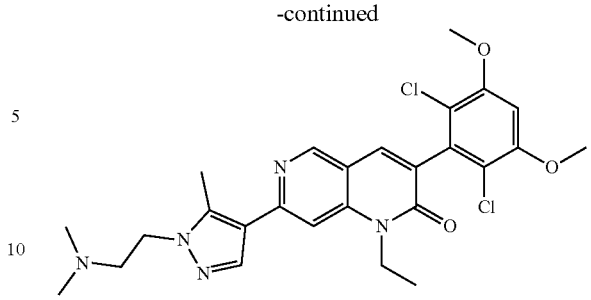
The second aspect of the invention provides a process for preparing the compound of formula (I), the stereoisomer, prodrug or pharmaceutically acceptable salt thereof, comprising the following steps:
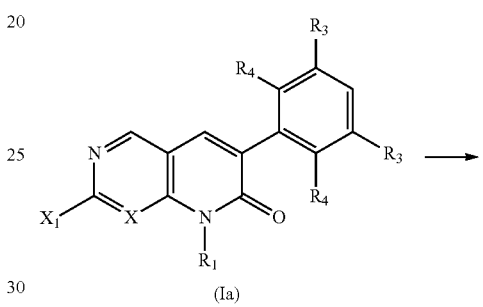
(Ia)
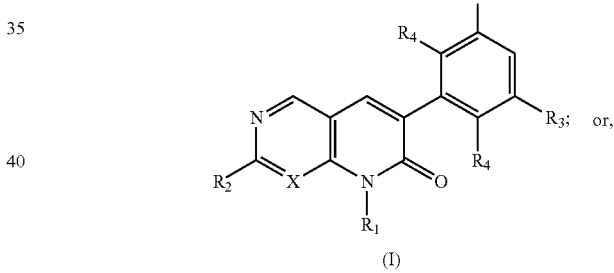
(I)
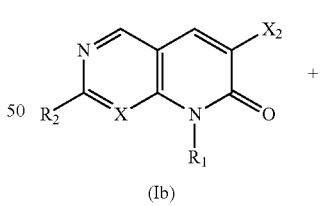
(Ib)
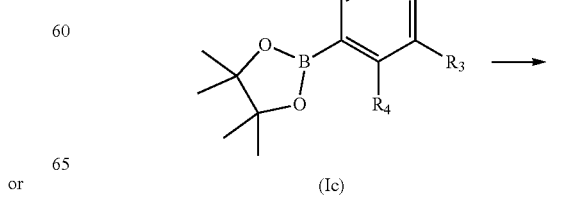
(Ic)

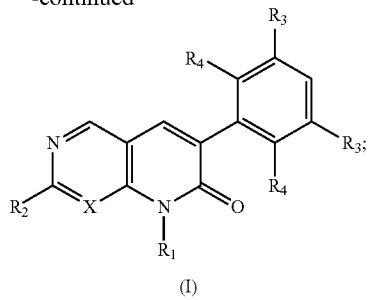

(I)

wherein, $X_1$, $X_2$ are each independently Cl or Br; X, $R_1$, $R_2$, $R_3$ and $R_4$ are defined as in the compound of formula (I).

The third aspect of the present invention provides a pharmaceutical composition comprising the above compound of formula (I), the stereoisomer, prodrug or pharmaceutically acceptable salt thereof, and pharmaceutically acceptable carrier.

The fourth aspect of the present invention provides the application of the above compound of formula (I), the stereoisomer, prodrug or pharmaceutically acceptable salt thereof in the preparation of medicament for the treatment of tumor or cancer.

As a preferred embodiment, the tumor or cancer is selected from bladder cancer, breast cancer, cervical cancer, colorectal cancer, endometrial cancer, gastric cancer, head and neck cancer, renal carcinoma, hepatic carcinoma, lung cancer, ovarian cancer, prostate cancer, esophageal cancer, gallbladder cancer, pancreatic cancer, thyroid cancer, skin cancer, leukemia, multiple myeloma, chronic lymphocytic lymphoma, adult T cell leukemia, B cell lymphoma, acute myelocytic leukemia, Hodgkin lymphoma or non-Hodgkin lymphoma, Waldenstrom macroglobulinemia, hairy cell lymphoma, cell lymphoma, Bunkitt's lymphoma, glioblastoma, melanoma and rhabdomyosarcoma.

The fifth aspect of the present invention provides the applications of the above compound of formula (I), the stereoisomer, prodrug or pharmaceutically acceptable salt thereof in the preparation of medicament for the treatment of myeloproliferative disease, skeleton or cartilage cell disorder, and hypophosphatemia.

As a preferred embodiment, the myeloproliferative disease is selected from polycythemia, primary thrombocytosis or primary myelofibrosis; the skeleton or cartilage cell disorder is selected from dysplasia, dyschondroplasia, dwarfism, thanatophoric dysplasia (TD), Apert's syndrome, Crouzon syndrome, Jackson-Weiss syndrome, Beare-Stevenson cutis gyrata syndrome, Pfeiffer syndrome or cranial muscular atrophy syndrome; the hypophosphatemia is selected from X-linked hypophosphatemic rickets, autosomal recessive hypophosphatemic rickets, autosomal dominant hypophosphatemic rickets and tumor induced oothecomalacia.

The sixth aspect of the present invention provides the compound of formula (I), the stereoisomer, prodrug or pharmaceutically acceptable salt thereof or the pharmaceutical composition for use as a selective FGFR inhibitor for the treatment of diseases related to the aberrant expression/mutation of FGFR or the aberrant expression/activity of corresponding ligand(s).

DETAILED DESCRIPTION OF THE INVENTION

After an extensive and intensive research, the inventor of the present invention developed an FGFR inhibitor of structure as shown in formula (I), preparation method therefor and application thereof for the first time. The substituents are defined as and described in the specification and the claims. The series of compounds in this invention can be widely used for developing a promising new generation of FGFR inhibitor medicament for treating tumor, cancer, myeloproliferative disease, skeleton or cartilage cell disorder, and/or hypophosphatemia. On such basis, the present invention has been completed.

Detailed description: Unless otherwise stated, the following terms used in the specification and claims have the following meanings.

"Alkyl" refers to a straight or branched saturated aliphatic hydrocarbon group, for example, "$C_{1-8}$ alkyl" refers to a straight or branched alkyl having 1 to 8 carbon atoms, including but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof and so on.

The alkyl can optionally be either a substituted or unsubstituted one; if it is a substituted one, the substituents can preferably be one or more (preferably 1, 2, 3 or 4) of the following groups, and independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $—C_{0-8}—S(O)_rR_{10}$, $—C_{0-8}—O—R_{11}$, $—C_{0-8}—C(O)OR_{11}$, $—C_{0-8}—C(O)R_{12}$, $—C_{0-8}—O—C(O)R_{12}$, $—C_{0-8}—NR_{13}R_{14}$, $—C_{0-8}—C(=NR_{13})R_{12}$, $—C_{0-8}—N(R_{13})—C(=NR_4)R_{12}$, $—C_{0-8}—C(O)NR_{13}R_{14}$ and $—C_{0-8}—N(R_{13})—C(O)R_{12}$.

"Cycloalkyl" refers to a saturated or partially unsaturated monocyclic or polycyclic hydrocarbon substituent, for example, "$C_{3-10}$ cycloalkyl" refers to a cycloalkyl having 3-10 carbon atoms, which may be a monocyclic cycloalky and a polycyclic cycloalkyl, wherein, monocyclic cycloalkyl includes, but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and the like;

and polycyclic cycloalkyl includes spiro, fused, and bridged cycloalkyls. "Spirocycloalkyl" refers to a polycyclic group that shares a carbon atom (called a spiro atom) between the monocyclic rings. These groups may contain one or more (preferably 1, 2 or 3) double bonds, but none of the rings have a fully conjugated i-electron system. The spirocycloalkyl may be a monospirocycloalkyl, a bispirocycloalkyl or a polyspirocycloalkyl according to the number of common spiro atoms between the rings, spirocycloalkyl includes, but is not limited to:

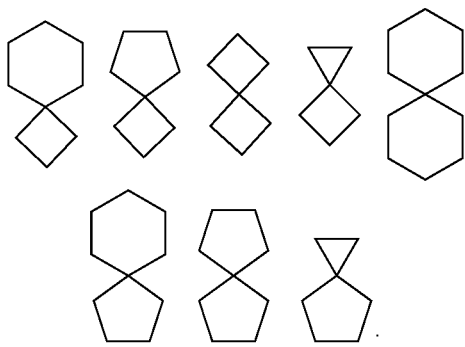

"Fused cycloalkyl" refers to an all-carbon polycyclic group in which each ring shares an adjacent pair of carbon atoms with other rings in the system, wherein one or more (preferably 1 or 2) of the rings may contain one or more (preferably 1, 2 or 3) double bonds, but none of the rings have a fully conjugated n-electron system. Depending on the number of rings, it may be bicyclic, tricyclic, tetracyclic or polycyclic, fused cycloalkyl includes but is not limited to:

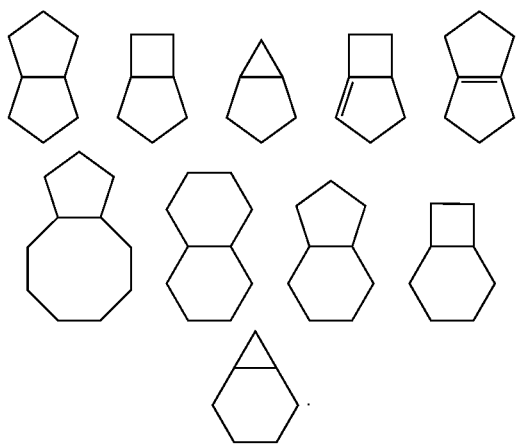

"Bridged cycloalkyl" refers to an all-carbon polycyclic group in which any two rings share two carbon atoms that are not directly bonded, which may contain one or more (preferably 1, 2 or 3) double bonds, but none of the rings have a fully conjugated n-electron system. Depending on the number of rings, it may be bicyclic, tricyclic, tetracyclic or polycyclic, bridged cycloalkyl includes but is not limited to: Depending on the number of rings, it may be bicyclic, tricyclic, tetracyclic or polycyclic, fused cycloalkyl includes but is not limited to:

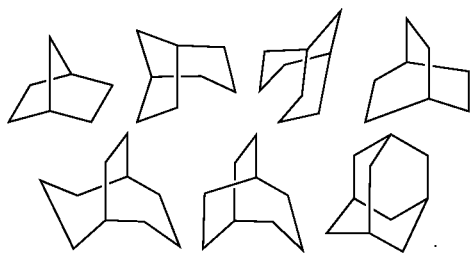

The ring of the cycloalkyl may be fused to a ring of aryl, heteroaryl or heterocycloalkyl, wherein the ring attached to the parent structure is a cycloalkyl, includes, but is not limited to indanyl, tetrahydronaphthyl, benzocycloheptyl and the likes.

The cycloalkyl can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_{10}$, $-C_{0-8}-O-R_{11}$, $-C_{0-8}-C(O)R_{11}$, $-C_{0-8}-C(O)R_{12}$, $-C_{0-8}-O-C(O)R_{12}$, $-C_{0-8}-NR_{13}R_{14}$, $-C_{0-8}-C(=NR_{13})R_{12}$, $-C_{0-8}-N(R_{13})-C(=NR_{14})R_{12}$, $-C_{0-8}-C(O)NR_{13}R_{14}$ and $-C_{0-8}-N(R_{13})-C(O)R_{12}$.

"Heterocyclyl" refers to a saturated or partially unsaturated monocyclic or polycyclic cyclic hydrocarbon substituent wherein one or more (preferably 1, 2, 3 or 4) of the ring atoms are heteroatoms selected from nitrogen, oxygen or $S(O)_r$ (wherein r is an integer of 0, 1, 2), but excluding ring moiety of —O—O—, —O—S— or —S—S—, and the remaining ring atoms are carbon atoms. For example, "5-10 membered heterocyclyl" refers to a cyclic group containing 5 to 10 ring atoms, and "3-10 membered heterocyclyl" refers to a cyclic group containing 3 to 10 ring atoms.

Monocyclic heterocyclyl includes, but is not limited to pyrrolidinyl, piperidinyl, piperazinyl, morpholinyl, thiomorpholinyl, homopiperazinyl and the likes.

and polycyclic heterocyclyl includes spiro, fused, and bridged heterocyclyls. "Spiroheterocyclyl" refers to a polycyclic heterocyclyl that shares a carbon atom (called a spiro atom) between the monocyclic rings, wherein one or more (preferably 1, 2, 3 or 4) of the ring atoms are heteroatoms selected from nitrogen, oxygen or $S(O)_r$ (wherein r is an integer of 0, 1, 2), and the remaining ring atoms are carbon atoms. These groups may contain one or more (preferably 1, 2 or 3) double bonds, but none of the rings have a fully conjugated π-electron system. The spiroheterocyclyl may be a monospiroheterocyclyl, a bispiroheterocyclyl or a polyspiroheterocyclyl according to the number of common spiro atoms between the rings, spiroheterocyclyl includes, but is not limited to:

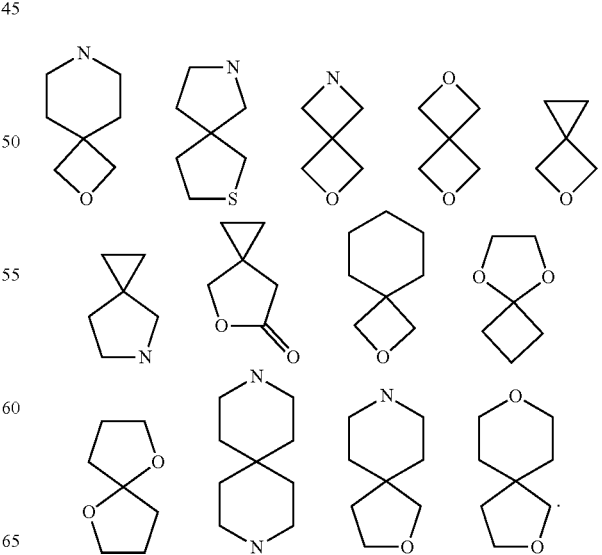

"Fused heterocyclyl" refers to a polycyclic heterocyclyl in which each ring shares an adjacent pair of carbon atoms with other rings in the system, wherein one or more (preferably 1 or 2) of the rings may contain one or more (preferably 1, 2 or 3) double bonds, but none of the rings have a fully conjugated π-electron system, wherein one or more (preferably 1, 2, 3 or 4) of the ring atoms are heteroatoms selected from nitrogen, oxygen or S(O)$_r$ (wherein r is an integer of 0, 1, 2), and the remaining ring atoms are carbon atoms. Depending on the number of rings, it may be bicyclic, tricyclic, tetracyclic or polycyclic, fused heterocyclyl includes, but is not limited to:

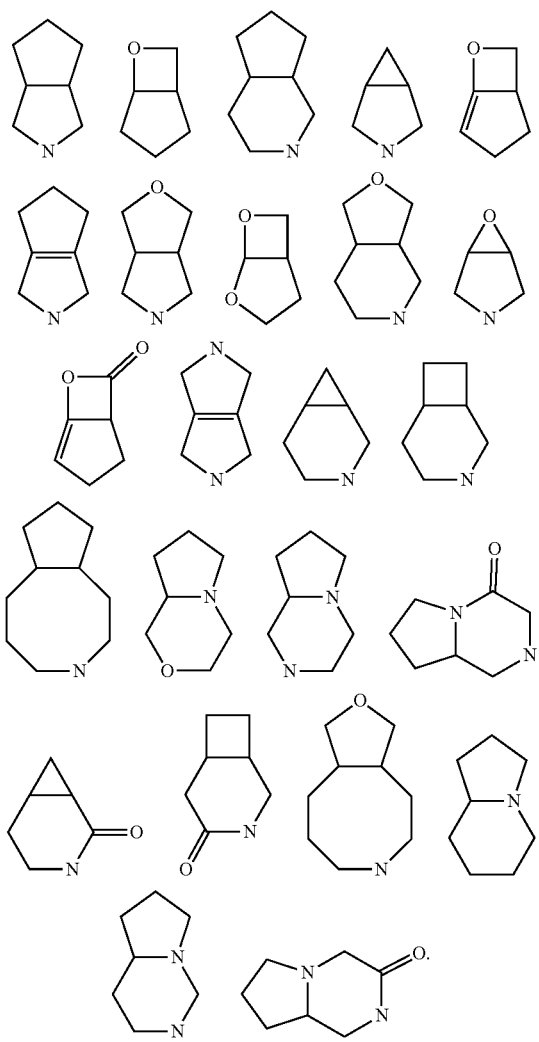

"Bridged heterocyclyl" refers to a polycyclic heterocyclyl in which any two rings share two carbon atoms that are not directly bonded, which may contain one or more (preferably 1, 2 or 3) double bonds, but none of the rings have a fully conjugated pi-electron system, wherein one or more (preferably 1, 2, 3 or 4) of the ring atoms are heteroatoms selected from nitrogen, oxygen or S(O)$_r$ (wherein r is an integer of 0, 1, 2), and the remaining ring atoms are carbon atoms. Depending on the number of rings, it may be bicyclic, tricyclic, tetracyclic or polycyclic, bridged heterocyclyl includes, but is not limited to:

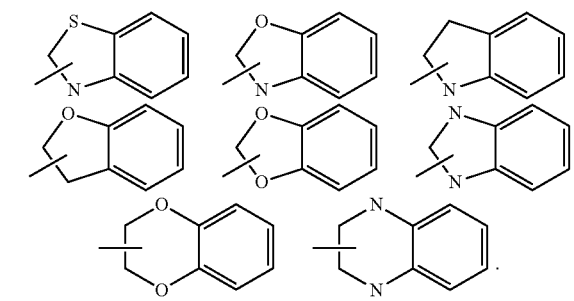

The ring of the heterocyclyl may be fused to a ring of aryl, heteroaryl or cycloalkyl wherein the ring attached to the parent structure is a heterocyclyl, includes, but is not limited to:

The heterocyclyl can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r R_{10}$, —$C_{0-8}$—O—$R_{11}$, —$C_{0-8}$—C(O)O$R_{11}$, —$C_{0-8}$—C(O)$R_{12}$, —$C_{0-8}$—O—C(O)$R_{12}$, —$C_{0-8}$—N$R_{13}R_{14}$, —$C_{0-8}$—C(=N$R_{13}$)$R_{12}$, —$C_{0-8}$—N($R_{13}$)—C(=N$R_{14}$)$R_{12}$, —$C_{0-8}$—C(O)N$R_{13}R_{14}$ and —$C_{0-8}$—N($R_{13}$)—C(O)$R_{12}$.

"Aryl" refers to an all-carbon monocyclic or fused polycyclic (ie, a ring that shares a pair of adjacent carbon atoms) group, and a polycyclic group having a conjugated π-electron system (i.e., a ring with adjacent pairs of carbon atoms), for example, "$C_{5-10}$ aryl" refers to an all-carbon aryl having 5-10 carbons, and "5-10 membered aryl" refers to an all-carbon aryl having 5-10 carbons, including but not limited to phenyl and naphthyl. The aryl ring may be fused to a ring of heteroaryl, heterocyclyl or cycloalkyl, wherein the ring attached to the parent structure is an aryl ring, includes, but is not limited to:

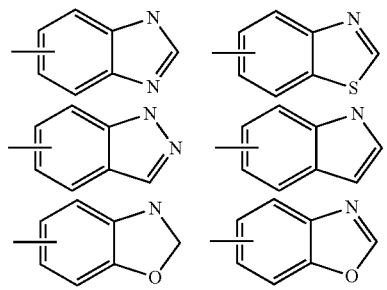

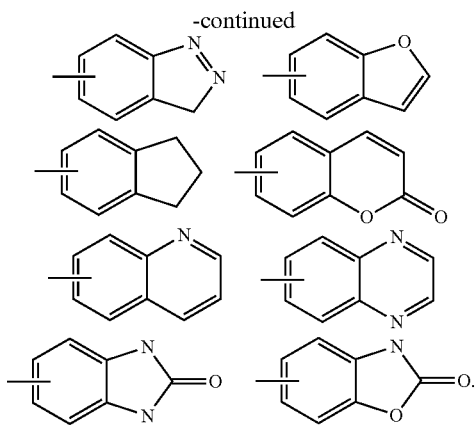

The aryl can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(RB)—C(O)R$_{12}$.

"Heteroaryl" refers to a heteroaromatic system containing 1 to 4 heteroatoms including a hetero atom selected from nitrogen, oxygen or S(O)$_r$ (wherein r is an integer of 0, 1, 2), for example, 5-8 membered heteroaryl refers to a heteroaromatic system containing 5 to 8 ring atoms, and 5-10 membered heteroaryl refers to a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl group or the like. The heteroaryl ring may be fused to a ring of aryl, heterocyclyl or cycloalkyl wherein the ring attached to the parent structure is a heteroaryl ring, includes, but is not limited to:

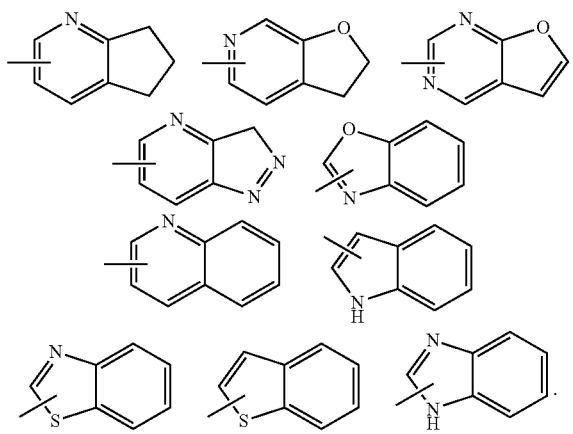

The heteroaryl can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"Alkenyl" refers to an alkyl group defined as above consisting of at least two carbon atoms and at least one carbon-carbon double bond, for example, $C_{2-8}$ alkenyl refers to a straight or branched alkenyl containing 2 to 8 carbons. Alkenyl includes, but is not limited to vinyl, 1-propenyl, 2-propenyl, 1-, 2- or 3-butenyl, and the likes.

The alkenyl can be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"Alkynyl" refers to an alkyl group defined as above consisting of at least two carbon atoms and at least one carbon-carbon triple bond, for example, $C_{2-8}$ alkynyl refers to a straight or branched alkynyl containing 2 to 8 carbons. Alkynyl includes, but is not limited to ethynyl, 1-propynyl, 2-propynyl, 1-, 2- or 3-butynyl, and the likes.

The alkynyl can be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"Alkoxy" refers to —O-(alkyl), wherein alkyl is defined as above, for example, "$C_{1-8}$ alkoxy" refers to an alkyloxy containing 1 to 8 carbons. Alkoxy includes, but is not limited to methoxy, ethoxy, propoxy, butoxy, and the likes.

The alkoxy can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"Cycloalkyloxy" refers to —O-(unsubstituted cycloalkyl), wherein cycloalkyl is defined as above, for example, "$C_{3-10}$ cycloalkyloxy" refers to a cycloalkyloxy containing 3 to 10 carbon atoms. Cycloalkyloxy includes, but is not limited to, cyclopropyloxy, cyclobutyloxy, cyclopentyloxy, cyclohexyloxy and the likes.

The cycloalkoxy can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"3-10 membered heterocyclyloxy" refers to and —O—(unsubstituted 3-10 membered heterocyclyl), wherein the definition of 3-10 membered heterocyclyl is as abovementioned; 3-10 membered heterocyclyloxy can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"$C_{5-10}$ aryloxy" refers to and —O-(unsubstituted $C_{5-10}$ aryl), wherein the definition of $C_{5-10}$ aryl is as abovementioned; $C_{5-10}$ aryloxy can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"5-10 heteroaryloxy" refers to and —O-(unsubstituted 5-10 membered heteroaryl), wherein the definition of 5-10 membered heteroaryl is as above-mentioned; 5-10 membered heteroaryloxy can optionally be either a substituted or unsubstituted one; if it is a substituted one, the substituents can preferably be one or more (preferably 1, 2, 3 or 4) of the following groups, independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, —$C_{0-8}$—S(O)$_r$R$_{10}$, —$C_{0-8}$—O—R$_{11}$, —$C_{0-8}$—C(O)OR$_{11}$, —$C_{0-8}$—C(O)R$_{12}$, —$C_{0-8}$—O—C(O)R$_{12}$, —$C_{0-8}$—NR$_{13}$R$_{14}$, —$C_{0-8}$—C(=NR$_{13}$)R$_{12}$, —$C_{0-8}$—N(R$_{13}$)—C(=NR$_{14}$)R$_{12}$, —$C_{0-8}$—C(O)NR$_{13}$R$_{14}$ and —$C_{0-8}$—N(R$_{13}$)—C(O)R$_{12}$.

"$C_{1-8}$ alkanoyl" refers to a monovalent group obtained by removing hydroxy from $C_{1-8}$ alkyl acid, is also generally referred to as "$C_{0-7}$—C(O)—", for example, "$C_1$—C(O)—" refers to acetyl; "$C_2$—C(O)—" refers to propionyl; and "$C_3$—C(O)—" refers to butyryl or isobutyryl.

"—$C_{0-8}$—S(O)$_r$R$_{10}$" means that the sulfur atom in —S(O)$_r$R$_{10}$ is bonded to $C_{0-8}$ alkyl, wherein $C_0$ alkyl means a bond, and $C_{1-8}$ alkyl is defined as above.

"—$C_{0-8}$—O—R$_{11}$" means that the oxygen atom in —O—R$_{11}$ is bonded to $C_{0-8}$ alkyl, wherein $C_0$ alkyl means a bond, and $C_{1-8}$ alkyl is defined as above.

"—$C_{0-8}$—C(O)OR$_{11}$" means that the carbonyl group in —C(O)OR$_{11}$ is bonded to $C_{0-8}$ alkyl, wherein $C_0$ alkyl means a bond, and $C_{1-8}$ alkyl is defined as above.

"—$C_{0-8}$—C(O)R$_{12}$" means that the carbonyl group in —C(O)R$_{12}$ is bonded to $C_{0-8}$ alkyl, wherein $C_0$ alkyl means a bond, and $C_{1-8}$ alkyl is defined as above.

"—$C_{0-8}$—O—C(O)R$_{12}$" means that the oxygen atom in —O—C(O)R$_{12}$ is bonded to $C_{0-8}$ alkyl, wherein $C_0$ alkyl means a bond, and $C_{1-8}$ alkyl is defined as above.

"—$C_{0-8}$—NR$_{13}$R$_{14}$" means that the nitrogen atom in —NR$_{13}$R$_{14}$ is bonded to $C_{0-8}$ alkyl, wherein $C_0$ alkyl means a bond, and $C_{1-8}$ alkyl is defined as above.

"—$C_{0-8}$—C(=NR$_{13}$)R$_{12}$" means that the carbonyl in —C(=NR$_{13}$)R$_{12}$ is bonded to $C_{0-8}$ alkyl, wherein $C_0$ alkyl means a bond, and $C_{1-8}$ alkyl is defined as above.

"—$C_{0-8}$—N(R$_{13}$)—C(=NR$_{14}$)R$_{12}$" means that the carbonyl in —N(R$_{13}$)—C(=NR$_{14}$)R$_{12}$ is bonded to $C_{0-8}$ alkyl, wherein $C_0$ alkyl means a bond, and $C_{1-8}$ alkyl is defined as above.

"—$C_{0-8}$—C(O)NR$_{13}$R$_{14}$" means that the carbonyl in —C(O)NR$_{13}$R$_{14}$ is bonded to $C_{0-8}$ alkyl, wherein $C_0$ alkyl means a bond, and $C_{1-8}$ alkyl is defined as above.

"—$C_{0-8}$—N(R$_{14}$)—C(O)R$_{13}$" means that the nitrogen atom in —N(R$_{14}$)—C(O)R$_{13}$, is bonded to $C_{0-8}$ alkyl, wherein $C_0$ alkyl means a bond, and $C_{1-8}$ alkyl is defined as above.

"$C_{1-8}$ haloalkyl" refers to a alkyl group having 1 to 8 carbon atoms, wherein any hydrogen atom on which is optionally substituted with F, Cl, Br or I, and includes, but is not limited to difluoromethyl, dichloromethyl, dibromomethyl, trifluoromethyl, trichloromethyl, tribromomethyl, and the likes.

"$C_{1-8}$ haloalkoxy" means an alkoxy having 1 to 8 carbon atoms, wherein any hydrogen atom on which is optionally substituted with F, Cl, Br or I, and includes, but is not limited to difluoromethoxy, dichloromethoxy, dibromomethoxy, trifluoroinethoxy, trichloromethoxy, tribromomethoxy, and the likes.

"Halogen" means F, Cl, Br or I. "THF" refers to tetrahydrofuran. "MeOH" means methanol. "DMF" means N,N-dimethylformamide. "THF" means tetrahydrofiran. "PE" means petroleum ether. "EA/EtOAc" means ethyl acetate. "DCM" means dichloromethane. "DIPEA" means N,N-diisopropylethylamine. "LAH/LiAlH$_4$" means lithium aluminum hydride. "MnO$_2$" means manganese dioxide. "K$_2$CO$_3$" means potassium carbonate. "K$_3$PO$_4$" means potassium phosphate. "Cs$_2$CO$_3$" means cesium carbonate. "Na$_2$CO$_3$" means sodium carbonate. "NaHCO$_3$" means sodium bicarbonate. "SO$_2$C$_2$" means thionyl chloride. "NBS" means N-bromo-succinimide. "i-PrMgCl" means isopropyl magnesium chloride. "Select-F" means 1-chloromethyl-4-fluoro-1,4-diazoniabicyclo2.2.2octane Bis(tetrafluoroborate).

"Optional" or "optionally" means that the event or environment subsequently described may, but need not, occur, including where the event or environment occurs or does not occur. For example, "heterocyclyl optionally substituted by alkyl" means that an alkyl group may be, but is not necessarily, present, and the description includes the case where the heterocyclyl is substituted with an alkyl and the case where the heterocyclyl is not substituted with an alkyl.

"Substituted" means that one or more (preferably 1, 2, 3 or 4) hydrogen atoms in a group are each independently substituted with a corresponding number of substituents. It goes without saying that a substituent is only in its possible chemical position, and those skilled in the art will be able to determine (by experiment or theory) possible or impossible substitution without undue efforts. For example, it may be unstable that an amino group or a hydroxy group having a free hydrogen is attached with a carbon atom having an unsaturated bond (such as an olefin).

"Pharmaceutical composition" means a mixture comprising one or more of the compounds described herein, or a physiologically/pharmaceutically acceptable salt or prodrug thereof, and other chemical components, for example physiological/pharmaceutically acceptable carriers and excipients. The purpose of the phannaceutical composition is to promote the administration to an organism, which facilitates the absorption of the active ingredient thereby exerting biological activities.

The present invention will be further described in detail below in conjunction with the embodiments which is not intended to limit the present invention. The present invention is also not limited to the contents of the embodiments.

The structure of the compound of the present invention is determined by nuclear magnetic resonance (NMR) or/and liquid chromatography-mass spectrometry (LC-MS). The NMR chemical shift ($\delta$) is given in parts per million (ppm). The NMR is measured by a Bruker AVANCE-400/500 nuclear magnetic apparatus, and the solvent is deuterated dimethyl sulfoxide (DMSO-$d_6$), deuterated methanol (CD$_3$OD) and deuterated chloroform (CDCl$_3$), and the internal standard is tetramethylsilane (TMS).

The measurement of LC-MS is performed by using an Agilent 6120 mass spectrometer. The measurement of HPLC is performed by using an Agilent 1200 DAD high pressure liquid chromatograph (Sunfire C18 150×4.6 mm column) and a Waters 2695-2996 high pressure liquid chromatograph (Gimini C18 150×4.6 mm column).

The thin layer chromatography silica gel plate is Yantai Yellow Sea HSGF254 or Qingdao GF254 silica gel plate. The specification of TLC is 0.15 mm-0.20 mm, and the specification for thin layer chromatography separation and purification is 0.4 mm-0.5 mm. 200-300 mesh silica gel (Yantai Huanghai silica gel) as a carrier is generally used in column chromatography.

The starting materials in the examples of the present invention are known and commercially available or can be synthesized according to methods known in the art.

Unless otherwise stated, all reactions of the present invention are carried out under continuous magnetic stirring under a dry nitrogen or argon atmosphere, the solvent is a dry solvent, and the unit of the reaction temperature is degrees Celsius (° C.).

I. Preparation of Intermediates

1. Preparation of 7-chloro-3-(3,5-dimethoxyphenyl)-1-ethyl-1,6-naphthyridin-2(1H)-one

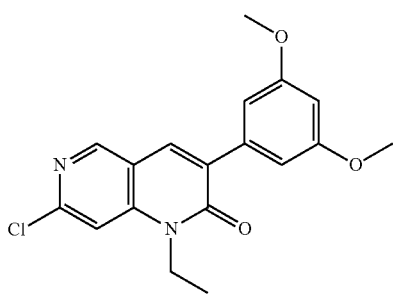

Step 1: Synthesis of ethyl 6-chloro-4-(ethylamino)nicotinate

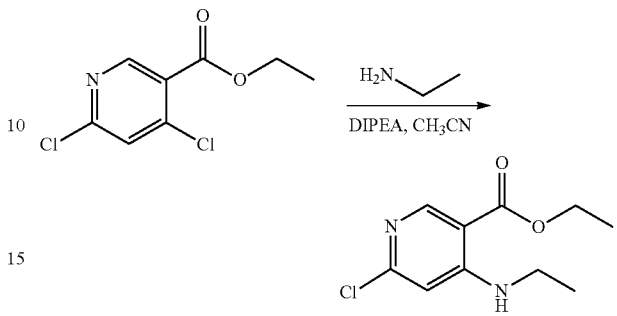

N,N-diisopropylethylamine (8.78 g, 27.3 mmmol) and ethylamine (1.76 g, 27.3 mmol, 70% aqueous solution) was added into a solution of ethyl 4,6-dichloronicotinate (5.00 g, 22.7 mmol) in acetonitrile (70 mL). The reaction solution was stirred at 70° C. for 18 hours. Then the reaction solution was cooled down, diluted with ethyl acetate (200 mL), washed with saturated salt solution (150 mL), dried over anhydrous sodium sulfate and filtered. The filtrate was concentrated to obtain ethyl 6-chloro-4-(ethylamino)nicotinate (5.20 g, yield: 100%). MS m/z (ESI): 229.2 [M+H]$^+$.

Step 2: Synthesis of (6-chloro-4-(ethylamino)pyridin-3-yl)methanol

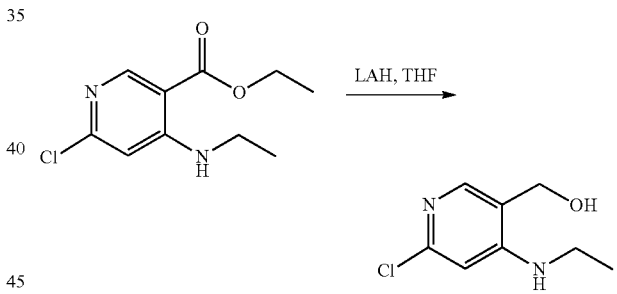

Ethyl 6-chloro-4-(ethylamino)nicotinate (5.00 g, 22.7 mmol) was dissolved in tetrahydrofuran (70 mL), and LiAlH$_4$ (1.73 g, 44.48 mmol) was added slowly in batches under an iced bath. The reaction solution was stirred under an iced bath for 1 hour. The reaction solution was quenched with sodium sulfate decahydrate, stirred at room temperature for 1 hour and filtrated. The filtrate was concentrated to obtain (6-chloro-4-(ethylamino)pyridin-3-yl)methanol (4.20 g, yield: 99%). MS m/z (ESI): 187.2 [M+H]$^+$.

Step 3: Synthesis of 6-chloro-4-(ethylamino)nicotinaldehyde

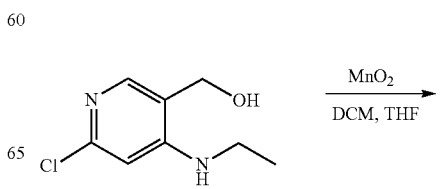

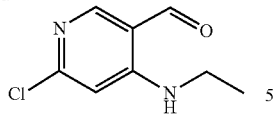

(6-chloro-4-(ethylamino)pyridin-3-yl)methanol (4.2 g, 22.5 mmol) was dissolved in a mixted solvent of dichloromethane (50 mL) and tetrahydrofiran (50 mL), and then $MnO_2$ (23.5 g, 270 mmol) was added. The reaction solution was stirred overnight at room temperature, filtrated and washed with ethyl acetate. The filtrate was concentrated to obtain 6-chloro-4-(ethylamino)nicotinaldehyde (3.5 g, yield: 84%). MS m/z (ESI): 185.0 [M+H]+.

Step 4: Synthesis of 7-chloro-3-(3,5-dimethoxyphenyl)-1-ethyl-1,6-naphthyridin-2(1H)-one

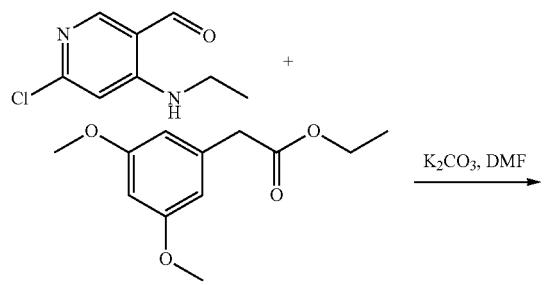

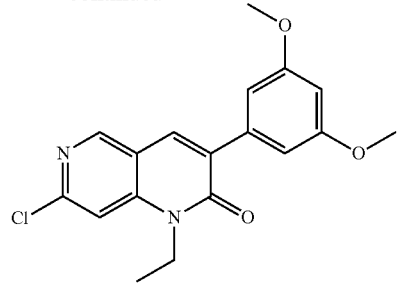

$K_2CO_3$ (2.24 g, 16.24 mmol) was added into a solution of 6-chloro-4-(ethylamino)nicotinaldehyde (1.50 g, 8.12 mmol) and ethyl 2-(3,5-diinethoxyphenyl)acetate (1.82 g, 8.12 mmol) in N,N-dimethylformamide (50 mL). The reaction solution was stirred at 110° C. for 17 hours. Afterwards, the reaction solution was cooled down to room temperature, poured into water and filtrated. The filter cake was dried to obtain 7-chloro-3-(3,5-dimethoxyphenyl)-1-ethyl-1,6-naphthyridin-2(1H)-one (2.30 g, yield: 82%). MS m/z (ESI): 345.0 [M+H]+.

Intermediates 2-8 were Prepared According to the Synthesis Method of Intermediate 1

| Intermediate No. | Structural Formula | Chemical name | MS [M + H]+. m/z (ESI): |
|---|---|---|---|
| 2 | 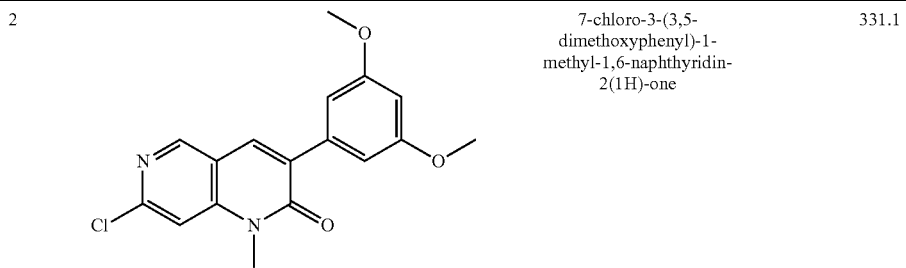 | 7-chloro-3-(3,5-dimethoxyphenyl)-1-methyl-1,6-naphthyridin-2(1H)-one | 331.1 |
| 3 | 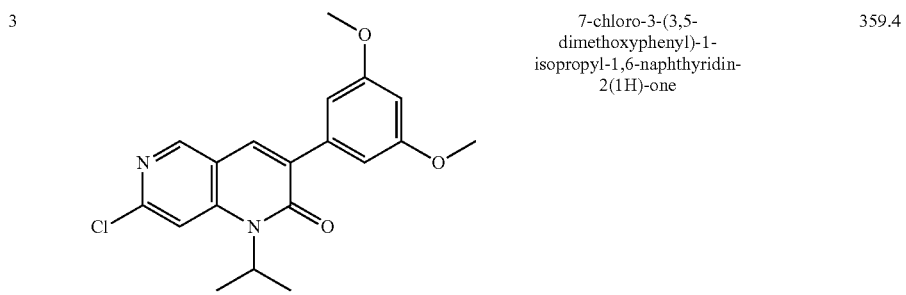 | 7-chloro-3-(3,5-dimethoxyphenyl)-1-isopropyl-1,6-naphthyridin-2(1H)-one | 359.4 |

-continued

| Intermediate No. | Structural Formula | Chemical name | MS [M + H]+. m/z (ESI): |
|---|---|---|---|
| 4 | | 7-chloro-1-(cyclopropylmethyl)-3-(3,5-dimethoxyphenyl)-1,6-naphthyridin-2(1H)-one | 371.4 |
| 5 | | 7-chloro-3-(3,5-dimethoxyphenyl)-1-(2-morpholinoethyl)-1,6-naphthyridin-2(1H)-one | 430.1 |
| 6 | | 7-chloro-3-(3,5-dimethoxyphenyl)-1-(2-(dimethylamino)ethyl)-1,6-naphthyridin-2(1H)-one | 388 |
| 7 | | 7-chloro-3-(3,5-dimethoxyphenyl)-1-(tetrahydrofuran-3-yl)-1,6-naphthyridin-2(1H)-one | 387 |

| Intermediate No. | Structural Formula | Chemical name | MS [M + H]+. m/z (ESI): |
|---|---|---|---|
| 8 | | 7-chloro-3-(3,5-dimethoxyphenyl)-1-(oxetane-3-yl)-1,6-naphthyridin-2(1H)-one | 373 |

9. Preparation of 7-chloro-3-(2,6-dichloro-3,5-dimethoxyphenyl)-1-ethyl-1,6-naphthyridin-2(1H)-one

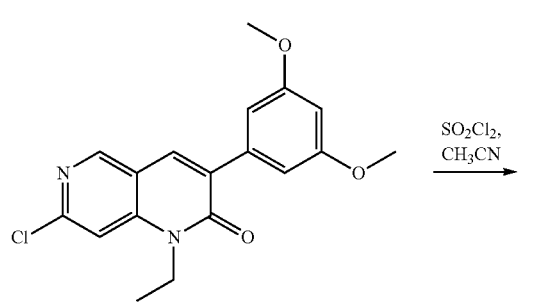

A solution of 7-chloro-3-(3,5-dimethoxyphenyl)-1-ethyl-1,6-naphthyridin-2(1H)-one (500 mg, 1.45 mmol) in acetonitrile (8 mL) was cooled down to −30° C., and then $SO_2Cl_2$ (640 mg, 3.62 mmol) was added dropwise slowly. The reaction solution was stirred at −30° C. for 30 Minutes. Afterwards, the reaction solution was quenched with saturated sodium bicarbonate and filtrated. The filter cake was washed and dried to obtain 7-chloro-3-(2,6-dichloro-3,5-dimethoxyphenyl)-1-ethyl-1,6-naphthyridin-2(1H)-one (520 mg, yield: 87%). MS m/z (ESI): 413.2, 415.2[M+H]+.

Intermediates 10-16 were Prepared According to the Synthesis Method of Intermediate 9

| Intermediate No. | Structural Formula | Chemical name | MS [M + H]+, m/z (ESI): |
|---|---|---|---|
| 10 | 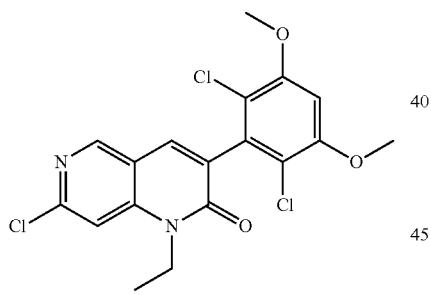 | 7-chloro-3-(2,6-dichloro-3,5-dimethoxyphenyl)-1-methyl-1,6-naphthyridin-2(1H)-one | 398.7, 400.7 |

-continued

| Intermediate No. | Structural Formula | Chemical name | MS [M + H]+, m/z (ESI): |
|---|---|---|---|
| 11 | | 7-chloro-3-(2,6-dichloro-3,5-dimethoxyphenyl)-1-isopropyl-1,6-naphthyridin-2(1H)-one | 427.2, 429.2 |
| 12 | | 7-chloro-1-(cyclopropylmethyl)-3-(2,6-dichloro-3,5-dimethoxyphenyl)-1,6-naphthyridin-2(1H)-one | 439.2, 441.2 |
| 13 | | 7-chloro-3-(2,6-dichloro-3,5-dimethoxyphenyl)-1-(2-morpholinoethyl)-1,6-naphthyridin-2(1H)-one | 498.3, 500.3 |
| 14 | | 7-chloro-3-(2,6-dichloro-3,5-dimethoxyphenyl)-1-(2-(dimethylamino)ethyl)-1,6-naphthyridin-2(1H)-one | 456, 458 |

| Intermediate No. | Structural Formula | Chemical name | MS [M + H]⁺, m/z (ESI): |
|---|---|---|---|
| 15 | | 7-chloro-3-(2,6-dichloro-3,5-dimethoxyphenyl)-1-(tetrahydrofuran-3-yl)-1,6-naphthyridin-2(1H)-one | 455, 457 |
| 16 | | 7-chloro-3-(2,6-dichloro-3,5-dimethoxyphenyl)-1-(oxetane-3-yl)-1,6-naphthyridin-2(1H)-one | 441, 443 |

17. Preparation of 7-chloro-1-ethyl-3-(2-fluoro-3,5-dimethoxyphenyl)-1,6-naphthyridin-2(1H)-one

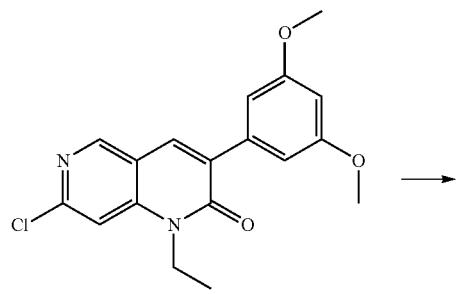

Select-F (370 rug, 1.044 mmol) was added to a solution of 7-chloro-3-(3,5-dimethoxyphenyl)-1-ethyl-1,6-naphthyridin-2(1H)-one (300 mg, 0.870 mmol) in acetonitrile at −15° C. The reaction solution was warmed to room temperature slowly and stirred for 1 hour. Then the reaction solution was cooled down to −15° C., again, and additional select-F (300 mg, 0.847 mmol) was added. The reaction solution was then slowly warmed to room temperature and stirred for 50 minutes. The reaction solution was diluted with DCM and washed with saturated NaHCO₃ solution, dried over anhydrous sodium sulfate and filtered. The filtrate was concentrated and then separated by column chromatography (PE:EtOAc=0~17%) to obtain 7-chloro-1-ethyl-3-(2-fluoro-3,5-dimethoxyphenyl)-1,6-naphthyridin-2(1H)-one (223 mg, purity: 76%). The crude product (80 mg) was separated by PTLC (PE/EtOAc=8:1) to obtain 7-chloro-1-ethyl-3-(2-fluoro-3,5-dimethoxyphenyl)-1,6-naphthyridin-2(1H)-one (43 mg). MS m/z (ESI): 363.2 [M–H]⁺.

18. Preparation of 7-chloro-3-(2-chloro-3,5-dimethoxyphenyl)-1-ethyl-1,6-naphthyridin-2(1H)-one

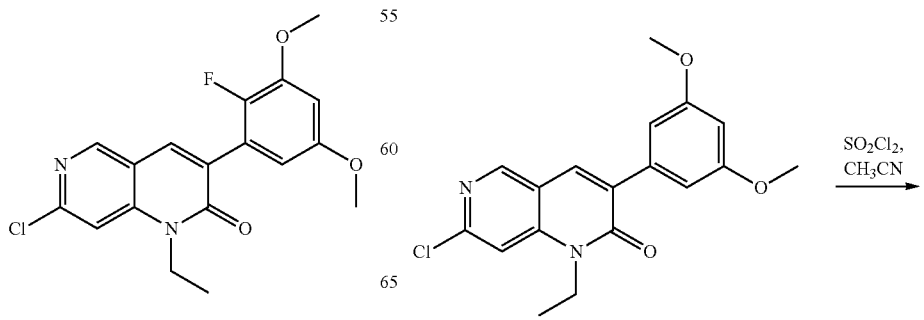

-continued

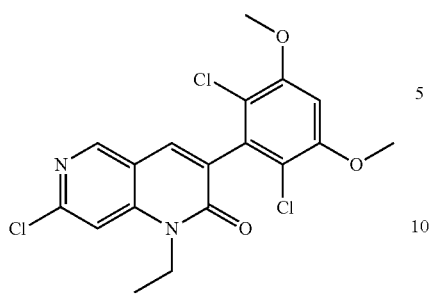

A solution of 7-chloro-3-(3,5-dimethoxyphenyl)-1-ethyl-1,6-naphthyridin-2(1H)-one (200 mg, 0.58 mmol) in acetonitrile (5 mL) was cooled down to −30° C., and then SO$_2$Cl$_2$ (86 mg, 0.64 mmmol) was slowly added dropwise. The reaction solution was stirred at −30° C. for 20 minutes. Afterwards, the reaction solution was quenched with saturated sodium bicarbonate, extracted with ethyl acetate and concentrated. The residue was separated by column chromatography (EA/DCM=0%-10%) to obtain 7-chloro-3-(2-chloro-3,5-dimethoxyphenyl)-1-ethyl-1,6-naphthyridin-2(1H)-one (165 mg, yield: 75%). MS m/z (ESI): 379.2, 381.2[M+H]$^+$.

19. Preparation of 4-(2-(4-(4,4,5,5-tetramethyl-1,3,2-dioxaborolan-2-yl)-1H-pyrazol-1-yl)ethyl)morpholine

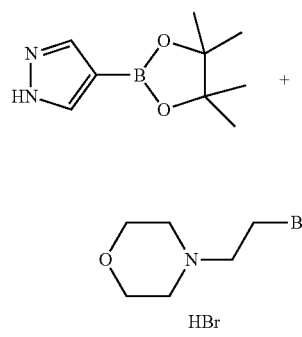

Cs$_2$CO$_3$ (3.35 g, 10.3 mmol) was added into a solution of 4-(4,4,5,5-tetramethyl-1,3,2-dioxaborolan-2-yl)-1H-pyrazole (1.0 g, 5.15 mmol) and 4-(2-bromoethyl)morpholine bromide (1.40 g, 7.72 mmol) in N,N-dimethylformamide (8 mL). The reaction solution was stirred at 100° C. for 17 hours. The suspension was filtrated, and the filtrate was separated by a reverse-phase column chromatography (CH$_3$CN:H$_2$O=0%-15%) to obtain 4-(2-(4-(4,4,5,5-tetramethyl-1,3,2-dioxaborolan-2-yl)-1H-pyrazol-1-yl)ethyl)morpholine (1.1 g, yield: 70%). MS m/z (ESI): 308.2 [M+H]$^+$.

20. Preparation of 3-bromo-1-ethyl-7-(1-methyl-1H-pyrazol-4-yl)-1,6-naphthyridin-2(1H)-one

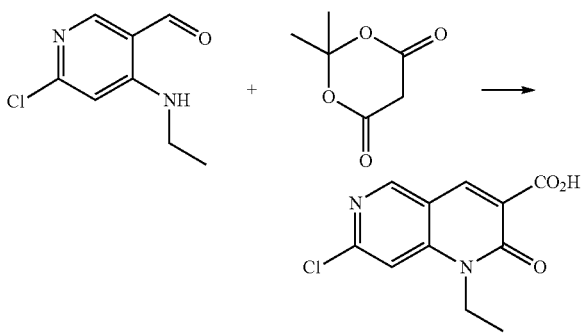

Step 1: Synthesis of 7-chloro-1-ethyl-2-oxo-1,2-dihydro-1,6-naphthyridine-3-carboxylic acid

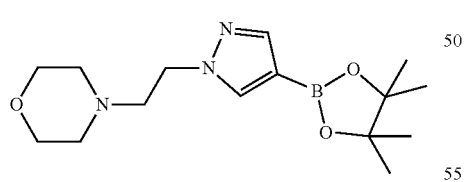

2,2-dimethyl-1,3-dioxan-4,6-dione (546 mg, 3.79 mmol), piperidine (32 mg, 0.38 mmol) and acetic acid (68 mg, 1.14 mmol) were added into a solution of 6-chloro-4-(ethylamino)nicotinaldehyde (700 mg, 3.79 mmol) in ethanol (7 mL). The reaction solution refluxed for 3 hours. Afterwards, the reaction solution was cooled down to room temperature and filtrated. The filter cake was washed with ethanol and then dried to obtain 7-chloro-1-ethyl-2-oxo-1,2-dihydro-1,6-naphthyridine-3-carboxylic acid (850 mg, yield 89%). MS m/z (ESI): 253.2 [M+H]$^+$.

Step 2: Synthesis of 1-ethyl-7-(1-methyl-1H-pyrazol-4-yl)-2-oxo-1,2-dihydro-1,6-naphthyridine-3-carboxylic acid

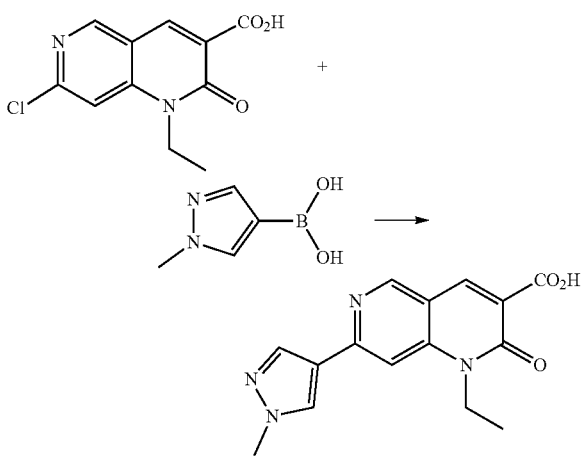

[1,1'-bis(diphenylphosphino)ferrocene]palladium bichloride (246 mg, 0.34 mmol) and Na₂CO₃ (2N, 5 mL) were added into a solution of 7-chloro-1-ethyl-2-oxo-1,2-dihydro-1,6-naphthyridin-3-carboxylic acid (850 mg, 3.36 mmol) and 1-methyl-1H-pyrazol-4-borate (848 mg, 6.73 mmol) in 1,4-dioxane (15 mL). The suspension was stirred at 95° C. for 16 hours. Afterwards, the suspension was cooled down to room temperature, added with water and extracted with ethyl acetate. The water phase was adjusted to pH 2~3 with 2N hydrochloric acid and the precipitate was filtrated. The filter cake was washed with ethanol and then dried to obtain 1-ethyl-7-(1-methyl-1H-pyrazol-4-yl)-2-oxo-1,2-dihydro-1,6-naphthyridine-3-carboxylic acid (950 mg, yield: 95%). MS m/z (ESI): 299.2 [M+H]T.

Step 3: Synthesis of 3-bromo-1-ethyl-7-(1-methyl-1H-pyrazol-4-yl)-1,6-naphthyridin-2(1H)-one

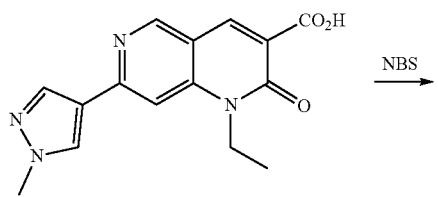

NBS →

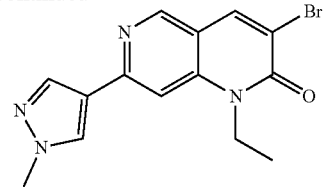

1-ethyl-7-(1-methyl-1H-pyrazol-4-yl)-2-oxo-1,2-dihydro-1,6-naphthyridin-3-carboxylic acid (400 mg, 1.34 mmol) was dissolved in a mixed solution of N,N-dimethylformamide (18 mL) and water (2 mL), and then N-bromosuccinimide (477 mg, 2.68 mmol) and lithium acetate (273 mg, 2.68 mmol) were added. The reaction solution was subjected to microwave reaction at 110° C. for 3 hours. Afterwards, the reaction solution was cooled down to room temperature, diluted with water, extracted with ethyl acetate and washed with saturated salt solution. The organic phase was concentrated and separated by column chromatography (ethyl acetate/dichloromethane=0~20%) to obtain 3-bromo-1-ethyl-7-(1-methyl-1H-pyrazol-4-yl)-1,6-naphthyridin-2(1H)-one (150 mg, yield: 34%). MS m/z (ESI): 333.2, 335.2[M+H]⁺.

Intermediates 21-27 were Prepared According to the Synthesis Method of Intermediate 20

| Intermediate No. | Structural Formula | Chemical name | MS [M + H]⁺. m/z (ESI): |
|---|---|---|---|
| 21 | ![structure] | 3-bromo-1-isopropyl-7-(1-methyl-1H-pyrazol-4-yl)-1,6-naphthyridin-2(1H)-one | 347, 349 |
| 22 | ![structure] | 3-bromo-1-(cyclopropylmethyl)-7-(1-methyl-1H-pyrazol-4-yl)-1,6-naphthyridin-2(1H)-one | 359, 361 |
| 23 | ![structure] | 3-bromo-1-(2-(dimethylamino)ethyl)-7-(1-methyl-1H-pyrazol-4-yl)-1,6-naphthyridin-2(1H)-one | 376, 378 |

-continued

| Intermediate No. | Structural Formula | Chemical name | MS [M + H]+. m/z (ESI): |
|---|---|---|---|
| 24 | | 3-bromo-7-(1-methyl-1H-pyrazol-4-yl)-1-(tetrahydrofuran-3-yl)-1,6-naphthyridin-2(1H)-one | 375, 377 |
| 25 | | 3-bromo-1-ethyl-7-(1-(2-morpholinoethyl)-1H-pyrazol-4-yl)-1,6-naphthyridin-2(1H)-one | 432, 434 |
| 26 | | 3-bromo-1-isopropyl-7-(1-(2-morpholinoethyl)-1H-pyrazol-4-yl)-1,6-naphthyridin-2(1H)-one | 446, 448 |
| 27 | | 3-bromo-1-ethyl-7-(3-methyl-1-(2-morpholinoethyl)-1H-pyrazol-4-yl)-1,6-naphthyridin-2(1H)-one | 446, 448 |

28. Preparation of 2-(2,6-difluoro-3,5-dimethoxy-phenyl)-4,4,5,5-tetramethyl-1,3,2-dioxabo rolane

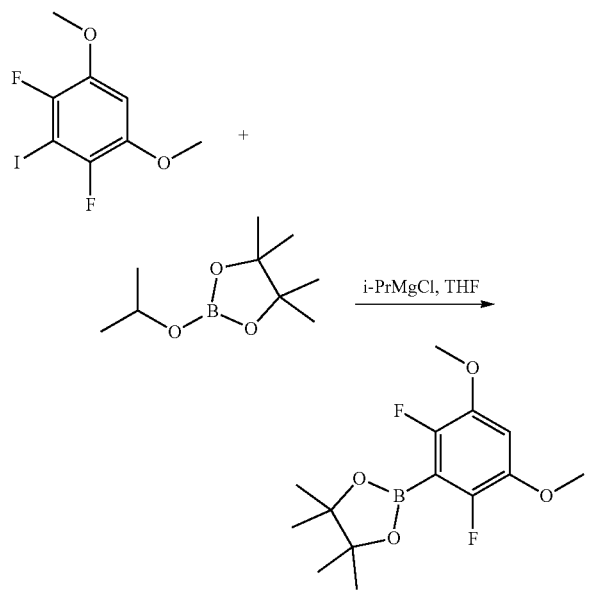

Isopropylmagnesium chloride solution (2.0 mL, 4.0 mmol, in 2N tetrahydrofuran) was slowly added into a solution of 2,4-difluoro-3-iodo-1,5-dimethoxybenzene (1.00 g, 3.33 mmol) in tetrahydrofuran (15 mL) at −10° C. The reaction solution was stirred at −10° C. for 10 minutes, and then 2-isopropoxy-4,4,5,5-tetramethyl-1,3,2-dioxaborolan (805 mg, 4.33 mmol) was added. Afterwards, the reaction solution was stirred at room temperature for 2 hours, quenched with saturated ammonium chloride solution, extracted with ethyl acetate. The organic phase was washed with water, dried, concentrated and separated by column chromatography (BA/DCM=0~20%) to obtain 2-(2,6-difluoro-3,5-dimethoxyphenyl)-4,4,5,5-tetramethyl-1,3,2-dioxaborolane (800 mg, yield: 80%). MS m/z (ESI): 301.0 [M+H]+.

II. Preparation of Specific Examples

Example 1. Preparation of 3-(2,6-dichloro-3,5-dimethoxyphenyl)-1-ethyl-7-(1-methyl-1H-pyrazol-4-yl)-1,6-naphthyridin-2(1H)-one

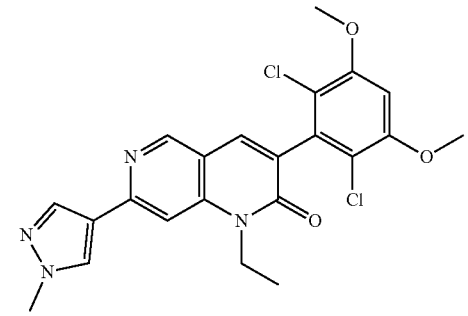

An aqueous solution of [1,1'-bis(diphenylphosphino)ferrocene]palladium bichloride (9 mg, 0.012 mmol) and Na$_2$CO$_3$ (0.5 mL, 1.0 mmol, 2N) was added into a solution of 7-chloro-3-(2,6-dichloro-3,5-dimethoxyphenyl)-1-ethyl-1,6-naphthyridin-2(1H)-one (50 mg, 0.12 mmol) and 1-methyl-1H-pyrazol-4-borate (30 mg, 0.24 mmol) in 1,4-dioxane (2 mL). The reaction solution was stirred at 95° C. for 16 hours. Afterwards, the reaction solution was cooled down to room temperature, added with water a nd extracted with ethyl acetate. The organic phase was concentrated and the residue was separated b y PTLC (EA/DCM=1/2) to obtain 3-(2,6-dichloro-3,5-dimethoxyphenyl)-1-ethyl-7-(1-methyl-1H-pyraz ol-4-yl)-1,6-naphthyridin-2(1H)-one (35 mg, yield: 63%) MS n/z (ESI): 459.4, 461.4 [M−H]+.

$^1$H NMR (400 MHz, CDCl$_3$) δ 8.76 (s, 1H), 8.25 (s, 1H), 8.05 (s, 1H), 7.64 (s, 1H), 7.35 (s, 1H), 6.65 (s, 1H), 4.41 (q, J=7.1 Hz, 2H), 4.01 (s, 3H), 3.96 (s, 6H), 1.43 (t, J=7.0 Hz, 3H).

Examples 2-24 were Prepared According to the Synthesis Method of Example 1

| Example No. | Structural Formula | Chemical name | MS m/z (ESI): [M + H]+/$^1$HNMR |
| --- | --- | --- | --- |
| 2 | | 3-(2,6-dichloro-3,5-dimethoxyphenyl)-1-methyl-7-(1-methyl-1H-pyrazol-4-yl)-1,6-naphthyridin-2(1H)-one | MS m/z (ESI): 445.4, 447.4 [M + H]+. $^1$H NMR (400 MHz, CDCl$_3$) δ 8.73 (s, 1H), 8.08 (s, 1H), 8.05 (s, 1H), 7.64 (s, 1H), 7.33 (s, 1H), 6.64 (s, 1H), 4.00 (s, 3H), 3.96 (s, 6H), 3.79 (s, 3H). |

| Example No. | Structural Formula | Chemical name | MS m/z (ESI): [M + H]⁺/¹HNMR |
|---|---|---|---|
| 3 | 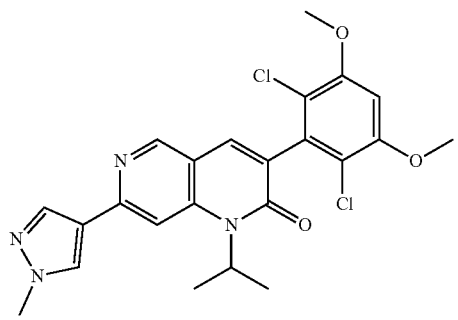 | 3-(2,6-dichloro-3,5-dimethoxyphenyl)-1-isopropyl-7-(1-methyl-1H-pyrazol-4-yl)-1,6-naphthyridin-2(1H)-one | MS m/z (ESI): 473.4, 475.4 [M + H]⁺. ¹H NMR (400 MHz, CDCl₃) δ 8.72 (s, 1H), 8.16 (s, 1H), 8.02 (s, 1H), 7.59 (s, 1H), 7.52 (s, 1H), 6.63 (s, 1H), 4.00 (s, 3H), 3.95 (s, 6H), 3.49 (d, J = 3.3 Hz, 1H), 1.71 (d, J = 6.8 Hz, 6H). |
| 4 | 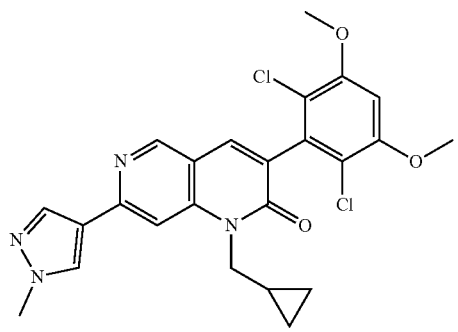 | 1-(cyclopropylmethyl)-3-(2,6-dichloro-3,5-dimethoxyphenyl)-7-(1-methyl-1H-pyrazol-4-yl)-1,6-naphthyridin-2(1H)-one | MS m/z (ESI): 485.0, 487.0 [M + H]⁺. ¹H NMR (400 MHz, CDCl₃) δ 8.75 (s, 1H), 8.23 (br s, 1H), 8.06 (s, 1H), 7.65 (s, 1H), 6.64 (s, 1H), 4.31 (d, J = 7.0 Hz, 2H), 4.01 (s, 3H), 3.95 (s, 6H), 1.33-1.25 (m, 1H), 0.62-0.54 (m, 4H). |
| 5 | 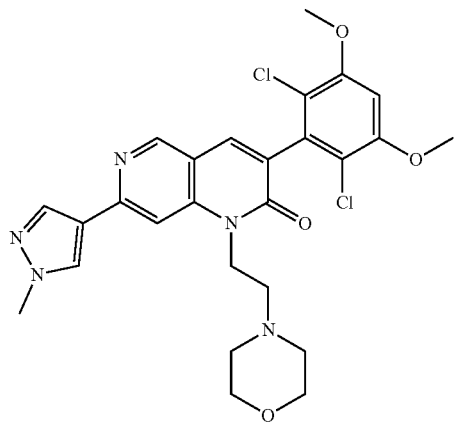 | 3-(2,6-dichloro-3,5-dimethoxyphenyl)-7-(1-methyl-1H-pyrazol-4-yl)-1-(2-morpholinoethyl)-1,6-naphthyridin-2(1H)-one | MS m/z (ESI): 544.4, 546.4 [M + H]⁺. ¹H NMR (400 MHz, CDCl₃) δ 8.74 (s, 1H), 8.03 ( br s, 2H), 7.65 (s, 1H), 7.40 (br s, 1H), 6.64 (s, 1H), 4.50 (br s. 2H), 4.00 (s, 3H), 3.95 (s, 6H), 3.69 (br s, 4H), 2.75 (br s, 2H), 2.60 (br s, 4H). |
| 6 | 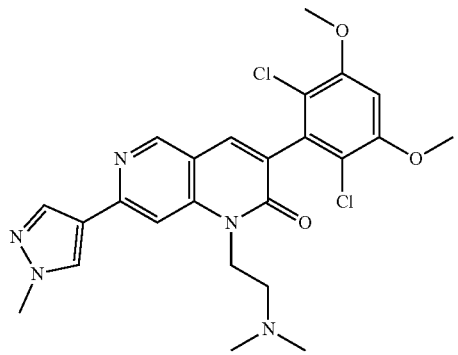 | 3-(2,6-dichloro-3,5-dimethoxyphenyl)-1-(2-(dimethylamino)ethyl)-7-(1-methyl-1H-pyrazol-4-yl)-1,6-naphthyridin-2(1H)-one | MS m/z (ESI): 502.3, 504.3 [M + H]⁺. ¹H NMR (400 MHz, CDCl₃) δ 8.91 (s, 1H), 8.77 (s, 1H), 8.32 (s, 1H), 8.19 (s, 1H), 7.71 (s, 1H), 6.65 (s, 1H), 4.95 (t, J = 8.0 Hz, 2H), 4.01 (s, 3H), 3.95 (s, 6H), 3.39-3.27 (m, 2H), 2.92 (s, 6H). |

-continued

| Example No. | Structural Formula | Chemical name | MS m/z (ESI): [M + H]+/1HNMR |
|---|---|---|---|
| 7 | 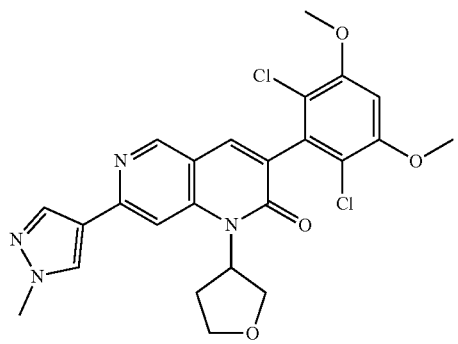 | 3-(2,6-dichloro-3,5-dimethoxyphenyl)-7-(1-methyl-1H-pyrazol-4-yl)-1-(tetrahydrofuran-3-yl)-1,6-naphthyridin-2(1H)-one | MS m/z (ESI): 501, 503 [M + H]+. 1H NMR (500 MHz, CDCl3) δ 8.73 (s, 1H), 8.07 (s, 1H), 8.06 (s, 1H), 8.02 (s, 1H), 7.60 (s, 1H), 6.64 (s, 1H), 6.42 6.35 (m, 1H), 4.56-4.52 (m, 1H), 4.28 (dd, J = 10.4, 4.1 Hz, 1H), 4.07 (t, J = 9.9 Hz, 1H), 3.99 (s, 3H), 3.95 (s, 6H), 3.88-3.81( m, 1H), 2.49-2.33 (m, 2H). |
| 8 | 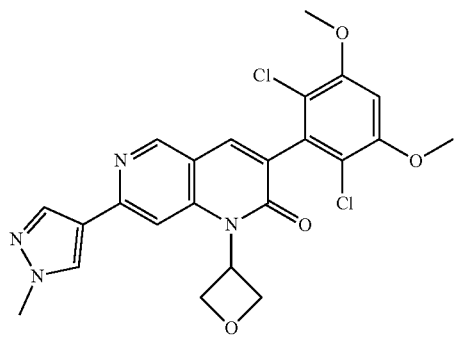 | 3-(2,6-dichloro-3,5-dimethoxyphenyl)-7-(1-methyl-1H-pyrazol-4-yl)-1-(oxetan-3-yl)-1,6-naphthyridin-2(1H)-one | MS m/z (ESI): 487.2, 489.2 [M + H]+. 1H NMR (400 MHz, CDCl3) δ 8.80 (s, 1H), 8.27 (s, 1H), 7.98 (s, 1H), 7.67 (s, 1H), 6.97 (s, 1H), 6.65 (s, 1H), 5.72-5.61 (m, 1H), 5.16 (t, J = 7.3 Hz, 2H), 4.98 (t, J = 7.5 Hz, 2H), 4.01 (s, 3H), 3.96 (s, 6H). |
| 9 | 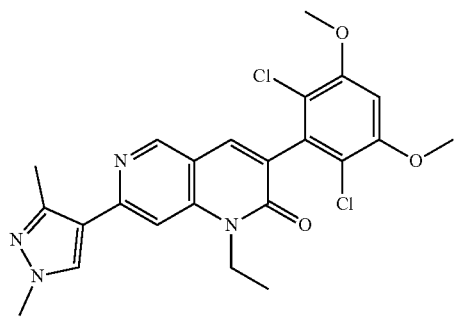 | 3-(2,6-dichloro-3,5-dimethoxyphenyl)-7-(1,3-dimethyl-1H-pyrazol-4-yl)-1-ethyl-1,6-naphthyridin-2(1H)-one | MS m/z (ESI): 473.2, 475.2 [M + H]+. 1H NMR (400 MHz, CDCl3) δ 8.79 (s, 1H), 8.19 (br s, 1H), 7.65 (s, 1H), 7.36 (s, 1H), 6.65 (s, 1H), 4.40 (q, J = 7.2 Hz, 2H), 3.96 (s, 6H), 3.93 (s, 3H), 2.61 (s, 3H), 1.44 (t, J = 7.1 Hz, 3H). |
| 10 | 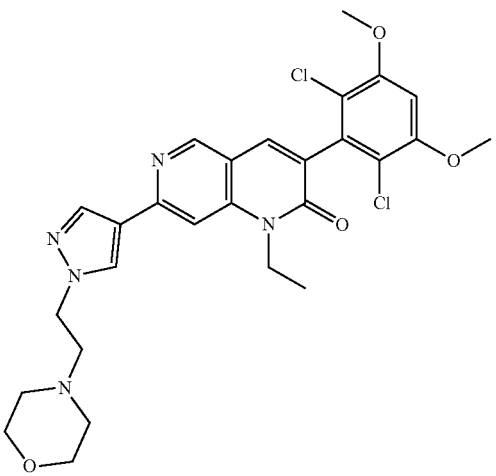 | 3-(2,6-dichloro-3,5-dimethoxyphenyl)-1-ethyl-7-(1-(2-morpholinoethyl)-1H-pyrazol-4-yl)-1,6-naphthyridin-2(1H)-one | MS m/z (ESI): 558.4, 560.4 [M + H]+ 1H NMR (400 MHz, CDCl3) δ 8.67 (s, 1H), 8.07 (s, 1H), 7.97 (s, 1H), 7.57 (s, 1H), 7.26 (s, 1H), 6.57 (s, 1H), 4.33 (q, J = 7.1 Hz, 2H), 4.27 (t, J = 6.6 Hz, 2H), 3.88 (s, 6H), 3.65 (t, J = 4.6 Hz, 4H), 2.84 (t, J = 6.6 Hz, 2H), 2.46 (t, J = 4.6 Hz, 4H), 1.36 (t, J = 7.1 Hz, 3H). |

| Example No. | Structural Formula | Chemical name | MS m/z (ESI): [M + H]+/1HNMR |
|---|---|---|---|
| 11 | 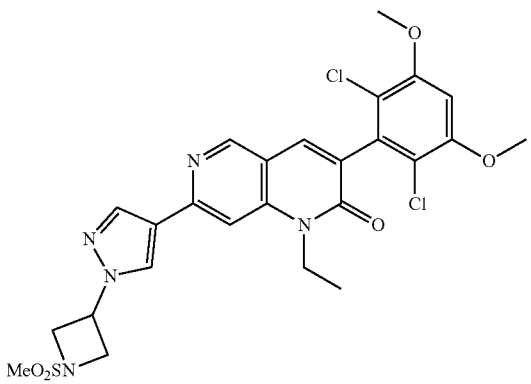 | 3-(2,6-dichloro-3,5-dimethoxyphenyl)-1-ethyl-7-(1-(1-(methylsulfonyl)azetidin-3-yl)-1H-pyrazol-4-yl)-1,6-naphthyridin-2(1H)-one | MS m/z (ESI): 578.4, 580.5 [M + H]+. 1H NMR (400 MHz, CDCl3) δ 8.78 (s, 1H), 8.64 (br s, 1H), 8.18 (s, 1H), 7.66 (s, 1H), 7.39 (s, 1H), 6.66 (s, 1H), 5.24-5.16 (m, 1H), 4.53-4.38 (m, 6H), 3.96 (s, 6H), 3.06 (s, 3H), 1.45 (t, J = 7.1 Hz, 3H). |
| 12 | 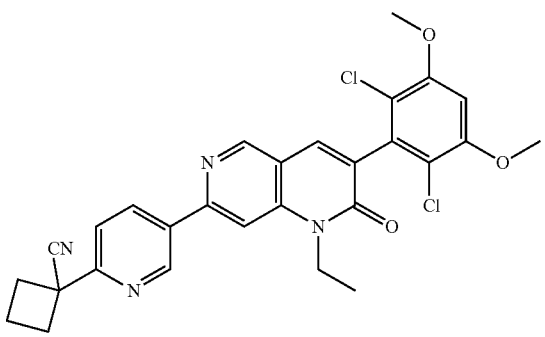 | 1-(5-(3-(2,6-dichloro-3,5-dimethoxyphenyl)-1-ethyl-2-oxo-1,2-dihydro-1,6-naphthyridin-7-yl)pyridin-2-yl)cyclobutane-1-carbonitrile | MS m/z (ESI): 535.0, 537.1 [M + H]+. H NMR (400 MHz, CDCl3) δ 9.29 (s, 1H), 8.93 (s, 1H), 8.45 (s, 1H), 7.74 (s, 2H), 7.65 (s, 1H), 6.66 (s, 1H), 4.53-4.38 (m, 2H), 3.97 (s, 6H), 2.96 (s, 2H), 2.84 (d, J = 11.8 Hz, 2H), 2.53-2.38 (m, 1H), 2.31-2.18 (m, 1H), 1.51-1.32 (m, 3H). |
| 13 | 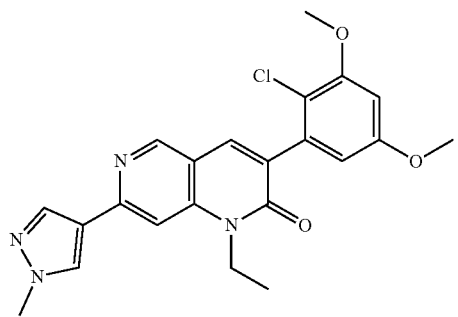 | 3-(2-chloro-3,5-dimethoxyphenyl)-1-ethyl-7-(1-methyl-1H-pyrazol-4-yl)-1,6-naphthyridin-2(1H)-one | MS m/z (ESI): 425.4 [M + H]+. 1H NMR (400 MHz, CDCl3) δ 8.77 (s, 1H), 8.23 (s, 1H), 8.05 (s, 1H), 7.73 (s, 1H), 7.34 (s, 1H), 6.58 (d, J = 2.2 Hz, 1H), 6.53 (s, 1H), 4.44-4.37 (m, 2H), 4.01 (s, 3H), 3.91 (s, 3H), 3.82 (s, 3H), 1.44 (t, J = 6.9 Hz, 3H). |
| 14 | 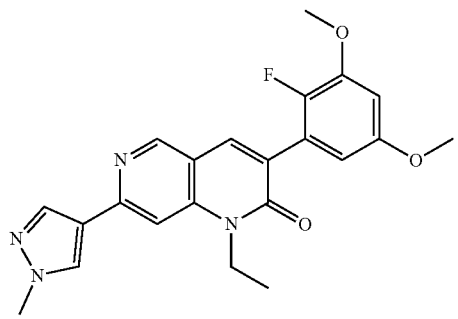 | 1-ethyl-3-(2-fluoro-3,5-dimethoxyphenyl)-7-(1-methyl-1H-pyrazol-4-yl)-1,6-naphthyridin-2(1H)-one | MS m/z (ESI): 409.2 [M + H]+. 1H NMR (400 MHz, CDCl3) δ 8.74 (s, 1H), 8.18 (br s, 1H), 8.04 (s, 1H), 7.83 (s, 1H), 7.31 (s, 1H), 6.60 (s, 1H), 6.58 (s, 1H), 4.40 (q, J = 7.1 Hz, 2H), 4.00 (s, 3H), 3.90 (s, 3H), 3.81 (s, 3H), 1.43 (t, J = 7.1 Hz, 3H). |

| Example No. | Structural Formula | Chemical name | MS m/z (ESI): [M + H]⁺/¹HNMR |
|---|---|---|---|
| 15 | | 3-(2,6-dichloro-3,5-dimethoxyphenyl)-1-methyl-7-(1-(2-morpholinoethyl)-1H-pyrazol-4-yl)-1,6-naphthyridin-2(1H)-one | MS m/z (ESI): 544.2, 546.2 [M + H]⁺. ¹H NMR (500 MHz, DMSO-d₆) δ 8.85 (s, 1H), 8.52 (s, 1H), 8.23 (s, 1H), 7.96 (s, 1H), 7.73 (s, 1H), 7.01 (s, 1H), 4.30 (t, J = 6.6 Hz, 2H), 3.97 (s, 6H), 3.71 (s, 3H), 3.55 (t, J = 4.6 Hz, 4H), 2.78 (t, J = 6.6 Hz, 2H), 2.44 (t, J = 4.6 Hz, 4H). |
| 16 | | 1-(5-(3-(2,6-dichloro-3,5-dimethoxyphenyl)-2-oxo-1-(tetrahydrofuran-3-yl)-1,2-dihydro-1,6-naphthyridin-7-yl)pyridin-2-yl)cyclobutane-1-carbonitrile | ¹H NMR (500 MHz, CDCl₃) δ 9.36 (d, J = 2.3 Hz, 1H), 8.91 (s, 1H), 8.46 (dd, J = 8.2, 2.3 Hz, 1H), 8.43 (s, 1H). 7.69 (s, 1H), 7.68 (d, J = 7.5 Hz, 1H), 6.66 (s, 1H), 6.45 (dq, J = 10.5, 5.5, 4.4 Hz, 1H), 4.58 (t, J = 8.3 Hz, 1H), 4.31 (dd, J = 10.6, 3.9 Hz, 1H), 4.10 (t, J = 10.0 Hz, 1H), 3.97 (s, 6H), 3.86 (td, J = 10.1, 6.5 Hz, 1H), 2.97 (dt, J = 12.4, 9.1 Hz, 2H), 2.86-2.76 (m, 2H), 2.52-2.36 (m, 3H), 2.21 (dtd, J = 11.6, 9.4, 4.7 Hz, 1H) |
| 17 | | 3-(2,6-dichloro-3,5-dimethoxyphenyl)-7-(1-methyl-1H-pyrazol-4-yl)-1-(tetrahydro-2H-pyran-4-yl)-1,6-naphthyridin-2(1H)-one | MS m/z (ESI): 515.4, 517.4 [M + H]⁺. ¹H NMR (500 MHz, CDCl₃) δ 8.77 (s, 1H), 8.56 ( br s, 1H), 8.09 (s, 1H), 7.70 (s, 1H), 7.62 (s, 1H), 6.66 (s, 1H), 4.26-4.17 (m, 2H), 4.03 (s, 3H), 3.96 (s, 6H), 3.68-3.58 (m, 2H), 2.93 (m, 2H), 1.81 (m, 2H), 1.28-1.23 (m, 1H). |

-continued

| Example No. | Structural Formula | Chemical name | MS m/z (ESI): [M + H]⁺/¹HNMR |
|---|---|---|---|
| 18 | | 3-(2,6-dichloro-3,5-dimethoxyphenyl)-7-(1-(2-morpholinoethyl)-1H-pyrazol-4-yl)-1-(tetrahydrofuran-3-yl)-1,6-naphthyridin-2(1H)-one | MS m/z (ESI): 300.8 [M/2 + H]⁺. ¹H NMR (500 MHz, CDCl₃) δ 8.74 (s, 1H), 8.19 (br s, 1H), 8.11 (s, 1H), 8.09 (s, 1H), 7.61 (s, 1H), 6.65 (s, 1H), 6.43-6.34 (m, 1H), 4.63-4.53 (m, 1H), 4.46 (br s, 2H), 4.28 (dd, J = 10.4, 4.0 Hz, 1H), 4.07 (t, J = 9.9 Hz, 1H), 3.96 (s, 6H), 3.89-3.82 (m, 1H), 3.81 (br s, 4H), 2.96 (br s, 2H), 2.64 (br s, 4H), 2.43 (m, 2H). |
| 19 | | 1-cyclopentyl-3-(2,6-dichloro-3,5-dimethoxyphenyl)-7-(1-methyl-1H-pyrazol-4-yl)-1,6-naphthyridin-2(1H)-one | MS m/z (ESI): 499.4, 501.4 [M + H]⁺. ¹H NMR (500 MHz, CDCl₃) δ 8.73 (s, 1H), 8.28 (br s, 1H), 8.02 (s, 1H), 7.60 (s, 1H), 7.52 (s, 1H), 6.64 (s, 1H), 5.47-5.37 (m, 1H), 4.01 (s, 3H), 3.95 (s, 6H), 2.38-2.28 (m, 2H), 2.19-2.11 (m, 2H), 2.10-2.03 (m, 2H), 1.82-1.75 (m, 2H). |
| 20 | | 1-(5-(3-(2,6-dichloro-3,5-dimethoxyphenyl)-1-methyl-2-oxo-1,2-dihydro-1,6-naphthyridin-7-yl)pyridin-2-yl)cyclobutane-1-carbonitrile | MS m/z (ESI): 521.2, 523.2 [M + H]⁺. ¹H NMR (500 MHz, CDCl₃) δ 9.31 (d, J = 2.2 Hz, 1H), 9.00 (s, 1H), 8.57 (d, J = 7.6 Hz, 1H), 7.78 (s, 1H), 7.76 (s, 1H), 7.69 (s, 1H), 6.67 (s, 1H), 3.97 (s, 6H), 3.87 (s, 3H), 3.04-2.93 (m, 2H), 2.86-2.79 (m, 2H), 2.52-2.42 (m, 1H), 2.28-2.19 (m, 1H). |
| 21 | | (R)-3-(2,6-dichloro-3,5-dimethoxyphenyl)-7-(1-methyl-1H-pyrazol-4-yl)-1-(tetrahydrofuran-3-yl)-1,6-naphthyridin-2(1H)-one | MS m/z (ESI): 501.4, 503.4 [M + H]⁺. ¹H NMR (500 MHz, DMSO-d₆) δ 8.86 (s, 1H), 8.38 (s, 1H), 8.10 (d, J = 0.7 Hz, 1H), 8.06 (s, 1H), 7.95 (s, 1H), 7.01 (s, 1H), 5.94 (p, J = 8.0 Hz, 1H), 4.31 (q, J = 6.9 Hz, 1H), 4.08-3.98 (m, 2H), 3.97 (s, 6H), 3.93 (s, 3H), 3.85 (q, J = 7.5 Hz, 1H), 2.28 (q, J = 7.8, 7.3 Hz, 2H). |

| Example No. | Structural Formula | Chemical name | MS m/z (ESI): [M + H]+/1HNMR |
|---|---|---|---|
| 22 | 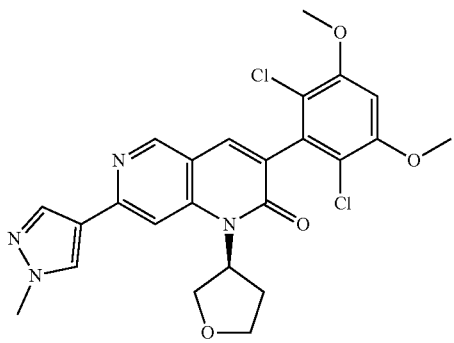 | (S)-3-(2,6-dichloro-3,5-dimethoxyphenyl)-7-(1-methyl-1H-pyrazol-4-yl)-1-(tetrahydrofuran-3-yl)-1,6-naphthyridin-2(1H)-one | MS m/z (ESI): 501.2, 503.2 [M + H]+. 1H NMR (500 MHz, CDCl3) δ 8.73 (s, 1H), 8.07 (s, 2H), 8.04 (s, 1H), 7.61 (s, 1H), 6.64 (s, 1H), 6.42-6.35 (m, 1H), 4.55 (t, J = 8.6 Hz, 1H), 4.28 (dd, J = 10.4, 4.0 Hz, 1H), 4.07 (t, J = 9.9 Hz, 1H), 4.00 (s, 3H), 3.96 (s, 6H), 3.86 (q, J = 9.4, 8.9 Hz, 1H), 2.47-2.36 (m, 2H). |
| 23 | 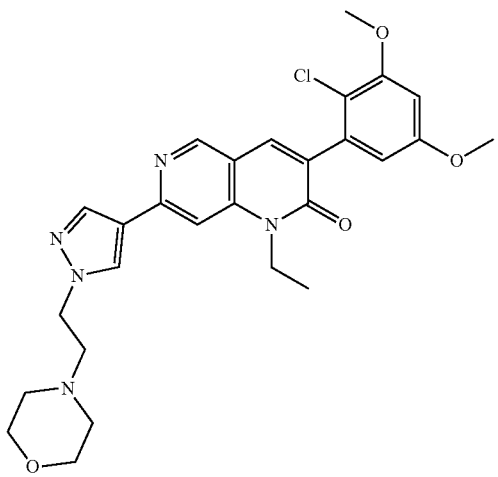 | 3-(2-chloro-3,5-dimethoxyphenyl)-1-ethyl-7-(1-(2-morpholinoethyl)-1H-pyrazol-4-yl)-1,6-naphthyridin-2(1H)-one | MS m/z (ESI): 524.2, 526.2 [M + H]+. 1H NMR (500 MHz, CDCl3) δ 8.79 (s, 1H), 8.32 (s, 1H), 8.14 (s, 1H), 8.12 (s, 1H, HCO2H), 7.74 (s, 1H), 7.35 (s, 1H), 6.58 (d, J = 2.8 Hz, 1H), 6.53 (d, J = 2.8 Hz, 1H), 4.76 (t, J = 6.1 Hz, 2H), 4.41 (q, J = 7.2 Hz, 2H), 3.94 (t, J = 4.7 Hz, 4H), 3.91 (s, 3H), 3.82 (s, 3H), 3.43 (t, J = 6.1 Hz, 2H), 2.92-2.87 (m, 4H), 1.43 (t, J = 7.1 Hz, 3H). |
| 24 | 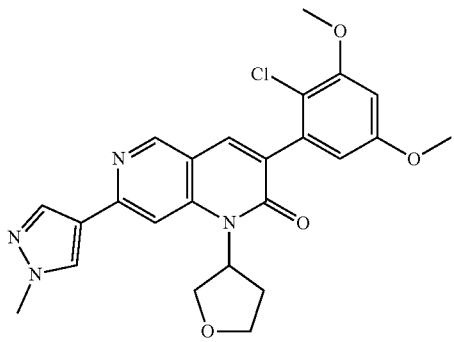 | 3-(2-chloro-3,5-dimethoxyphenyl)-7-(1-methyl-1H-pyrazol-4-yl)-1-(tetrahydrofuran-3-yl)-1,6-naphthyridin-2(1H)-one | MS m/z (ESI): 467.0, 469.0 [M + H]+. 1H NMR (500 MHz, CDCl3) δ 8.74 (s, 1H), 8.30 (s, 1H), 8.18 (s, 1H), 8.09 (s, 1H), 7.68 (s, 1H), 6.58 (d, J = 2.7 Hz, 1H), 6.50 (d, J = 2.5 Hz, 1H), 6.46-6.40 (m, 1H), 4.58 (t, J = 8.3 Hz, 1H), 4.27 (dd, J = 10.6, 3.9 Hz, 1H), 4.07 (t, J = 10.0 Hz, 1H), 4.00 (s, 3H), 3.92 (s, 3H), 3.88-3.84 (m, 1H), 3.82 (s, 3H), 2.46 (q, J = 10.3, 7.6 Hz, 1H), 2.38-2.27 (m, 1H). |

Example 25. Preparation of 3-(2,6-difluoro-3,5-dimethoxyphenyl)-1-ethyl-7-(1-methyl-1H-pyrazol-4-yl)-1,6-naphthyridin-2(1H)-one

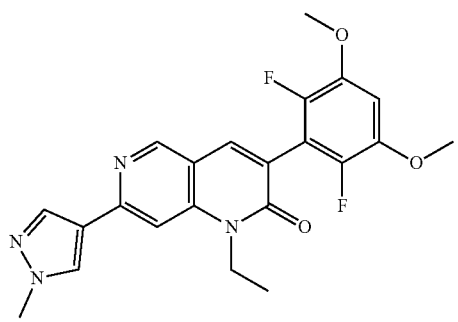

3-bromo-1-ethyl-7-(1-methyl-1H-pyrazol-4-yl)-1,6-naphthyridin-2(1H)-one (50 mg, 0.15 mmol) and 2-(2,6-difluoro-3,5-dimethoxyphenyl)-4,4,5,5-tetramethyl-1,3,2-dioxaborolan (180 mg, 0.60 mmol) were dissolved in a mixed solution of 1,4-dioxane (5 mL) and water (1 mL). Then chloro(2-dicyclohexylphosphino-2',4',6'-triisopropyl-1,1'-diphenyl)[2-(2'-amino-1,1'-diphenyl)]palladium(II) (12 mg, 0.015 mmol) and K$_3$PO$_4$ (127 mg, 0.60 mmol) were added. The reaction solution was stirred at 60° C. for 16 hours. Afterwards, the reaction solution was cooled down to room temperature, added with water and extracted with ethyl acetate. The organic phase was concentrated and the residue was separated by column chromatography (ethyl acetate/dichloromethane=0~50%) to obtain 3-(2,6-difluoro-3,5-dimethoxyphenyl)-1-ethyl-7-(1-methyl-1H-pyrazol-4-yl)-1,6-naphthyridin-2(1H)-one (38 mg, yield: 59%). MS m/z (ESI): 427.0 [M+H]$^+$.

$^1$H NMR (400 MHz, CDCl$_3$) δ 8.74 (s, 1H), 8.04 (d, J=4.5 Hz, 2H), 7.80 (s, 1H), 7.31 (s, 4H), 6.71 (t, J=8.0 Hz, 1H), 4.39 (q, J=72 Hz, 2H), 4.00 (s, 3H), 3.91 (s, 6H), 1.43 (t, J 7.1 Hz, 3H).

Examples 26-41 were Prepared According to the Synthesis Method of Example 25

| Example No. | Structural Formula | Chemical name | MS m/z (ESI): [M + H]$^+$/ $^1$HNMR |
|---|---|---|---|
| 26 | | 3-(2,6-difluoro-3,5-dimethoxyphenyl)-1-isopropyl-7-(1-methyl-1H-pyrazol-4-yl)-1,6-naphthyridin-2(1H)-one | MS m/z (ESI): 441.4 [M + H]$^+$. $^1$H NMR (400 MHz, CDCl$_3$) δ 8.73 (s, 1H), 8.22 (s, 1H), 8.03 (s, 1H), 7.75 (s, 1H), 7.53 (s, 1H), 6.71 (t, J = 8.0 Hz, 1H), 5.34-5.28 (m, 1H), 4.01 (s, 3H), 3.91 (s, 6H), 1.72 (t, J = 6.9 Hz, 6H). |
| 27 | | 1-(cyclopropylmethyl)-3-(2,6-difluoro-3,5-dimethoxyphenyl)-7-(1-methyl-1H-pyrazol-4-yl)-1,6-naphthyridin-2(1H)-one | MS m/z (ESI): 453.3 [M + H]$^+$. $^1$H NMR (400 MHz, CDCl$_3$) δ 8.76 (s, 1H), 8.17 (br s, 1H), 8.05 (s, 1H), 7.81 (s, 1H), 7.45 (s, 1H), 6.71 (t, J = 8.0 Hz, 1H), 4.29 (d, J = 7.0 Hz, 2H), 4.01 (s, 3H), 3.91 (s, 6H), 1.30-1.25 (m, 1H), 0.63-0.56 (m, 4H). |
| 28 | | 3-(2,6-difluoro-3,5-dimethoxyphenyl)-7-(1-methyl-1H-pyrazol-4-yl)-1-(tetrahydrofuran-3-yl)-1,6-naphthyridin-2(1H)-one | MS m/z (ESI): 469.0 [M + H]$^+$. $^1$H NMR (500 MHz, CDCl$_3$) δ 8.74 (s, 1H), 8.10 (s, 2H), 8.08 (s, 1H), 7.76 (s, 1H), 6.72 (t, J = 7.9 Hz, 1H), 6.48-6.37 (m, 1H), 4.56 (t, J = 8.2 Hz, 1H), 4.28 (dd, J = 10.6, 3.9 Hz, 1H), 4.06 (t, J = 10.0 Hz, 1H), 4.00 (s, 3H), 3.91 (s, 6H), 3.90-3.80 (m, 1H), 2.50-2.31 (m, 2H). |

-continued

| Example No. | Structural Formula | Chemical name | MS m/z (ESI): [M + H]+/ 1HNMR |
|---|---|---|---|
| 29 | | 3-(2,6-difluoro-3,5-dimethoxyphenyl)-1-ethyl-7-(1-(2-morpholinoethyl)-1H-pyrazol-4-yl)-1,6-naphthyridin-2(1H)-one | MS m/z (ESI): 526.4 [M + H]+. 1H NMR (400 MHz, CDCl$_3$) δ 8.74 (s, 1H), 8.17 (s, 1H), 8.06 (t, 1H), 7.81 (s, 1H), 7.32 (s, 1H), 6.71 (t, J = 8.0 Hz, 1H), 4.40 (q, J = 7.1, 6.3 Hz, 4H), 3.91 (s, 6H), 3.79-3.72 (m, 4H), 2.98 (s, 2H), 2.58 (s, 4H), 1.43 (t, J = 7.1 Hz, 3H). |
| 30 | | 3-(2,6-difluoro-3,5-dimethoxyphenyl)-1-isopropyl-7-(1-(2-morpholinoethyl)-1H-pyrazol-4-yl)-1,6-naphthyridin-2(1H)-one | MS m/z (ESI): 540.5 [M + H]+. 1H NMR (400 MHz, CDCl$_3$) δ 8.71 (s, 1H), 8.15 (s, 1H), 8.04 (s, 1H), 7.76 (s, 1H), 7.51 (s, 1H), 6.70 (t, J = 8.0 Hz, 1H), 5.31 (s, 1H), 4.37 (t, J = 6.5 Hz, 2H), 3.91 (s, 6H), 3.74 (t, J = 4.6 Hz, 4H), 2.95 (t, J = 6.6 Hz, 2H), 2.56 (t, J = 4.6 Hz, 4H), 1.72 (d, J = 6.9 Hz, 6H). |
| 31 | | 1-(cyclopropylmethyl)-3-(2,6-difluoro-3,5-dimethoxyphenyl)-7-(1-(2-morpholinoethyl)-1H-pyrazol-4-yl)-1,6-naphthyridin-2(1H)-one | MS m/z (ESI): 552.4 [M + H]+. 1H NMR (400 MHz, CDCl3) δ 8.73 (s, 1H), 8.23 (s, 1H), 8.07 (s, 1H), 7.80 (s, 1H), 7.43 (s, 1H), 6.71 (t, J = 7.9 Hz, 1H), 4.49 (s, 2H), 4.28 (d, J = 6.9 Hz, 2H), 3.91 (s, 6H), 3.84-3.74 (m, 4H), 3.08 (s, 2H), 2.65 (s, 4H), 1.33-1.23 (m, 1H), 0.63-0.55 (m, 4H). |

-continued

| Example No. | Structural Formula | Chemical name | MS m/z (ESI): [M + H]+/ 1HNMR |
|---|---|---|---|
| 32 | | 1-(5-(3-(2,6-difluoro-3,5-dimethoxyphenyl)-2-oxo-1-(tetrahydrofuran-3-yl)-1,2-dihydro-1,6-naphthyridin-7-yl)pyridin-2-yl)cyclobutane-1-carbonitrile | MS m/z (ESI): 544.8 [M + H]+. 1H NMR (500 MHz, CDCl3) δ 9.40 (s, 1H), 8.96 (s, 1H), 8.49 (s, 2H), 7.88 (s, 1H), 7.71 (s, 1H), 6.74 (s, 1H), 6.52 (brs. 1H), 4.59 (t, J = 8.3 Hz, 1H), 4.31 (dd, J = 10.6, 3.9 Hz, 1H), 4.10 (t, J = 10.0 Hz, 1H), 3.93 (s, 6H), 3.86 (s, 1H), 2.98 (dt, J = 12.4, 9.1 Hz, 2H), 2.86-2.76 (m, 2H), 2.52-2.36 (m, 3H), 2.24-2.20 (m, 1H) |
| 33 | | 1-cyclopentyl-3-(2,6-difluoro-3,5-dimethoxyphenyl)-7-(1-methyl-1H-pyrazol-4-yl)-1,6-naphthyridin-2(1H)-one | MS m/z (ESI): 467.2 [M + H]+. 1H NMR (500 MHz, CDCl3) δ 8.75 (s, 1H), 8.41 (s, 1H), 8.02 (s, 1H), 7.76 (s, 1H), 7.51 (s, 1H), 6.72 (t, J = 8.0 Hz, 1H), 5.53-5.45 (m, 1H), 4.02 (s, 3H), 3.91 (s, 6H), 2.35-2.28 (m, 2H), 2.18-2.07 (m, 2H), 2.12-2.04 (m, 2H), 1.86-1.80 (m, 2H). |
| 34 | | 1-cyclopentyl-3-(2,6-difluoro-3,5-dimethoxyphenyl)-7-(1-(2-morpholinoethyl)-1H-pyrazol-4-yl)-1,6-naphthyridin-2(1H)-one | MS m/z (ESI): 565.8 [M + H]+. 1H NMR (500 MHz, CDCl3) δ 8.72 (s, 1H), 8.13 (s, 1H), 8.02 (s, 1H), 7.76 (s, 1H), 7.47 (s, 1H), 6.70 (t, J = 8.0 Hz, 1H), 5.57-5.50 (m, 1H), 4.34 (t, J = 6.6 Hz, 2H), 3.91 (s, 6H), 3.72 (t, J = 4.6 Hz, 4H), 3.71-3.64 (m, 4H), 2.91 (t, J = 6.5 Hz, 2H), 2.36-2.30 (m, 2H), 2.18-2.11 (m, 2H), 2.10-2.03 (m, 2H), 1.84-1.78 (m, 2H). |

-continued

| Example No. | Structural Formula | Chemical name | MS m/z (ESI): [M + H]+/ 1HNMR |
|---|---|---|---|
| 35 | | 3-(2,6-difluoro-3,5-dimethoxyphenyl)-7-(1-(2-morpholinoethyl)-1H-pyrazol-4-yl)-1-(tetrahydrofuran-3-yl)-1,6-naphthyridin-2(1H)-one | MS m/z (ESI): 567.8 [M + H]+. 1H NMR (500 MHz, CDCl3) δ 8.74 (s, 1H), 8.17 (br s, 1H), 8.10 (s, 1H), 8.09 (s, 1H), 7.77 (s, 1H), 6.72 (t, J = 8.0 Hz, 1H), 6.47-6.39 (m, 1H), 4.57 (t, J = 8.8 Hz, 1H),4.42 (br s, 2H), 4.28 (m, 1H), 4.05 (t, J = 10.0 Hz, 1H), 3.92 (s, 6H), 3.87-3.83 (m, 1H), 3.85-3.61 (m, 4H), 2.96 (brs, 2H), 2.53 (br s, 4H), 2.41 (m, 2H). |
| 36 | | 3-(2,6-difluoro-3,5-dimethoxyphenyl)-7-(pyridin-3-yl)-1-(tetrahydrofuran-3-yl)-1,6-naphthyridin-2(1H)-one | MS m/z (ESI): 466.2 [M + H]+. 1H NMR (500 MHz, CDCl3) δ 9.33 (s, 1H), 8.83 (s, 1H), 8.67-8.62 (m, 1H), 8.43 (dt, J = 7.9, 1.9 Hz, 1H), 8.38 (s, 1H), 7.78 (s, 1H), 7.49-7.44 (m, 1H), 6.66 (t, J = 8.0 Hz, 1H), 6.41 (qd, J = 6.4, 3.7 Hz, 1H), 4.51 (t, J = 8.6 Hz, 1H), 4.23 (dd, J = 10.7, 3.8 Hz, 1H), 4.06-3.98 (m, 1H), 3.85 (s, 6H), 3.78 (ddd, J = 11.0, 9.5, 6.5 Hz, 1H), 2.42 (dddd, J = 12.4, 10.3, 6.5, 1.9 Hz, 1H), 2.32 (ddt, J = 13.1, 11.1, 8.1 Hz, 1H). |
| 37 | | 3-(2,6-difluoro-3,5-dimethoxyphenyl)-7-(4-methylpyridin-3-yl)-1-(tetrahydrofuran-3-yl)-1,6-naphthyridin-2(1H)-one | MS m/z (ESI): 480.2 [M + H]+. 1H NMR (500 MHz, CDCl3) δ 8.86 (s, 1H), 8.55 (s, 1H), 8.53 (d, J = 5.1 Hz, 1H), 7.96 (s, 1H), 7.81 (s, 1H), 7.46 (d, J = 5.1 Hz, 1H), 6.67 (t, J = 8.0 Hz, 1H), 6.40-6.30 (m, 1H), 4.37 (td, J = 8.8, 8.4, 2.0 Hz, 1H), 4.16 (dd, J = 10.5, 4.1 Hz, 1H), 3.98 (t, J = 9.9 Hz, 1H), 3.86 (s, 6H), 3.72 (ddd, J = 10.9, 9.4, 6.3 Hz, 1H), 2.46 (s, 3H), 2.38 (dddd, J = 12.4, 10.0, 6.2, 1.9 Hz, 1H), 2.26 (ddt, J = 12.9, 10.8, 8.0 Hz, 1H). |
| 38 | | 7-(6-(2-oxa-5-azabicyclo[2.2.1]heptan-5-yl)pyridin-3-yl)-3-(2,6-difluoro-3,5-dimethoxyphenyl)-1-(tetrahydrofuran-3-yl)-1,6-naphthyridin-2(1H)-one | MS m/z (ESI): 563.2 [M + H]+. 1H NMR (500 MHz, CDCl3) δ 8.87 (s, 1H), 8.74 (s, 1H), 8.23 (s, 1H), 8.16 (s, 1H), 7.72 (s, 1H), 6.65 (t, J = 8.0 Hz, 1H), 6.47 (s, 1H), 6.37 (dd, J = 12.3, 4.6 Hz, 1H), 4.70 (s, 1H), 4.51 (t, J = 8.6 Hz, 1H), 4.22 (dd, J = 10.5, 4.0 Hz, 1H), 3.99 (t, J = 10.0 Hz, 1H), 3.88 (s, 2H), 3.85 (s, 6H), 3.82-3.75 (m, 2H), 3.54 (s, 1H), 3.46-3.41 (m, 1H), 2.39-2.33 (m, 2H), 2.00-1.94 (m, 2H). |

-continued

| Example No. | Structural Formula | Chemical name | MS m/z (ESI): [M + H]⁺/ ¹HNMR |
|---|---|---|---|
| 39 | | 3-(2,6-difluoro-3,5-dimethoxyphenyl)-7-(pyridin-4-yl)-1-(tetrahydrofuran-3-yl)-1,6-naphthyridin-2(1H)-one | MS m/z (ESI): 466.4 [M + H]⁺. ¹H NMR (500 MHz, CDCl₃) δ 8.92 (s, 1H), 8.79 (d, J = 5.0 Hz, 2H), 8.54 (s, 1H), 8.09 (d, J = 5.5 Hz, 2H), 7.86 (s, 1H), 6.74 (t, J = 8.0 Hz, 1H), 6.54-6.48 (m, 1H), 4.60 (t, J = 8.9 Hz, 1H), 4.33-4.30 (m, 1H), 4.10 (t, J = 10.1 Hz, 1H), 3.93 (s, 6H), 3.90-3.83 (m, 1H), 2.54-2.28 (m, 1H), 2.41-2.33 (m, 1H). |
| 40 | | 2-(5-(3-(2,6-difluoro-3,5-dimethoxyphenyl)-2-oxo-1-(tetrahydrofuran-3-yl)-1,2-dihydro-1,6-naphthyridin-7-yl)pyridin-2-yl)-2-methylpropanenitrile | MS m/z (ESI): 533.4 [M + H]⁺. ¹H NMR (500 MHz, CDCl₃) δ 9.35-9.31 (m, 1H), 8.92 (s, 1H), 8.51 (dd, J = 8.3, 2.4 Hz, 1H), 8.47 (s, 1H), 7.85 (s, 1H), 7.76 (d, J = 8.2 Hz, 1H), 6.74 (t, J = 8.0 Hz, 1H), 6.56-6.45 (m, 1H), 4.60 (t, J = 8.8 Hz, 1H), 4.30 (dd, J = 10.7, 3.7 Hz, 1H), 4.08 (t, J = 10.0 Hz, 1H), 3.93 (s, 6H), 3.89-3.81 (m, 1H), 2.55-2.45 (m, 1H), 2.42-2.34 (m, 1H), 1.83 (s, 6H). |
| 41 | | 2-(4-(3-(2,6-difluoro-3,5-dimethoxyphenyl)-2-oxo-1-(tetrahydrofuran-3-yl)-1,2-dihydro-1,6-naphthyridin-7-yl)phenyl)acetonitrile | MS m/z (ESI): 504.5 [M + H]⁺. ¹H NMR (500 MHz, CDCl₃) δ 8.92 (s, 1H), 8.41 (s, 1H), 8.17 (d, J = 7.9 Hz, 2H), 7.85 (s, 1H), 7.52 (d, J = 7.8 Hz, 2H), 6.73 (t, J = 7.9 Hz, 1H), 6.54-6.45 (m, 1H), 4.57 (t, J = 8.7 Hz, 1H), 4.32 (m, 1H), 4.10 (t, J = 10.0 Hz, 1H), 3.93 (s, 6H), 3.89-3.86 (m, 1H), 3.85 (s, 2H), 2.52-2.45 (m, 1H), 2.45-2.35 (m, 1H). |

Example 42. Preparation of 3-(2,6-dichloro-3,5-dimethoxyphenyl)-1-ethyl-7-(3-methyl-1-(2-morpholinoethyl)-1H-pyrazol-4-yl)-1,6-naphthyridin-2(1H)-one

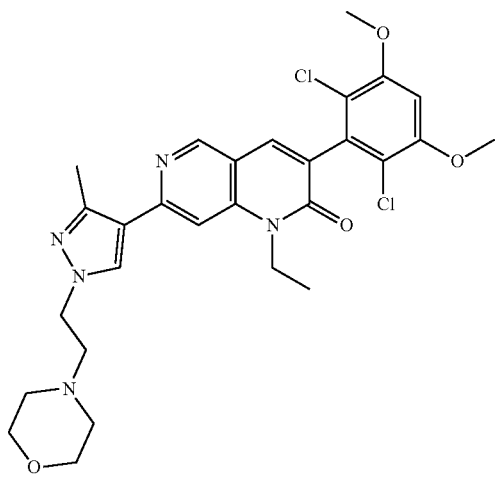

Step 1: Synthesis of 3-(2,6-dichloro-3,5-dimethoxyphenyl)-1-ethyl-7-(3-methyl-1H-pyrazol-4-yl)-1,6-naphthyridin-2 (1H)-one

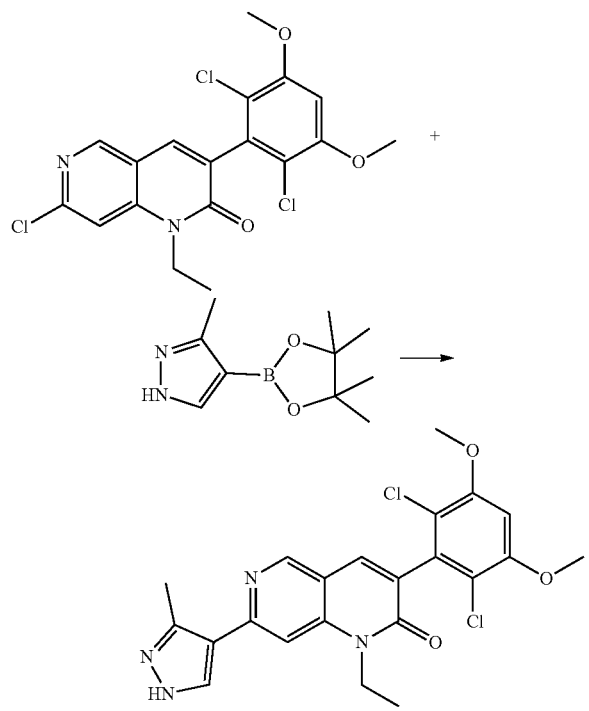

An aqueous solution of [1,1'-bis(biphenylphosphino)ferrocene]palladium bichloride (80 mg, 0.11 mmol) and Na₂CO₃ (3.0 mL, 6.0 mmol, 2N) was added into a solution of 7-chloro-3-(2,6-di chloro-3,5-dimethoxyphenyl)-1-ethyl-1,6-naphthyridin-2(1H)-one (450 mg, 1.09 mmol) and 3-meth ylpyrazol-4-borate pinacol ester (340 mg, 1.63 mmol) in 1,4-dioxane (15 mL). The reaction solut ion was stirred at 90° C. for 16 hours. Afterwards, the reaction solution was cooled down to roo m temperature, added with water and extracted with ethyl acetate. The organic phase was conce ntrated and the residue was separated by column chromatography (MeOH/DCM=0~5%) to o btain 3-(2,6-dichloro-3,5-dimethoxyphenyl)-1-ethyl-7-(3-methyl-1H-pyrazol-4-yl)-1,6-naphthyridin-2(1H)-one (310 mg, yield: 62%). MS m/z (ESI): 459.0, 461.0[M+H]⁺.

Step 2: Synthesis of 3-(2,6-dichloro-3,5-dimethoxyphenyl)-1-ethyl-7-(3-methyl-1-(2-morph olinoethyl)-1H-pyrazol-4-yl)-1,6-naphthyridin-2(1H)-one

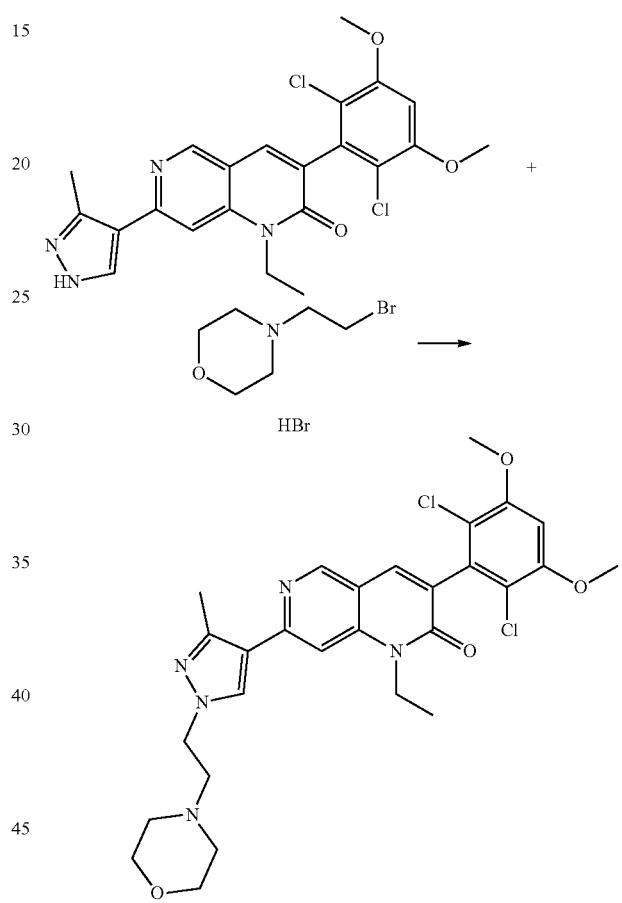

Cesium carbonate (355 mg, 1.09 mmol) was added into a solution of 3-(2,6-dichloro-3,5-dimethoxyphenyl)-1-ethyl-7-(3-methyl-1H-pyrazol-4-yl)-1,6-naphthyridin-2(1H)-one (100 mg, 0.218 mmol) and 4-(2-bromoethyl) morpholine bromide (119 mg, 0.435 mmol) in DMF (5 mL). The reaction solution was stirred at 90° C. for 2 hours. Then the reaction solution was added with saturated salt solution, filtered and concentrated. The residue was separated by column chromatography (MeOH/DCM=0~8%) to obtain crude product (80 mg). The crude product was further separated by SFC to obtain 3-(2,6-dichloro-3,5-dimethoxyphenyl)-1-ethyl-7-(3-methyl-1-(2-morpholinoethyl)-1H-pyrazol-4-yl)-1,6-naphthyridin-2(1H)-one. MS m/z (ESI): 572, 574[M+H]⁺.

¹H NMR (400 MHz, CDCl₃) δ 8.77 (s, 1H), 8.03 (s, 1H), 7.65 (s, 1H), 7.33 (s, 1H), 6.64 (s, 1H), 4.39 (q, J=7.1 Hz, 2H), 4.25 (t, J=6.7 Hz, 2H), 3.96 (s, 6H), 3.71 (t, J=4.6 Hz, 4H), 2.87 (t, J=6.8 Hz, 2H), 2.60 (s, 3H), 2.52 (t, J=4.7 Hz, 4H), 1.43 (t, J=7.1 Hz, 3H).

Examples 43-52 were Prepared According to the Synthesis Method of Example 42

| Example No. | Structural Formula | Chemical name | MS m/z (ESI): [M + H]+/1HNMR |
|---|---|---|---|
| 43 | | 2-(4-(3-(2,6-dichloro-3,5-dimethoxyphenyl)-1-ethyl-2-oxo-1,2-dihydro-1,6-naphthyridin-7-yl)-3-methyl-1H-pyrazol-1-yl)acetonitrile | MS m/z (ESI): 498.2, 500.2 [M + H]+. 1H NMR (400 MHz, CDCl3) δ 8.79 (s, 1H), 8.10 (s, 1H), 7.67 (s, 1H), 7.35 (s, 1H), 6.64 (s, 1H), 5.08 (s, 2H), 4.39 (q, J = 7.1 Hz, 2H), 3.95 (s, 6H), 2.61 (s, 3H), 1.43 (t, J = 7.1 Hz, 3H). |
| 44 | | 3-(4-(3-(2,6-dichloro-3,5-dimethoxyphenyl)-1-ethyl-2-oxo-1,2-dihydro-1,6-naphthyridin-7-yl)-3-methyl-1H-pyrazol-1-yl)propanenitrile | MS m/z (ESI): 512.4, 514.4 [M + H]+. 1H NMR (400 MHz, CDCl3) δ 8.81 (s, 1H), 8.34 (s, 1H), 7.67 (s, 1H), 7.37 (s, 1H), 6.65 (s, 1H), 4.41 (dt, J = 13.2, 6.8) Hz, 4H), 3.96 (s, 6H), 3.02 (t, J = 6.6 Hz, 2H), 2.61 (s, 3H), 1.44 (t, J = 7.0 Hz, 3H). |
| 45 | | 3-(2,6-dichloro-3,5-dimethoxyphenyl)-7-(1-(2-(dimethylamino)ethyl)-3-methyl-1H-pyrazol-4-yl)-1-ethyl-1,6-naphthyridin-2(1H)-one | MS m/z (ESI): 530.4, 532.4 [M + H]+. 1H NMR (400 MHz, CDCl3) δ 8.77 (s, 1H), 8.11 (s, 1H), 7.65 (s, 1H), 7.33 (s, 1H), 6.65 (s, 1H), 4.49 (t, J = 6.5 Hz, 2H), 4.39 (q, J = 7.1 Hz, 2H), 3.96 (s, 6H), 3.18 (s, 2H), 2.60 (s, 3H), 2.51 (s, 6H), 1.43 (t, J = 7.0 Hz, 3H). |

| Example No. | Structural Formula | Chemical name | MS m/z (ESI): [M + H]+/1HNMR |
|---|---|---|---|
| 46 | 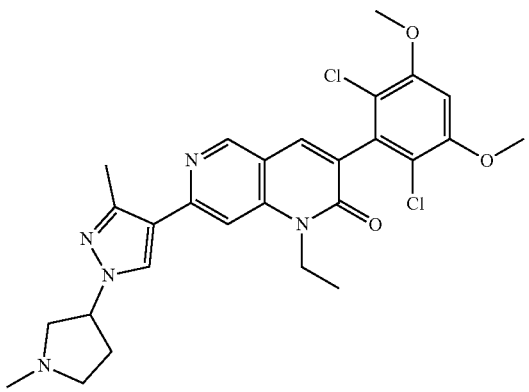 | 3-(2,6-dichloro-3,5-dimethoxyphenyl)-1-ethyl-7-(3-methyl-1-(1-methylpyrrolidin-3-yl)-1H-pyrazol-4-yl)-1,6-naphthyridin-2(1H)-one | MS m/z (ESI): 542.4, 544.4 [M + H]+. 1H NMR (400 MHz, CDCl3) δ 8.80 (s, 1H), 8.16 (s, 1H), 7.67 (s, 1H), 7.32 (s, 1H), 6.65 (s, 1H), 5.26-5.17 (m, 1H), 4.42-4.29 (m, 2H), 3.96 (s, 6H), 3.62-3.50 (m, 2H), 3.12-3.09 (m, 2H), 2.88-2.80 (m, 1H), 2.59 (s, 3H), 2.47-2.29 (m, 1H), 2.01 (s, 3H), 1.43 (t, J = 6.8 Hz, 3H). |
| 47 | 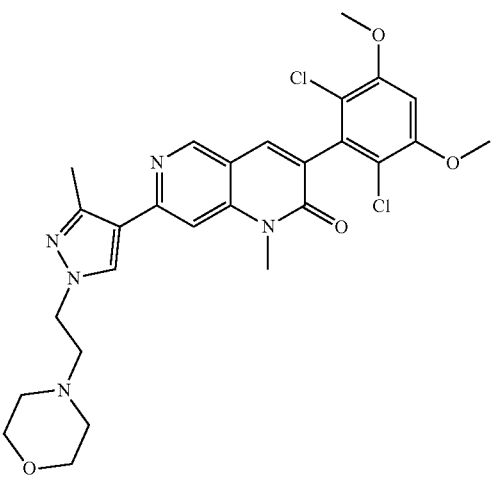 [SMILES: COc1cc(OC)c(Cl)c(-c2cc3cnc(-c4cn(CCN5CCOCC5)nc4C)cc3n(C)c2=O)c1Cl] | 3-(2,6-dichloro-3,5-dimethoxyphenyl)-1-methyl-7-(3-methyl-1-(2-morpholinoethyl)-1H-pyrazol-4-yl)-1,6-naphthyridin-2(1H)-one | MS m/z (ESI): 558.0, 560.0 [M + H]+. 1H NMR (500 MHz, CDCl3) δ 8.77 (s, 1H), 8.05 (s, 1H), 7.65 (s, 1H), 7.31 (s, 1H), 6.65 (s, 1H), 4.31 (s, 2H), 3.96 (s, 6H), 3.77 (s, 3H), 3.75 (s, 4H), 2.95 (s, 2H), 2.61 (s, 3H), 2.58 (s, 4H). |
| 48 | 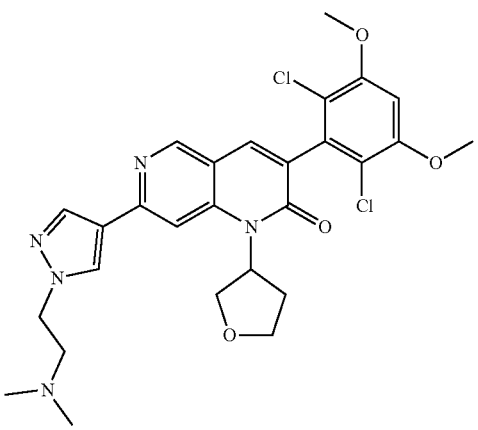 | 3-(2,6-dichloro-3,5-dimethoxyphenyl)-7-(1-(2-(dimethylamino)ethyl)-1H-pyrazol-4-yl)-1-(tetrahydrofuran-3-yl)-1,6-naphthyridin-2(1H)-one | MS m/z (ESI): 558.2, 560.2 [M + H]+. 1H NMR (500 MHz, CDCl3) δ 8.73 (s, 1H), 8.23 (s, 1H), 8.13 (s, 1H), 8.08 (s, 1H), 7.61 (s, 1H), 6.65 (s, 1H), 6.36 (d, J = 8.9 Hz, 1H), 4.68-4.62 (m, 1H), 4.60-4.54 (m, 1H), 4.27 (dd, J = 10.3, 4.2 Hz, 1H), 4.07 (t, J = 9.9 Hz, 1H), 3.96 (s, 6H), 3.86 (q, J = 9.2 Hz, 2H), 3.35 (s, 2H), 2.57 (s, 6H), 2.45-2.39 (m, 2H). |

| Example No. | Structural Formula | Chemical name | MS m/z (ESI): [M + H]+/1HNMR |
|---|---|---|---|
| 49 | 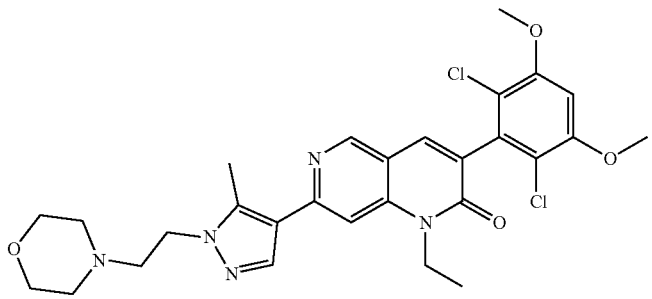 [SMILES: CCn1c(=O)c(-c2c(Cl)c(OC)cc(OC)c2Cl)cc2cnc(-c3cnn(CCN4CCOCC4)c3C)cc21] | 3-(2,6-dichloro-3,5-dimethoxyphenyl)-1-ethyl-7-(5-methyl-1-(2-morpholinoethyl)-1H-pyrazol-4-yl)-1,6-naphthyridin-2(1H)-one | MS m/z (ESI): 572.4, 574.4 [M + H]+. 1H NMR (400 MHz, CDCl3) δ 8.79 (s, 1H), 7.90 (s, 1H), 7.66 (s, 1H), 7.30 (s, 1H), 6.64 (s, 1H), 4.39 (m, 2H), 4.27 (t, J = 7.0 Hz, 2H), 3.95 (s, 6H), 3.71 (t, J = 4.6 Hz, 4H), 2.84 (t, J = 6.9 Hz, 2H), 2.70 (s, 3H), 2.53 (t, J = 4.6 Hz, 4H), 1.42 (t, J = 7.0 Hz, 3H). |
| 50 | 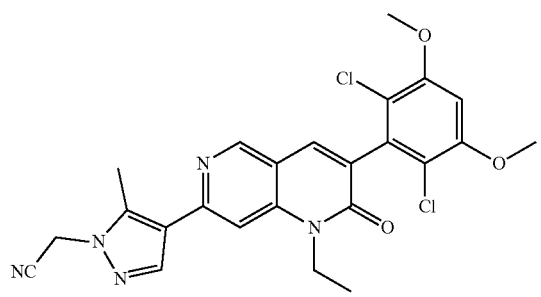 [SMILES: CCn1c(=O)c(-c2c(Cl)c(OC)cc(OC)c2Cl)cc2cnc(-c3cnn(CC#N)c3C)cc21] | 2-(4-(3-(2,6-dichloro-3,5-dimethoxyphenyl)-1-ethyl-2-oxo-1,2-dihydro-1,6-naphthyridin-7-yl)-5-methyl-1H-pyrazol-1-yl)acetonitrile | MS m/z (ESI): 498.2, 500.3 [M + H]+. 1H NMR (400 MHz, CDCl3) δ 8.81 (s, 1H), 7.95 (s, 1H), 7.67 (s, 1H), 7.31 (s, 1H), 6.64 (s, 1H), 5.11 (s, 2H), 4.39 (m, 2H), 3.95 (s, 6H), 2.78 (s, 3H), 1.42 (t, J = 7.1 Hz, 3H). |
| 51 | 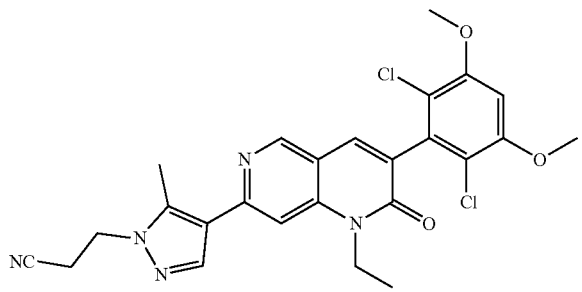 [SMILES: CCn1c(=O)c(-c2c(Cl)c(OC)cc(OC)c2Cl)cc2cnc(-c3cnn(CCC#N)c3C)cc21] | 3-(4-(3-(2,6-dichloro-3,5-dimethoxyphenyl)-1-ethyl-2-oxo-1,2-dihydro-1,6-naphthyridin-7-yl)-5-methyl-1H-pyrazol-1-yl)propanenitrile | MS m/z (ESI): 512.4, 514.4 [M + H]+. 1H NMR (400 MHz, CDCl3) δ 8.84 (s, 1H), 7.99 (s, 1H), 7.67 (s, 1H), 7.32 (s, 1H), 6.65 (s, 1H), 4.48-4.37 (m, 4H), 3.96 (s, 6H), 3.02 (t, J = 6.6 Hz, 2H), 2.75 (s, 3H), 1.42 (d, J = 7.0 Hz, 3H). |
| 52 | 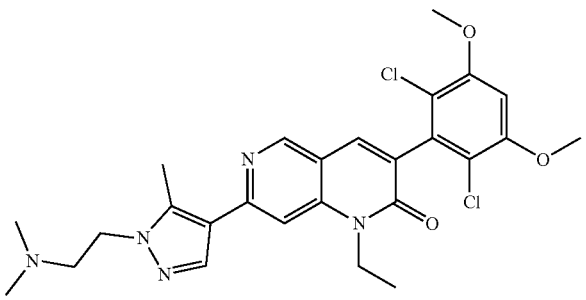 | 3-(2,6-dichloro-3,5-dimethoxyphenyl)-7-(1-(2-(dimethylamino)ethyl)-5-methyl-1H-pyrazol-4-yl)-1-ethyl-1,6-naphthyridin-2(1H)-one | MS m/z (ESI): 530.4, 532.4 [M + H]+. 1H NMR (400 MHz, CDCl3) δ 8.80 (s, 1H), 7.92 (s, 1H), 7.66 (s, 1H), 7.29 (s, 1H), 6.65 (s, 1H), 4.50 (t, J = 6.8 Hz, 2H), 4.39 (q, J = 7.1 Hz, 2H), 3.96 (s, 6H), 3.19 (t, J = 6.5 Hz, 2H), 2.75 (s, 3H), 2.54 (s, 6H), 1.42 (t, J = 7.1 Hz, 3H). |

Biological Test Evaluation

I. In Vitro Biochemical Kinase Assay of FGFR 1~3

Caliper Assay was used in the present invention to determine the inhibitory activities of the compounds against FGFR1, FGFR2, and FGFR3. The specific experimental procedure was as follows:

1. The kinase reaction in the present invention was carried out in 384-well plates, the kinase(Carna) at a certain concentration and ATP at a certain concentration and 1 µM of peptide FAM-P22 (GL Biochem, Cat. No. 112393)) was incubated to react for a certain time at 28° C. in a reaction system consisting of 50 mM HEPES, pH47.5, 0.0015% Brij-35 and basic kinase buffer; for FGFR1, the enzyme concentration was 0.25 nM and ATP concentration was 382 µM and the reaction time was 20 minutes; for FGFR2, the enzyme concentration was 2.5 nM, ATP concentration was 1 µM, and the reaction time was 40 minutes; for FGFR3, the enzyme concentration was 8 nM, ATP concentration was 4.7 µM, and the reaction time was 30 minutes:

2. The reaction was terminated with a stop solution (100 mM HEPES, pH 7.5, 0.2% Caliper coating, reagent, 50 mM EDTA and 0.015% Brij35);

3. The plate with the terminated kinase reaction was transferred to the Caliper workstation to read the data;

4. the phosphorylated and unphosphorylated peptides were separated by the Caliper microfluid migration shift technique, and the analyte was transferred by a constant buffer flow through the chip, the migration of the substrate peptide was monitored by the labeled fluorescent signal, and the kinase activity was calculated by the amount of the phosphate-based peptide formed.

5. $IC_{50}$ was determined by non-linear regression analysis of percent inhibition at different concentration level of the compound. The enzymatic activities of the compound in the specific examples were shown in Table 1.

TABLE 1

Enzymatic activity test results

| Example No. | Enzymatic activity $IC_{50}$(nM) | | | Example No. | Enzymatic activity $IC_{50}$(nM) | | |
|---|---|---|---|---|---|---|---|
| | FGFR1 | FGFR2 | FGFR3 | | FGFR1 | FGFR2 | FGFR3 |
| 1 | +++ | +++++ | NT | 27 | NT | NT | NT |
| 2 | +++ | ++++ | ++ | 28 | +++++ | +++++ | NT |
| 3 | ++++ | +++++ | NT | 29 | ++++ | +++++ | NT |
| 4 | +++ | +++++ | NT | 30 | +++++ | +++++ | NT |
| 5 | ++ | +++ | NT | 31 | NT | NT | NT |
| 6 | NT | NT | NT | 32 | ++++ | +++++ | NT |
| 7 | +++++ | +++++ | NT | 33 | +++++ | +++++ | NT |
| 8 | NT | NT | NT | 34 | NT | NT | NT |
| 9 | +++ | +++++ | NT | 35 | NT | NT | NT |
| 10 | +++ | +++++ | +++++ | 36 | NT | NT | NT |
| 11 | +++ | +++++ | NT | 37 | NT | NT | NT |
| 12 | NT | NT | NT | 38 | NT | NT | NT |
| 13 | ++ | ++++ | NT | 39 | NT | NT | NT |
| 14 | NT | NT | NT | 40 | ++++ | +++++ | NT |
| 15 | ++ | ++++ | ++ | 41 | NT | NT | NT |
| 16 | ++ | +++ | NT | 42 | NT | NT | NT |
| 17 | NT | NT | NT | 43 | NT | NT | NT |
| 18 | NT | NT | NT | 44 | NT | NT | NT |
| 19 | NT | NT | NT | 45 | NT | NT | NT |
| 20 | NT | NT | NT | 46 | +++ | +++++ | NT |
| 21 | ++++ | +++++ | +++++ | 47 | NT | NT | NT |
| 22 | +++++ | +++++ | NT | 48 | +++ | +++++ | NT |
| 23 | NT | NT | NT | 49 | NT | NT | NT |
| 24 | NT | NT | NT | 50 | NT | NT | NT |
| 25 | +++++ | +++++ | NT | 51 | NT | NT | NT |
| 26 | NT | NT | NT | 52 | NT | NT | NT |

Note
1. "NT", i.e., "Not Tested", means that the compound was not tested.
2. "+++++" means biological activity $IC_{50} \leq 5.0$ nM;
"++++" means 5.0 nM < biological activity $IC_{50} \leq 10.0$ nM;
"+++" means 10.0 nM < biological activity $IC_{50} \leq 50.0$ nM;
"++" means 50.0 nM < biological activity $IC_{50} \leq 500.0$ nM;
"+" means 500.0 nM < biological activity $IC_{50}$.

II. Cell Proliferation Assay (Cell Titer Glo(CTG) Assay)

The FGFR signal pathway dependent inhibitory effect of the compound in the present invention on cell proliferation was assessed by survival test using CTG reagent (Promega, 4G7573). Cell lines representative of a variety of tumor types, including H1581 lung cancer cells (FGFR1 gene amplification), Snu-16 gastric cancer cells (FGFR2 gene amplification), and RT112 bladder carcinoma cells (FGFR3-TACC3 fusion) from Nanjing Cobioer Biosciences, were selected for the assay. The specific experimental procedure was as follows:

1. 90 µL of cells were seeded into a 96-well plate processed with TCM (Costar 43904), and incubated overnight at 37° C. in a 5% $CO_2$ incubator; afterwards, 10 µL of the culture medium containing the compound at 10 fold of its final concentration was added.
2. The dose-dependent effect was evaluated by a serial dilution of the test compound, starting from 10 µM or a lower concentration.
3. The cells were incubated at 37° C. under 5% $C_{O2}$ for 3 days, then added 50 µL CTG, and read the data with Envision (Pelkin Elmer) to quantify the ATP level in the cells. The ATP levels in cells with treatment of inhibitor at a variety of concentrations were compared with those in cells of the control group (in which DMSO was added into the medium) to evaluate the compound percent inhibition of cell proliferation/survival.
4. The compound half growth inhibitory concentration ($IC_{50}$) was determined in Graphpad Prism by 4-parameter curve fitting. The cellular activities of the compound in specific examples were shown in Table 2.

TABLE 2

Cellular Activity test results

| Example No. | Cellular $IC_{50}$ (nM) | | | Example No. | Cellular $IC_{50}$ (nM) | | |
|---|---|---|---|---|---|---|---|
| | Sun16 | H1581 | RT112 | | Sun16 | H1581 | RT112 |
| 1 | NT | NT | NT | 27 | NT | NT | NT |
| 2 | +++ | ++ | ++ | 28 | +++++ | +++ | +++++ |
| 3 | NT | NT | NT | 29 | +++ | ++ | NT |
| 4 | ++ | ++ | NT | 30 | +++++ | +++ | NT |
| 5 | +++ | ++ | NT | 31 | +++ | ++ | NT |
| 6 | NT | NT | NT | 32 | 10.7 | ++ | 2.5 |
| 7 | ++++ | +++ | NT | 33 | +++++ | +++ | NT |
| 8 | NT | NT | NT | 34 | +++++ | +++ | +++++ |
| 9 | NT | NT | NT | 35 | ++++ | ++ | +++++ |
| 10 | +++ | ++ | +++ | 36 | +++ | ++ | NT |
| 11 | +++ | ++ | NT | 37 | ++ | + | NT |
| 12 | ++ | + | NT | 38 | +++++ | +++ | NT |
| 13 | NT | NT | NT | 39 | ++ | ++ | NT |
| 14 | NT | NT | NT | 40 | ++++ | ++ | NT |
| 15 | +++ | ++ | ++ | 41 | ++ | ++ | NT |
| 16 | +++ | ++ | ++ | 42 | +++ | ++ | NT |
| 17 | ++++ | ++ | NT | 43 | NT | NT | NT |
| 18 | 6.0 | ++ | 4.1 | 44 | ++ | ++ | NT |
| 19 | NT | NT | NT | 45 | +++ | ++ | NT |
| 20 | ++ | + | NT | 46 | +++ | ++ | NT |
| 21 | ++++ | ++ | NT | 47 | ++ | ++ | NT |
| 22 | +++++ | +++ | NT | 48 | ++++ | ++ | NT |
| 23 | NT | NT | NT | 49 | ++ | ++ | NT |
| 24 | +++ | ++ | NT | 50 | + | + | NT |
| 25 | ++ | ++ | NT | 51 | ++ | + | NT |
| 26 | +++ | +++ | NT | 52 | ++ | + | NT |

Note
1. "NT", i.e., "Not Tested", means that the compound was not tested.
2. "+++++" means biological activity $IC_{50} \leq 5.0$ nM;
"++++" means 5.0 nM < biological activity $IC_{50} \leq 10.0$ nM;
"+++" means 10.0 nM < biological activity $IC_{50} \leq 50.0$ nM;
"++" means 50.0 nM < biological activity $IC_{50} \leq 500.0$ nM;
"+" means 500.0 nM < biological activity $IC_{50}$.

It can be seen from the enzymatic activity data or cellular activity data of the compounds of the specific examples that the compounds of the present invention had a strong inhibitory effect on the enzymatic activity FGFR kinases, especially on the enzymatic activity of FGFR2 and/or FGFR3 kinases. The compounds are expected to be developed into a new generation of FGFR inhibitors to meet clinical needs.

All documents mentioned in the present invention are hereby incorporated by reference in their entirety, just as each document is cited separately as a reference. In addition, it should be understood that various modifications and changes may be made by those skilled in the art after reading the above teachings of the present invention and these equivalent forms also fall within the scope defined by the claims appended hereto.

We claim:
1. A compound of formula (II), a stereoisomer, prodrug or pharmaceutically acceptable salt thereof:

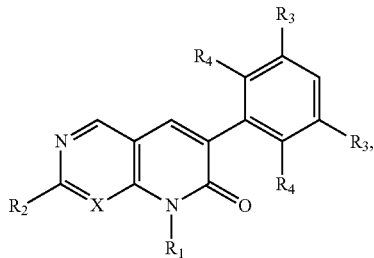

wherein, X is CH or N;
R₁ is selected from the group consisting of H, deuterium, $C_{1-4}$ alkyl, $C_{3-6}$ cycloalkyl, 3-6 membered heterocyclyl, methylsulfonyl and aminosulfonyl, above groups are optionally further substituted by one or more substituents selected from the group consisting of deuterium, F, Cl, cyano, methyl, ethyl, $C_{3-6}$ cycloalkyl, 3-6 membered heterocyclyl, phenyl, methoxy, ethoxy, hydroxy, amino, isopropylamino, dimethylamino and diethyl amino;
R₂ is a 5 membered heteroaryl selected from the group consisting of pyrazolyl, imidazolyl and thiazolyl, above groups are optionally further substituted by one or more substituents selected from the group consisting of deuterium, halogen, cyano, hydroxy, $C_{1-4}$ alkyl, $C_{1-4}$ alkoxy, $C_{3-6}$ cycloalkyl, 3-8 membered heterocyclyl and —C(O)NR₁₃R₁₄, above groups are optionally more further substituted by one or more substituents selected from the group consisting of deuterium, halogen, cyano, hydroxy, $C_{1-4}$ alkoxy, $C_{1-4}$ alkyl, $C_{1-4}$ haloalkyl, $C_{1-4}$ deuterioalkyl, $C_{3-8}$ cycloalkyl, 3-8 membered heterocyclyl, —S(O)ᵣR₁₀ and —NR₁₃R₁₄;
each R₃ is independently selected from the group consisting of H, deuterium, halogen, cyano, $C_{1-4}$ alkyl, $C_{3-6}$ cycloalkyl, oxacyclobutyl, azacyclopentyl, azacyclohexyl, hydroxy, methoxy, ethoxy and isopropoxy, above groups are optionally further substituted by one or more substituents selected from the group consisting of deuterium, halogen, cyano, $C_{1-4}$ alkyl, trifluoromethyl, difluoromethyl, trideuteriomethyl, dideuteriomethyl, cyclopropyl, oxacyclobutyl, methoxy, ethoxy, hydroxy and carboxy;
each R₄ is independently selected from the group consisting of H, deuterium, F, Cl, cyano, $C_{1-4}$ alkyl, $C_{3-6}$ cycloalkyl, oxacyclobutyl, azacyclopentyl, azacyclohexyl, hydroxy, methoxy, ethoxy and isopropoxy, above groups are optionally further substituted by one or more substituents selected from the group consisting of deuterium, F, Cl, cyano, methyl, ethyl, cyclopropyl, methoxy, ethoxy and hydroxy;
R₁₀ is selected from the group consisting of H, deuterium, hydroxy, $C_{1-10}$ alkyl, $C_{1-10}$ alkoxy, $C_{2-10}$ alkenyl, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR₁₃R₁₄, above groups are optionally further substituted by one or more substituents selected from the group consisting of deuterium, halogen, hydroxy, oxo, $C_{1-10}$ alkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy and —NR₁₃R₁₄;
R₁₃ and R₁₄ are each independently selected from the group consisting of H, deuterium, hydroxy, $C_{1-10}$ alkoxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-10}$ alkanoyl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy, amino, monoalkylamino, dialkylamino and $C_{1-10}$ alkanoyl,
or, R₁₃ and R₁₄, together with the nitrogen atom directly attached thereto, form a 4-10 membered heterocyclyl or 4-10 membered heteroaryl, above groups are optionally further substituted by one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 heteroaryl, 5-10 membered heteroaryloxy, amino, monoalkylamino, dialkylamino and $C_{1-10}$ alkanoyl;
each r is independently 0, 1 or 2.

2. The compound of formula (II), the stereoisomer, prodrug or pharmaceutically acceptable salt thereof of claim 1, wherein,
R₁₀ is selected from the group consisting of H, deuterium, hydroxy, $C_{1-4}$ alkyl, $C_{1-4}$ alkoxy, $C_{2-4}$ alkenyl, $C_{3-8}$ cycloalkyl, $C_{3-8}$ cycloalkoxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —NR₁₃R₁₄, above groups are optionally further substituted by one or more substituents selected from the group consisting of deuterium, halogen, hydroxy, oxo, $C_{1-4}$ alkyl, $C_{1-4}$ alkoxy, $C_{3-8}$ cycloalkyl, $C_{3-8}$ cycloalkoxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —NR₁₃R₁₄;
R₁₃ and R₁₄ are each independently selected from H, deuterium, hydroxy, $C_{1-4}$ alkoxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, monoalkylamino, dialkylamino and $C_{1-4}$ alkanoyl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-8}$ cycloalkyl, $C_{3-8}$ cycloalkoxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl, or, R₁₃ and R₁₄, together with the nitrogen atom directly attached thereto, form a 4-8 membered heterocyclyl or 4-8 membered heteroaryl, above groups are optionally further substituted by one or more substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-8}$ cycloalkyl, $C_{3-8}$ cycloalkoxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy, amino, monoalkylamino, dialkylamino and $C_{1-4}$ alkanoyl;

each r is independently 0, 1 or 2.

3. The compound of formula (II), the stereoisomer, prodrug or pharmaceutically acceptable salt thereof of claim 1, wherein the compound is selected from the following compounds:

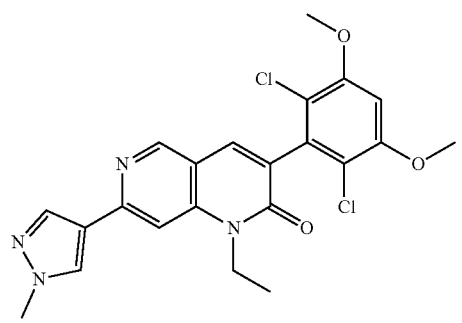

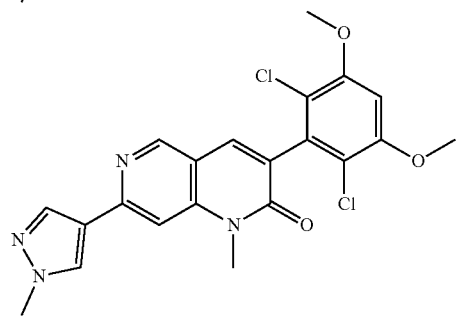

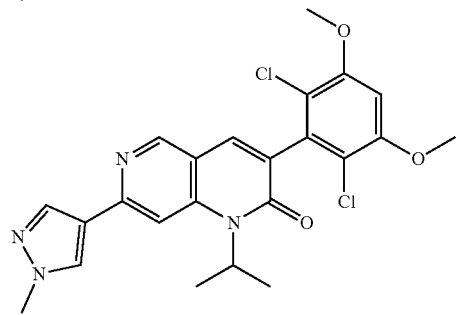

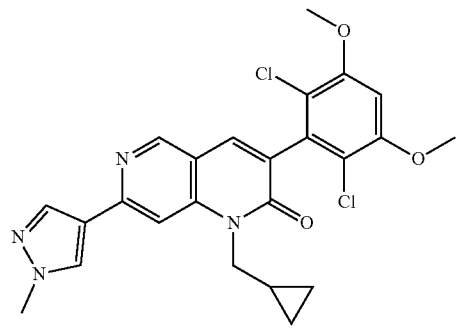

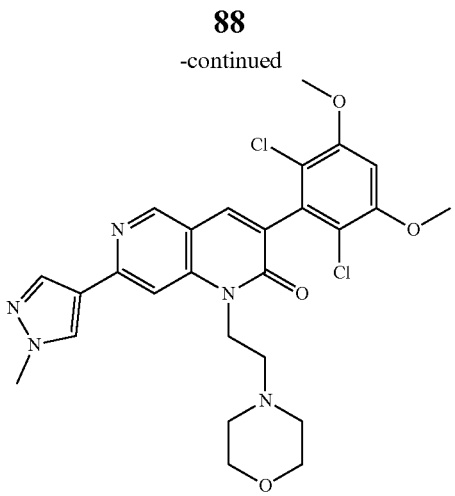

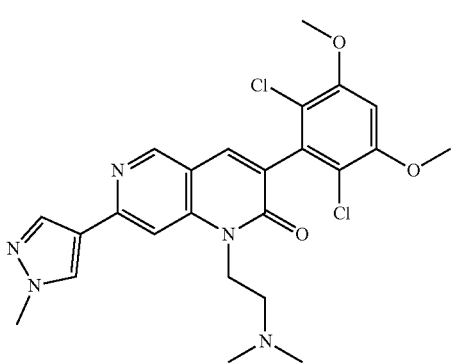

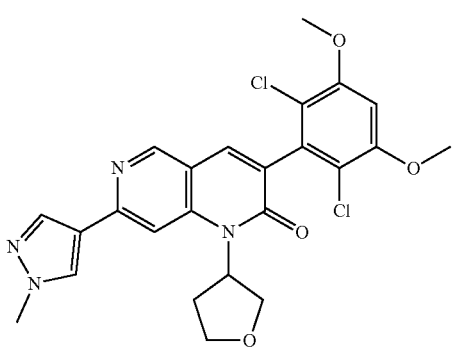

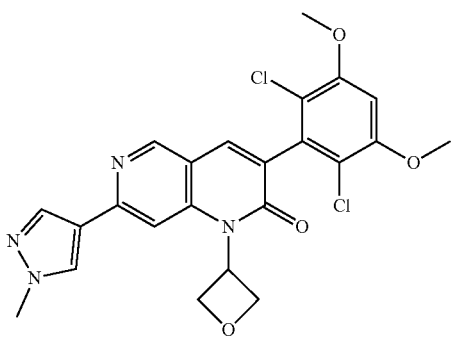

89
-continued
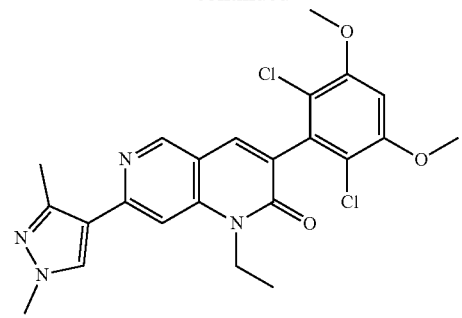
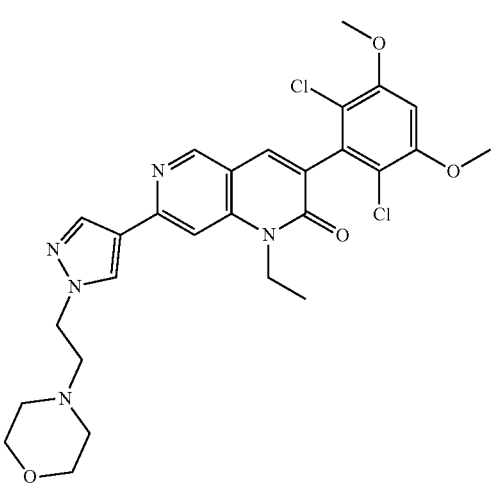
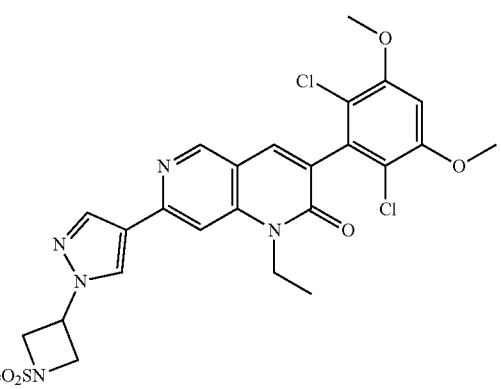
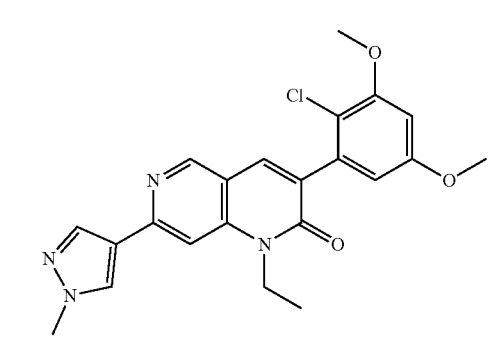
90
-continued
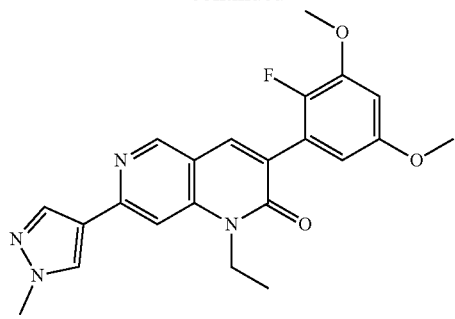
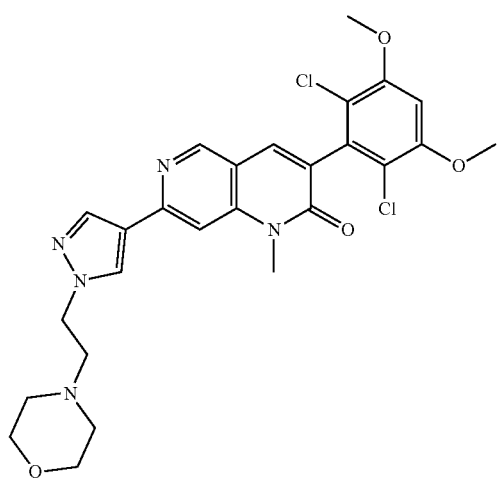
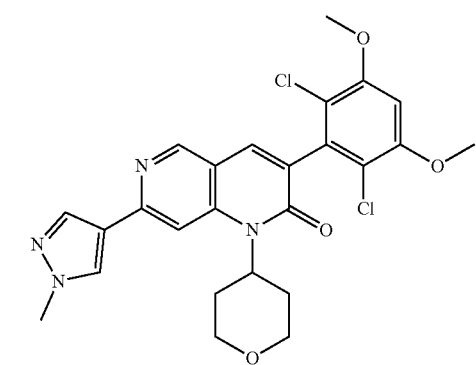
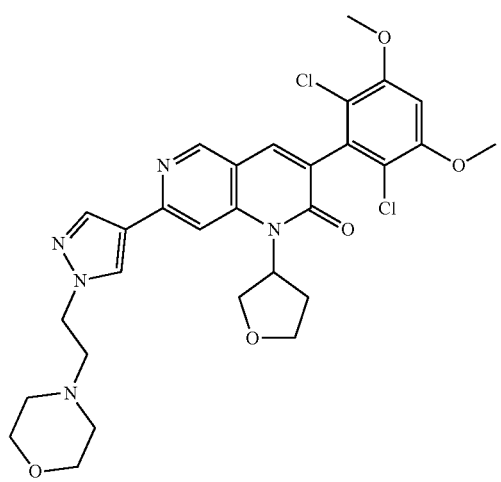

91
-continued
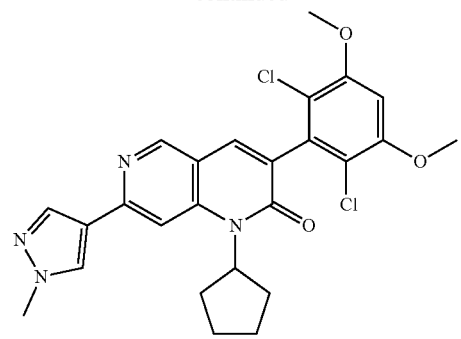
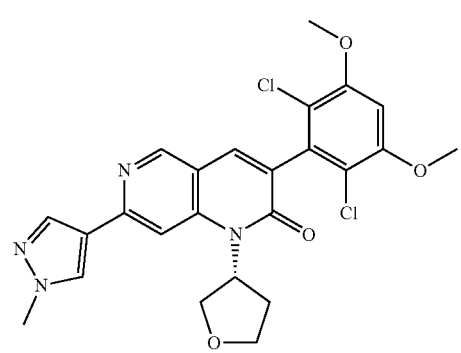
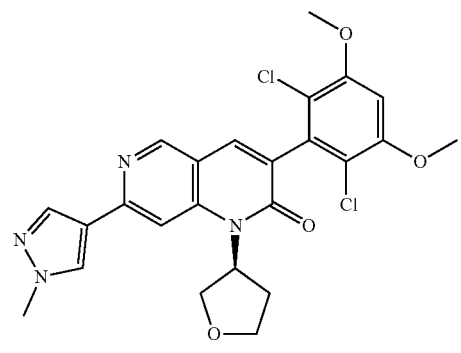
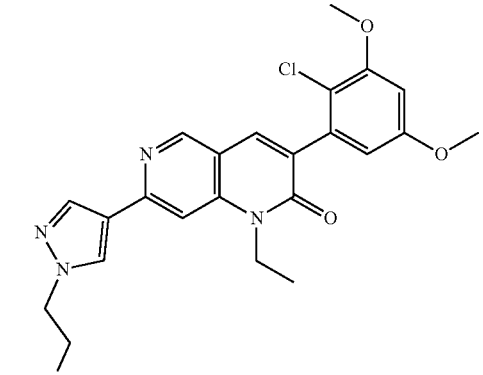
92
-continued
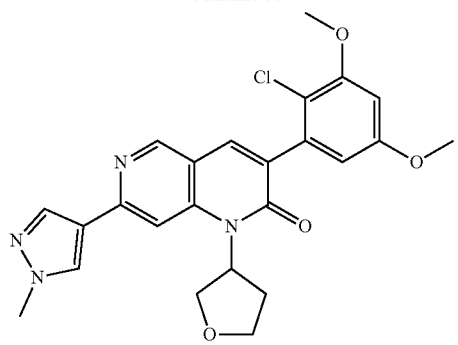
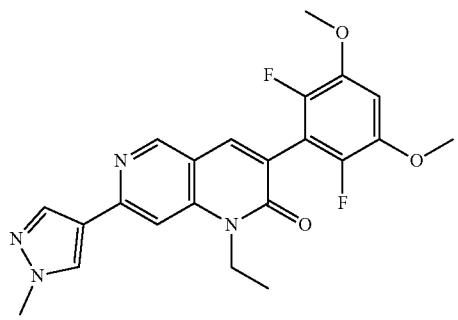
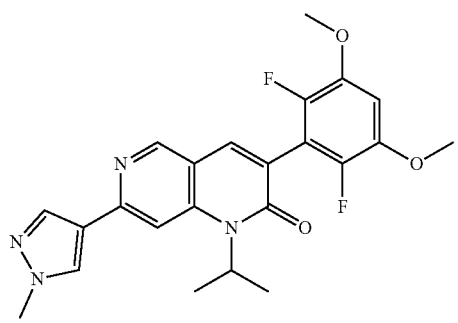
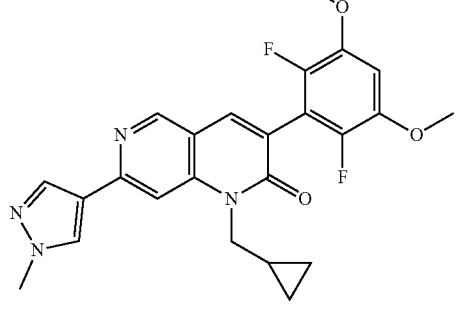
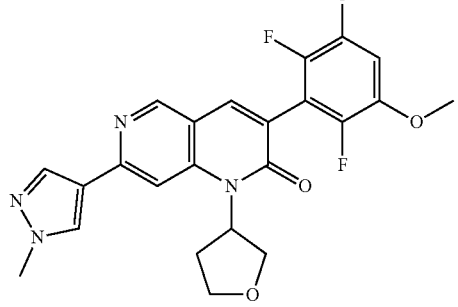

93
-continued
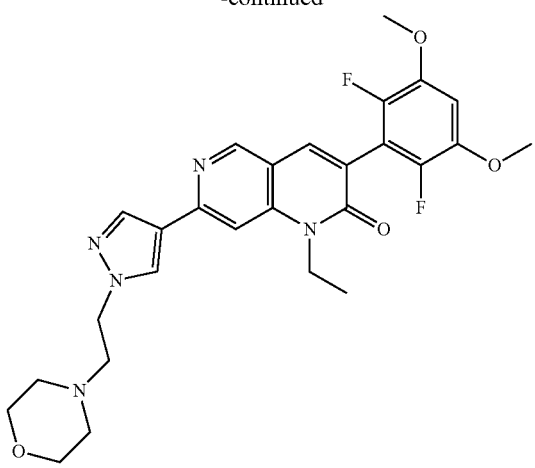
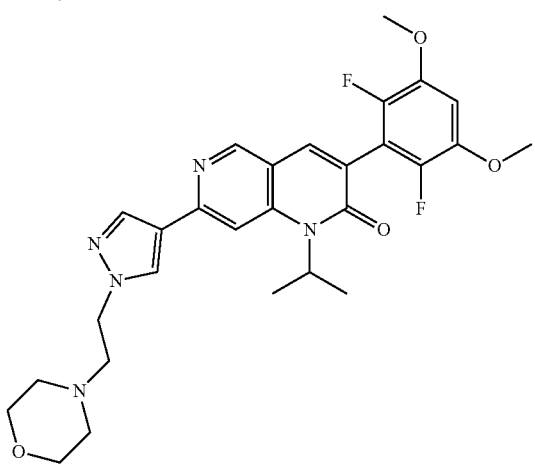
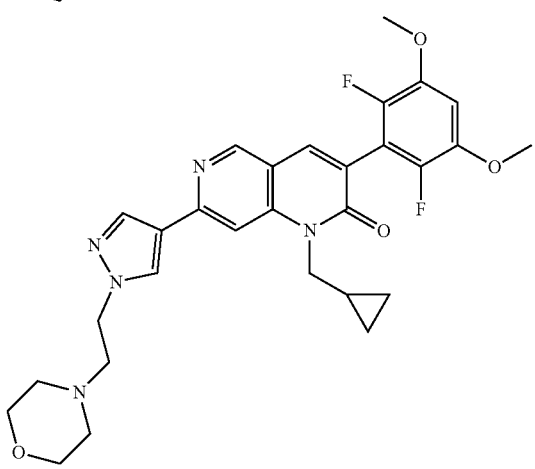
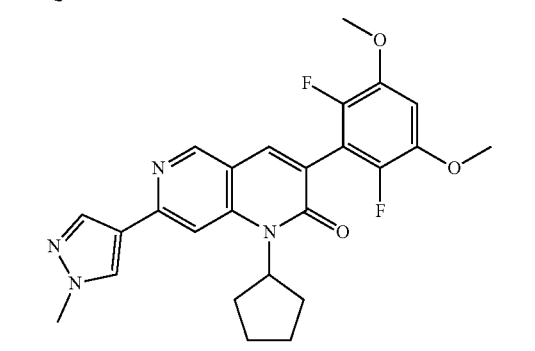
94
-continued
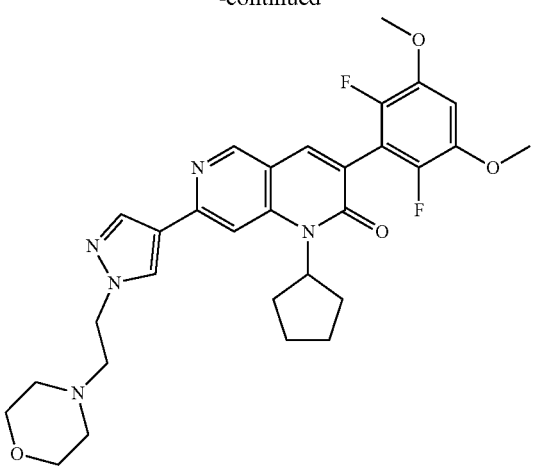
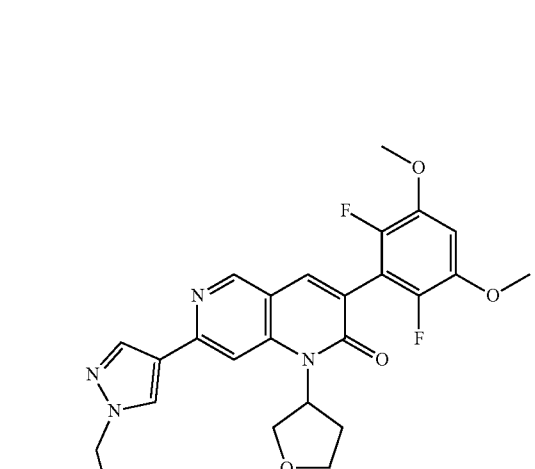
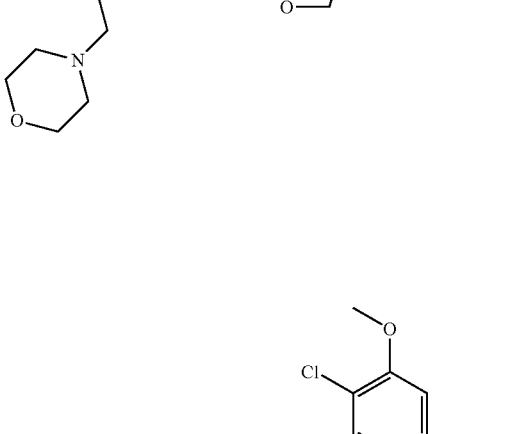
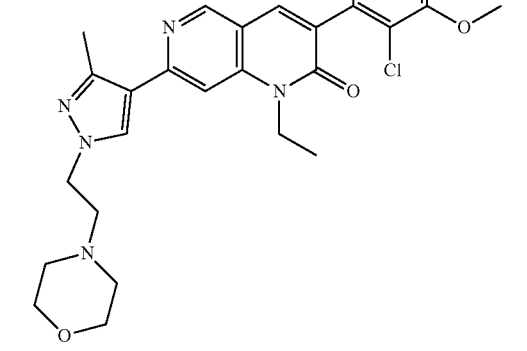

-continued
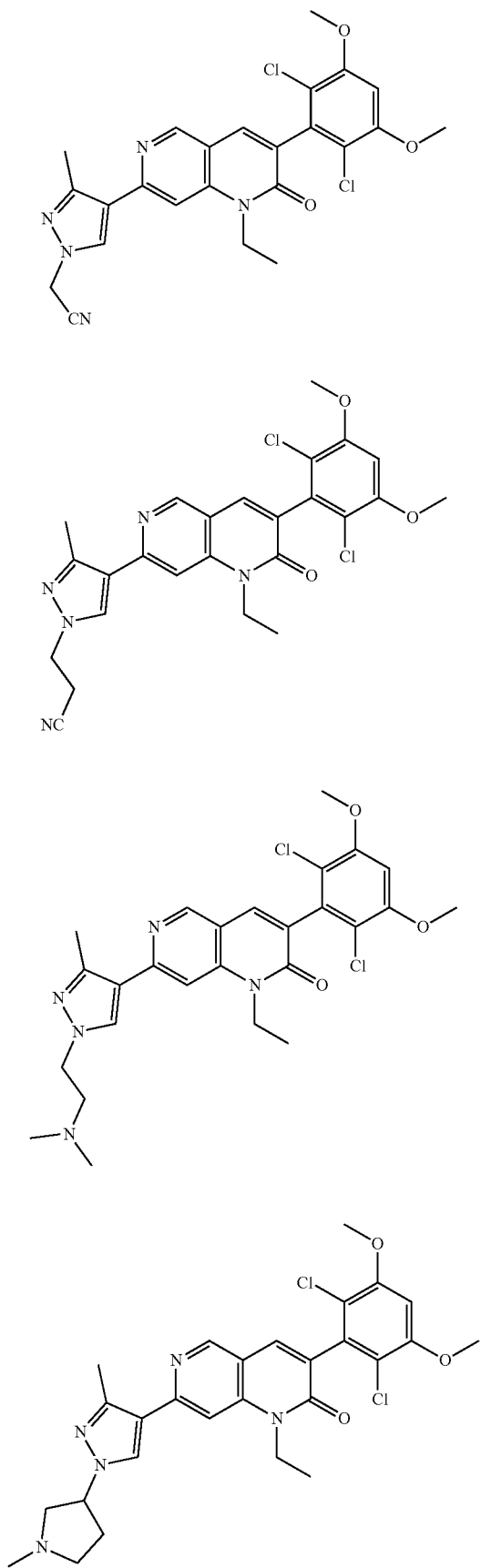
-continued
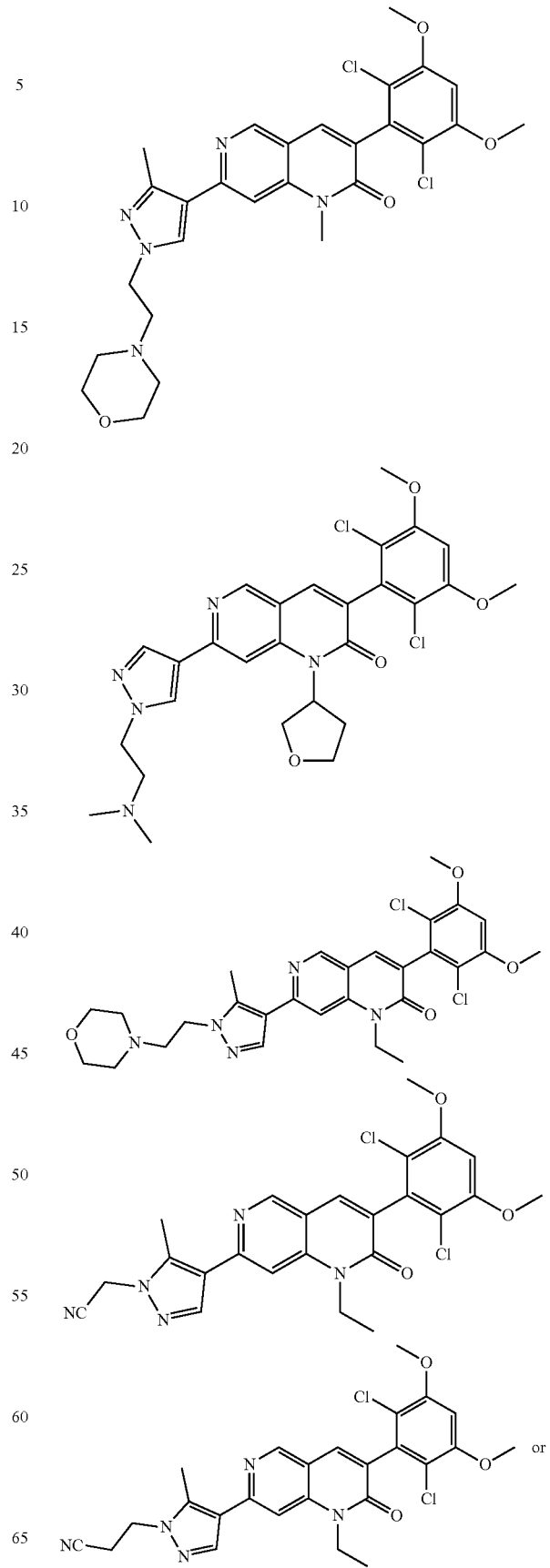

-continued

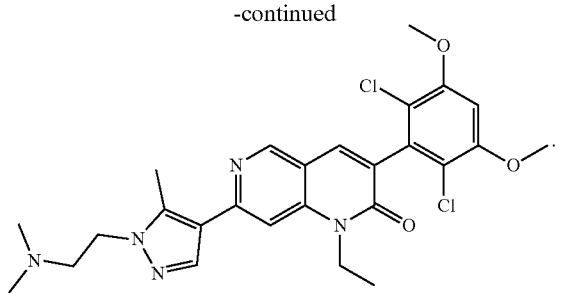

4. A pharmaceutical composition, comprising the compound of formula (II), the stereoisomer, prodrug or pharmaceutically acceptable salt thereof of claim 1, and pharmaceutically acceptable carrier.

5. A method of treating myeloproliferative disease, skeleton or cartilage cell disorder, and hypophosphatemia in a subject, the method comprising administering to the subject in need thereof a therapeutically effective amount of the compound of formula (II), the stereoisomer, prodrug or pharmaceutically acceptable salt thereof of claim 1.

6. The method of claim 5, wherein, the myeloproliferative disease is selected from polycythemia, primary thrombocytosis or primary myelofibrosis; the skeleton or cartilage cell disorder is selected from dysplasia, dyschondroplasia, dwarfism, thanatophoric dysplasia (TD), Apert's syndrome, Crouzon syndrome, Jackson-Weiss syndrome, Beare-Stevenson cutis gyrata syndrome, Pfeiffer syndrome or cranial muscular atrophy syndrome; the hypophosphatemia is selected from X-linked hypophosphatemic rickets, autosomal recessive hypophosphatemic rickets, autosomal dominant hypophosphatemic rickets and tumor induced oothecomalacia.

* * * * *